(12) United States Patent
Peyrottes et al.

(10) Patent No.: US 8,614,312 B2
(45) Date of Patent: Dec. 24, 2013

(54) METHOD FOR PREPARING NUCLEOTIDES AND RELATED ANALOGUES BY SYNTHESIS ON SOLUBLE SUBSTRATE, AND BIOLOGICAL TOOLS THUS PREPARED

(75) Inventors: Suzanne Peyrottes, Grabels (FR); Christian Perigaud, Grabels (FR); Céline Crauste, Montpellier (FR)

(73) Assignees: Centre National de la Recherche Scientifique, Paris (FR); Universite Montpellier 2 Sciences et Techniques, Montpellier (FR)

( * ) Notice: Subject to any disclaimer, the term of this patent is extended or adjusted under 35 U.S.C. 154(b) by 254 days.

(21) Appl. No.: 12/735,871

(22) PCT Filed: Feb. 23, 2009

(86) PCT No.: PCT/FR2009/000197
§ 371 (c)(1),
(2), (4) Date: Jan. 27, 2011

(87) PCT Pub. No.: WO2009/115694
PCT Pub. Date: Sep. 24, 2009

(65) Prior Publication Data
US 2011/0118454 A1    May 19, 2011

(30) Foreign Application Priority Data
Feb. 21, 2008  (FR) ...................................... 08 00943

(51) Int. Cl.
*C07H 21/00* (2006.01)
*C12Q 1/68* (2006.01)
*C07H 21/02* (2006.01)

(52) U.S. Cl.
USPC ........................... 536/25.3; 536/23.1; 435/6.1

(58) Field of Classification Search
USPC .................................. 536/23.1, 25.3; 435/6.1
See application file for complete search history.

(56) References Cited

U.S. PATENT DOCUMENTS

| 5,703,223 A * | 12/1997 | Wickstrom et al. ........ 536/25.33 |
| 6,380,378 B1 | 4/2002 | Kitamura et al. |
| 2007/0042407 A1 | 2/2007 | Milton et al. |

FOREIGN PATENT DOCUMENTS

WO   WO 2007/020457 A2   2/2007

OTHER PUBLICATIONS

International Search Report issued by the International Searching Authority (ISA/EPO) on Aug. 21, 2009 in connection with International Application No. PCT/FR2009/000197.
Written Opinion of the International Searching Authority (ISA/EPO) in connection with International Application No. PCT/FR2009/000197, 2010.

(Continued)

*Primary Examiner* — Jezia Riley
(74) *Attorney, Agent, or Firm* — John P. White; Cooper & Dunham, LLP

(57) ABSTRACT

The invention concerns a method for preparing monomer nucleotides or nucleotide analogues comprising the steps of: (1) coupling a soluble polyethylene glycol support provided with at least one diacid or ether-acid linker and a monomer nucleoside or nucleoside analogue to an amine group or hydroxyl group of the nucleoside with the aid of a coupling agent; (2) at least one step for phosphorylation of said nucleoside or nucleoside analogue coupled to said support with a phosphorylation agent; (3) cleavage of said support and recovery of at least one monomer nucleotide or nucleotide analogue. The nucleotides prepared are biological tools.

29 Claims, 3 Drawing Sheets

(56) References Cited

OTHER PUBLICATIONS

Figure 1:
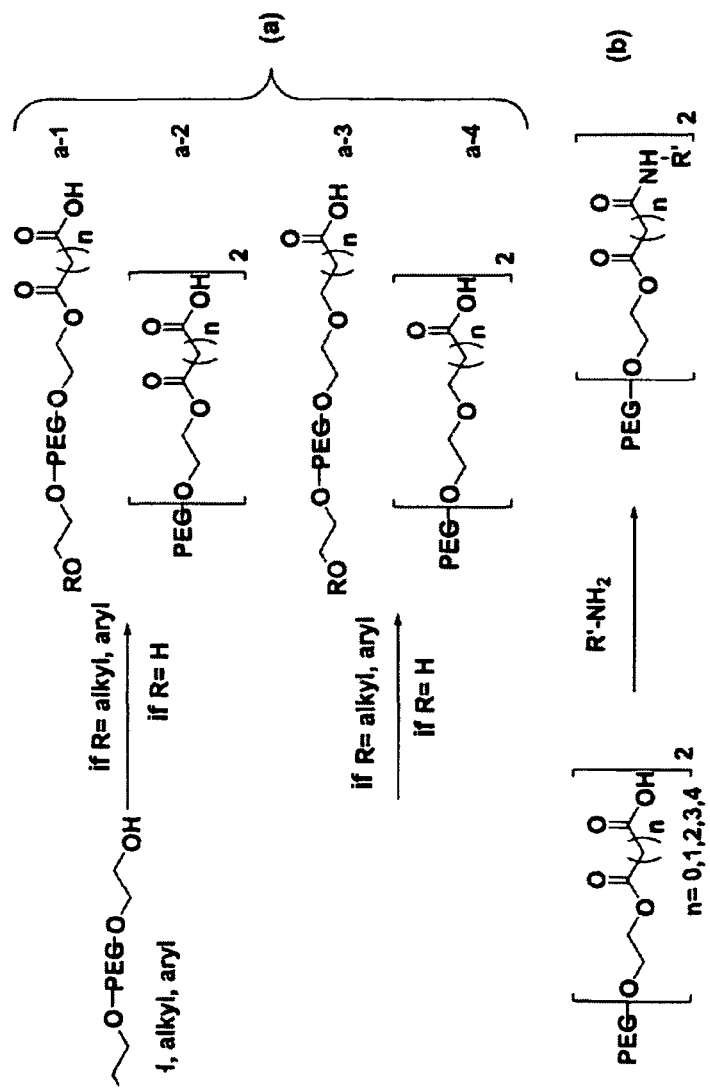
Figure 1:
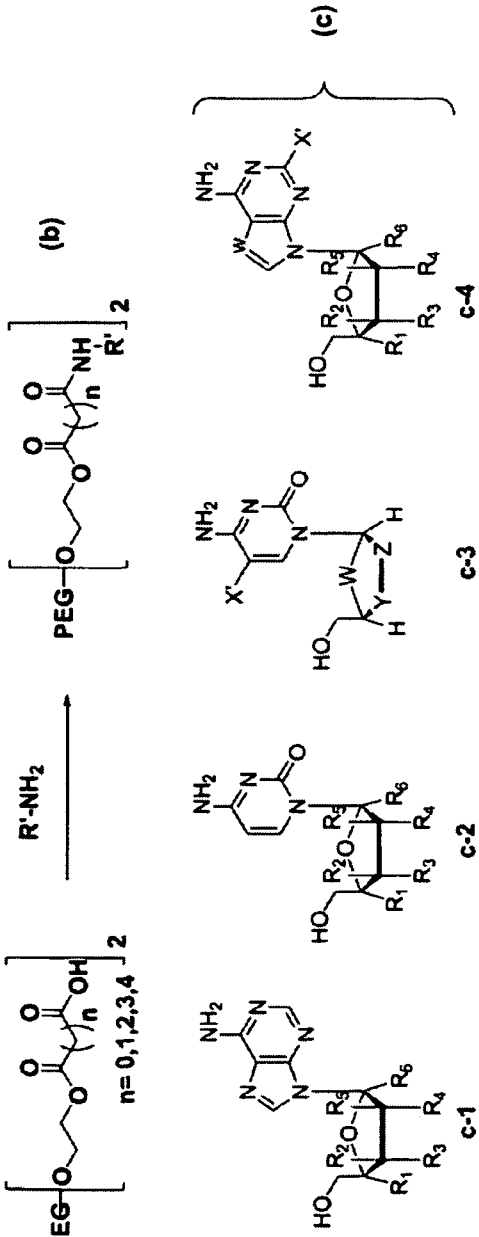
Figure 1:
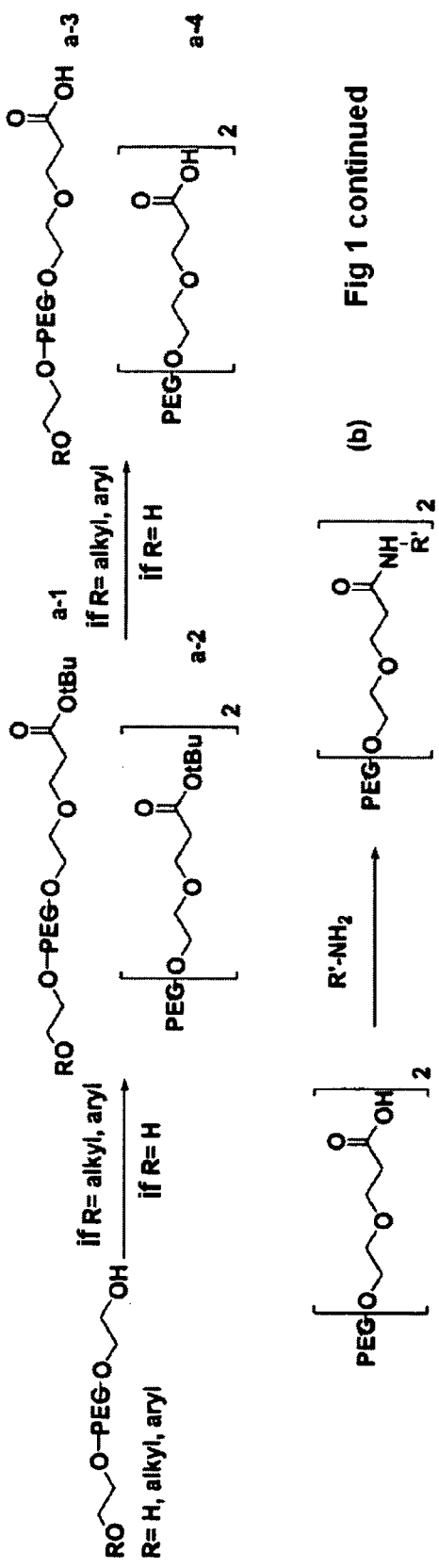

Notification of Transmittal of International Preliminary Report on Patentability, including an International Preliminary Report on Patentability and Written Opinion of the International Searching Authority in connection with PCT/FR2009/000197, 2010.

Beyer, E (1991). Towards the Chemical Synthesis of Proteins. Angewandte Chemie, 30, 2, 113-216.

Bayer, E. & Geckeler, K. (1974). Lösliche Copolymere aus 1-Vinyl-2-pyrrolidinon und Vinylacetat zur Synthase von Peptiden. Liebigs Ann. Chem., 10, 1671-1674.

Bayer, E. & Mutter, M. (1972). Liquid Phase Synthesis of Peptides. Nature, 273, 512-513.

Blecher, H. & Pfaender, P. (1973). Polyäthylenimin als wasserlöslicher Träger bei der N-Carboxyanhydrid-Methode. Leibigs Ann. Chem., 1263-1268.

Burgess, K. & Cook, D. (2000). Syntheses of Nucleoside Triphosphates. Chemical Reviews., 100, 2047-2059.

Donga, R, Khaliq-Uz-Zaman, S, Chan T. Damha, M. (2006). A Novel Apprach to Oligonucleotide Synthesis Using an Imidazolium Ion Tag as a Soluble Support. Journal of Organic Chemistry, 71, 7907-7910.

Gallop, M, Barrett, R., Dower, W., Fodor, S. & Gordon, E. (1994 Applications of Combinatorial Technologies to Drug Discovery. Journal of Medicinal Chemistry. 37, 9, 1233-1251.

Geckeler, K & Bayer, E. (1974). Copolymerisation von Aminosäure-alkenylestern. Die Makromolekulare Chemie. 175, 1995-2001.

Gold, L., Polisly, B., Uhlenbeck, O. & Yarusm. (1995). Diversity of Oligonucleotide Functions. The Annual Review of Biochemistry. 64, 763-797.

Parang, K, Fournier, E. & Hindsgaul, O. (2001). A Solid Phase Reagent for the Capture Phosphorylation of Carbohydrates and Nucleosides. Organic Letters. 3, 2, 307-309.

Thompson, L. & Ellman, J. (1996). Synthesis and Applications of Small Molecule Libraries. Chemical Review. 96, 555-600.

Weiss, R & Schlierf, C. (1971). A New Route to Dewar-Benzenes. Angewandte Chemie International Edition. 10, 11, 811.

Japanese Patent Application No. 2000-327694, published Nov. 28, 2000, including an English translation of the abstract and of paragraph 0017.

Abstract published May 1, 2003 in English for WO 03/035665 (A1) (corresponds to cited JP 2005-512978, published May 12, 2005).

* cited by examiner

METHOD FOR PREPARING NUCLEOTIDES AND RELATED ANALOGUES BY SYNTHESIS ON SOLUBLE SUBSTRATE, AND BIOLOGICAL TOOLS THUS PREPARED

This application is a §371 national stage of PCT International Application No. PCT/FR2009/000197, filed Feb. 23, 2009, designating the United States, and claims priority of French Patent Application No. 08/00943, filed Feb. 21, 2008, the contents of each of which are hereby incorporated by reference into this application.

The present invention concerns a method for preparing nucleotide monomers or monomers of nucleotide analogues on soluble support, more precisely a method for preparing nucleotides, i.e. mono-, di- and triphosphate nucleosides.

The chemical synthesis of nucleotides and oligonucleotides has been the subject of intense research since the start of the 1980s. In 1983, a method for the synthesis of oligonucleotides on a solid support was developed by McBride and Caruthers. That method, termed the "phosphoramidites method", used a solid support to which a nucleoside was attached. The solid supports used in that method were glass beads with a controlled porosity. The first nucleoside was attached to the solid support via the hydroxyl in the 3' position and the synthesis advanced from the 3' end to the 5' end of the nucleic acid chain. More precisely, by removing a labile acid protective group in the 5' position, a hydroxyl function was liberated. The terminal nucleophilic group was then coupled to a 3'-O-phosphoramidite monomer protected in the 5' position and optionally on the heterocycle, in the presence of an activator. The 3',5'-phosphite triester bond was then oxidized to produce a phosphotriester linkage. In that synthesis method, the steps of deprotection, coupling, capping and oxidation were carried out in succession and were repeated until an oligomer of the desired length had been obtained.

Since then, other synthesis methods have used solid supports. Those methods have been described by Gallop et al, *J. Med. Chem.* 37, 1233 (1994), Gold et al, Annu Rev. Biochem. 64, 763 (1995) and Thompson et al, *Chem Rev,* 96, 555 (1996).

Although satisfactory results were obtained, solid support methods have certain disadvantages, for example non-linear behaviour in terms of kinetics, an irregular distribution over the support or because of the support, problems with solvation, an insufficient degree of coupling or problems with synthesis due to the heterogeneous nature of the reaction conditions, and more precisely of the reaction medium. Furthermore, solid supports are very expensive, which renders large scale synthesis very costly. Moreover, the synthesis yield in conventional solid phase is not always satisfactory, due in particular to difficulties in purifying the product and separation of the product from truncated sequences. Finally, with solid support methods, the reaction may be difficult to track.

Other alternative methods have thus been investigated, which would use more homogeneous reaction conditions and the use of soluble polymer supports has been proposed. That methodology is termed "liquid phase synthesis" and overcomes certain problems encountered with solid supports. Those methods use polyethylene glycol (PEG) as the soluble support, as can be seen in Mutter et al, *Angew. Chem. Int. Ed. Engl.* 10, 811 (1971) and Bayer et al, *Nature* (London) 237, 512 (1972).

Apart from PEG, other supports are known in the art, in particular PEG grafted onto cross linked polystyrene (Bayer, E. *Angew. Chem. Int. Ed. Engl* 30,113 (1991). The synthesis of peptide on polyethylene imine is also known, the support having a molecular weight in the range 30000 to 40000 (Pfaender et al in *Peptides*; Proc. Eight Eur. Pep. Symp; Ann Arbor Science; North Holland p. 137 (1967) and Blecher et al *Liebigs. Ann Chem,* 1263 (1973)). Polyvinyl alcohol copolymers (Bayer et al, Liebigs An Chem, 1671 (1974)) and polyvinyl alcohol-poly(1-vinyl-2-pyrrolidone) copolymers (Geckeler et al, Makromol. Chem., 175, 1995 (1974)) have also been used as a soluble support for the synthesis of peptides.

One of the major disadvantages of those first peptides syntheses on soluble support resides in the yields obtained for the expected peptide, which are low due to incomplete cleavage and/or predominant side reactions.

Other cleavage methods were then used, such as those induced by labile acid or base linkages, labile thiol bonds and photolytic salting out of peptides after synthesis.

One recent method for synthesizing oligopeptides, oligosaccharides and oligonucleotides using liquid phase synthesis is described in WO 2006/096963. The ionic liquid used as a liquid support is an onium type organic salt, for example a heterocyclic quaternary ammonium cation and an anion, for example $Cl^-$, $Br^-$, $BF_4^-$, $PF_6^-$, $SbF_6^-$, $CuCl_2^-$ or $AlCl_4^-$. The cation examples also include substituted pyridines and 1,3-disubstituted imidazoles.

Donga et al, J. Org. Chem. 71, 7907-7910 (2006) describes the synthesis of oligonucleotides on a soluble ionic liquid type support (ILSS) with high yields and with such a purity that no chromatography step is necessary for purification of the intermediates before cleavage of the support. In this method, the soluble ionic support is synthesized from N-methylimidazole and 2-bromoethanol then isolated by anion exchange chromatography. The 3'-succinylated 5'-DMT-thymidine derivative was coupled to the ionic liquid using dicyclohexylcarbodiimide (DCC) and a catalytic quantity of 4-(dimethylamino)pyridine (DMAP) in acetonitrile, to produce the nucleoside grafted to the ionic liquid. The ionic liquid was isolated and purified by precipitation from an ethyl ether/ethyl acetate solution, treated in chloroform and washed with water. Various oligonucleotides were obtained from the corresponding grafted nucleoside using that method.

U.S. Pat. No. 6,001,966 describes a method for the sequential synthesis of oligonucleotides in solution by reaction of monomer units.

Regarding the production of phosphated monomers, Parang et al in *Organic Letters Vol.* 3, No. 2 (2001) describes a supported reagent for producing carbohydrate monophosphates and a nucleoside using a cross-linked polystyrene-divinylbenzene copolymer functionalized with cyanoethyl-N,N-diisopropyl phosphoramidite as a phosphitylation agent. That immobilized agent is coupled with alcohols in the presence of 1H-tetrazole in order to produce phosphite-triesters linked to polymer that are then oxidized to the corresponding phosphotriesters. The immobilized phosphate derivative is then deprotected and cleaved from the solid support.

Thus, although various methods are known for synthesizing nucleotides, there are still problems both with solid phase syntheses and with syntheses in solution, in particular problems with low yields and lengthy purification procedures. For the synthesis of triphosphate nucleosides, there is a genuine need for a general method that produces triphosphate nucleosides in high yields and that can be applied to many substrates (Burgess and Cook, Synthesis of Nucleoside Triphosphates, *Chem. Rev.* 100(6) 2047-2060 (2000).

There is thus a need for a method for producing nucleotide monomers or nucleotide analogues in large quantities, at low cost and without laborious purification steps.

One aim of the present application is to overcome these problems of the prior art concerning the synthesis of nucleotide monomers.

The invention concerns a novel method for the preparation of phosphorylated nucleotides or nucleoside analogues (scheme below),

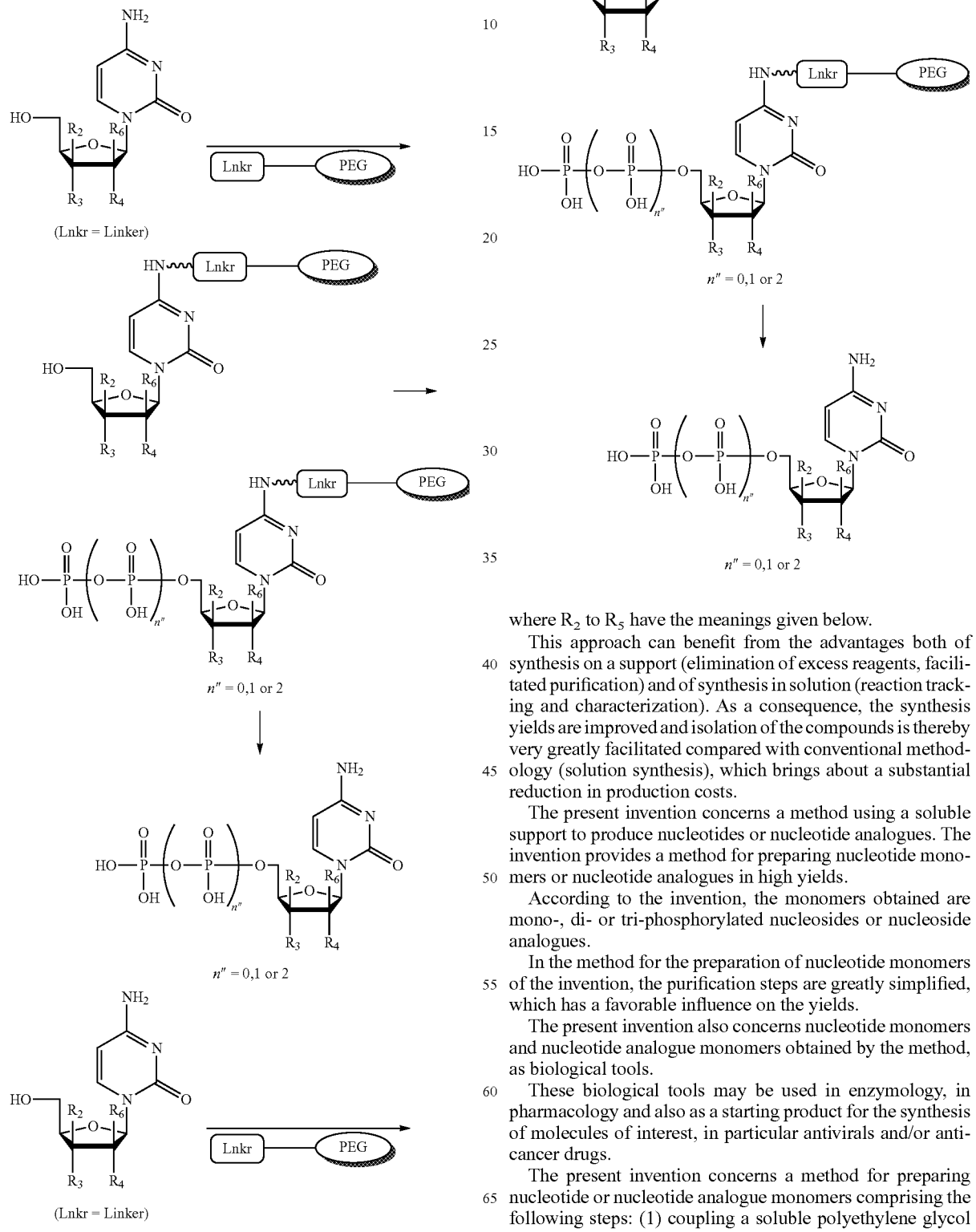

where $R_2$ to $R_5$ have the meanings given below.

This approach can benefit from the advantages both of synthesis on a support (elimination of excess reagents, facilitated purification) and of synthesis in solution (reaction tracking and characterization). As a consequence, the synthesis yields are improved and isolation of the compounds is thereby very greatly facilitated compared with conventional methodology (solution synthesis), which brings about a substantial reduction in production costs.

The present invention concerns a method using a soluble support to produce nucleotides or nucleotide analogues. The invention provides a method for preparing nucleotide monomers or nucleotide analogues in high yields.

According to the invention, the monomers obtained are mono-, di- or tri-phosphorylated nucleosides or nucleoside analogues.

In the method for the preparation of nucleotide monomers of the invention, the purification steps are greatly simplified, which has a favorable influence on the yields.

The present invention also concerns nucleotide monomers and nucleotide analogue monomers obtained by the method, as biological tools.

These biological tools may be used in enzymology, in pharmacology and also as a starting product for the synthesis of molecules of interest, in particular antivirals and/or anti-cancer drugs.

The present invention concerns a method for preparing nucleotide or nucleotide analogue monomers comprising the following steps: (1) coupling a soluble polyethylene glycol support provided with at least one diacid or ether-acid linker and a nucleoside or nucleoside analogue monomer to an exocyclic amine or hydroxyl group of the nucleoside, using a coupling agent; (2) carrying out at least one phosphorylation of said nucleoside or nucleoside analogue coupled to the support, with a phosphorylation agent. Cleavage of the linker between the support and the monomer may then take place and thus allows the nucleotide or nucleotide analogue monomer to be recovered.

Thus, in general, in accordance with the invention, the linker is attached to the soluble PEG type support, then that support is coupled to a nucleoside or analogue via the linker, then the coupled nucleoside is phosphorylated in one or more phosphorylation steps. Next, the nucleotide can be cleaved in order to recover it.

This method means that bespoke biological tools or phosphorylated effectors (mono-, di- or tri-phosphorylated nucleosides), nucleotides or analogues, natural or not, can be obtained, avoiding the usual lengthy, fastidious and onerous purification steps. The synthesis takes place in solution, which means that the reaction can be tracked and the intermediates can be characterized using the usual techniques. This on-support technique has the advantages of facilitated purification of the intermediate and final products, usually ionic, and allows the reagents used in excess to be eliminated. As an example, commercial AraCTP is more than 13 times more expensive than the cost price (reagents and equipment) using the proposed method of the invention. Regarding yields, the method of the invention also has a higher yield than the usual methods.

The present invention will be better understood from the following description and the preferred implementations as well as from the following examples and the accompanying drawings.

FIG. 1 is a scheme showing on the one hand attachment (a) of various linkers to soluble supports, as well as the supports once these linkers have been attached, then functionalization of a soluble support by coupling (b) with a nucleoside via the exocyclic amine function of a R'NH$_2$ heterocycle. This figure also shows at (c) various aminated heterocycles that can be coupled to a support in the method of the invention: a purine base nucleoside (c-1), a pyrimidine base nucleoside (c-2), a structural analogue of a pyrimidine base modified on the sugar and the base (c-3), illustrating the analogues of nucleosides by sugar modification, as well as an analogue of a purine base nucleoside (c-4) illustrating the analogues of nucleosides by modification of the base.

Figure 2:
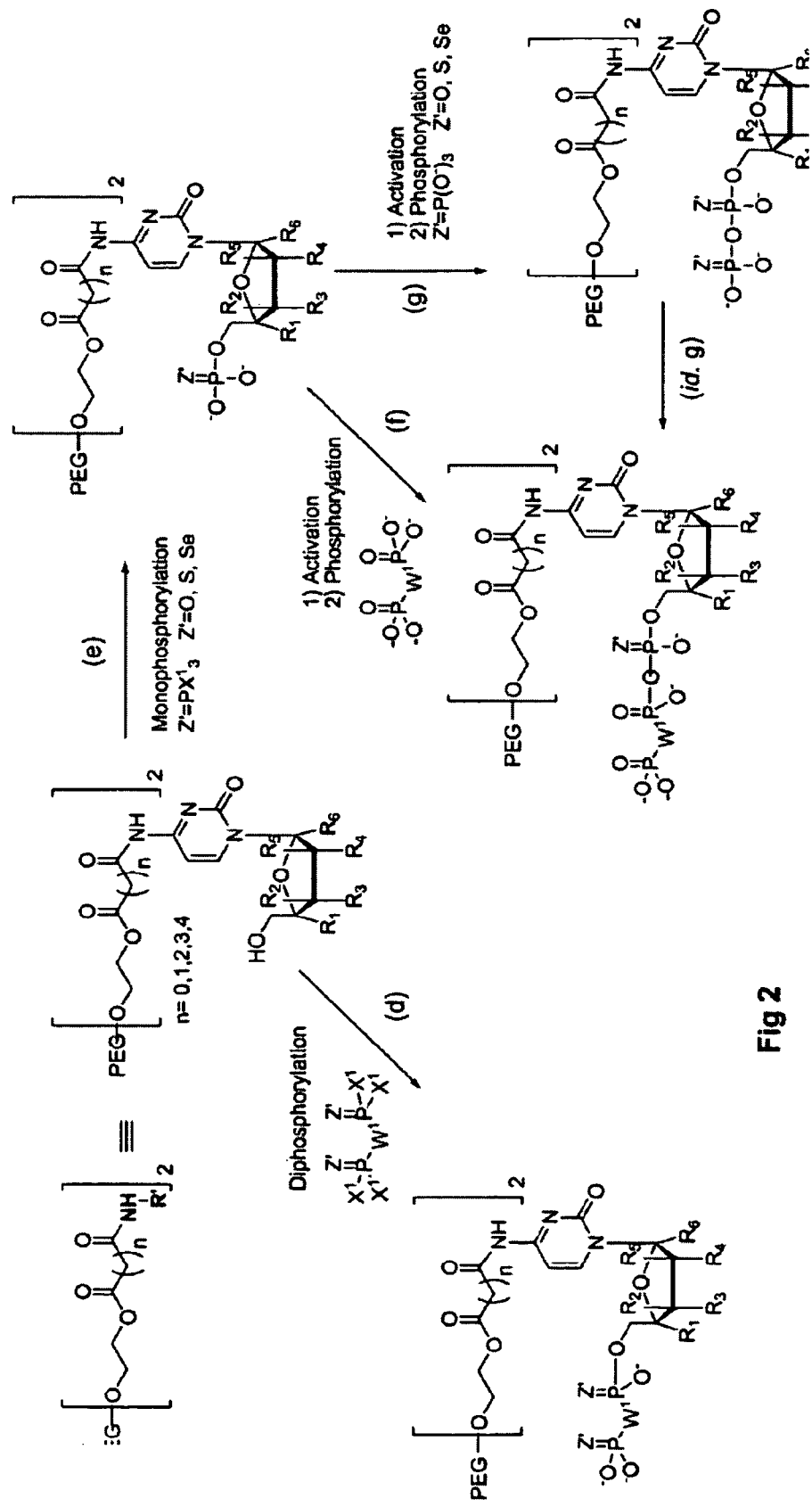

FIG. 2 is a scheme showing, for case (a-2), phosphorylation steps which may be carried out in particular starting from the grafted nucleosides of FIG. 1. Direct diphosphorylation (d) and a monophosphorylation (e) are shown, which may, following an activation step, be followed by a second monophosphorylation (g) leading to diphosphated nucleosides or again to two successive monophosphorylations (g) or one diphosphorylation (f) leading to triphosphated nucleosides.

The term "monomer" as used here is assumed to mean that the nucleoside or nucleotide comprises a base, a sugar and in the case of nucleotides, one or more phosphate group(s). Thus, oligomers are excluded.

The first step of the invention consists of coupling a nucleosidic monomer onto a soluble support having a linker.

In accordance with the invention, the soluble support used may be a polyethylene glycol (PEG) support having at least one acid, diacid or ether-acid joining linker. The term "at least one linker" means one or two. More precisely, the PEG provided with at least one linker may have formula:

(I) RO—C$_2$H$_4$—O-PEG-O—C$_2$H$_4$—O—C(O)—(CH$_2$)$_p$—COOH in which R is an alkyl or benzyl or aryl group or —C(O)—(CH$_2$)$_{n'}$—COOH and p and n', independently of each other, represent 0 or a whole number from 1 to 10; or (II) RO—C$_2$H$_4$—O-PEG-O—C$_2$H$_4$—O—(CH$_2$)$_m$—COOH in which R is an alkyl or benzyl or aryl group or —(CH$_2$)$_{m'}$—COOH and m and m', independently of each other, represent 0 or a whole number from 1 to 3.

Preferably in accordance with the invention, p or n' in formula (I) is less than 6 and preferably, p or n' in formula (I) is a whole number from 0 to 4 and in formula (II), m and m' are preferably 1 or 2. As will become apparent from the detailed description, a preferred linker is of the succinate type.

In the above formulae, the alkyl radical is preferably linear or branched, C$_1$ to C$_{12}$, and the aryl radical is preferably selected from phenyl, tolyl and o-tolyl. Preferably, R is methyl or benzyl.

The term "polyethylene glycol" (PEG) is not limited to polyethylene glycol per se, but includes any polyethylene glycol derivative, containing, for example, hydroxyl groups at both of its ends or a hydroxyl group at one and a methoxy group at the other, polyethylene glycol monomethyl ether and poly(oxyethylene) glycol or analogues.

More generally, as used here, "soluble support" means a support of the polyethylene glycol type having a diacid linker or an ether-acid linker or two such linkers. Preferably, the soluble support of the present invention is a polyethylene glycol (PEG), polyethyleneglycol monomethylether or a poly(oxyethylene)glycol comprising at least one diacid linker or ether-acid linker.

The molecular weight of said PEG of the invention is preferably in the range from approximately 3000 to approximately 6000. Preferably, the PEG has a molecular weight of approximately 4000.

The diacid or ether-acid linker is attached to the PEG by various methods depending on the type of linker to be attached, the general method being illustrated in the examples.

As an example, if the linker, of the succinate type, has to be associated with PEG, the procedure comprises dissolving PEG in a solvent, adding the corresponding acid anhydride, stirring at ambient temperature, then concentrating the reaction mixture under reduced pressure, and precipitating the PEG comprising the diacid linker. In the precise case of a succinate linker, the linker promoter is succinic anhydride. In the case of an oxalate linker, oxalyl chloride is used. More generally, a carboxylic acid, anhydride or acid chloride, for example, may be used to functionalize the PEG. The ether-acid linker may, for example, be obtained by two synthesis pathways involving oxidation of the terminal alcohol of the support, as illustrated in the examples, or by reacting PEG with an alkyl acrylate.

If the linker is ethanoic acid, the method for forming the linker comprises, for example, oxidation of PEG by chromium salts, stirring the mixture at ambient temperature and precipitating the modified PEG.

As an example, the following may be used:

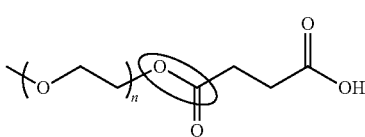

a functionalized support with a succinyl linker;
or a functionalized support of the PEG-acid type:

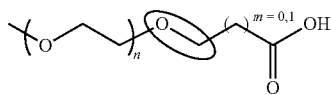

In the two above formulae and in the scheme below depending on the molecular weight of the PEG.

The phosphorylation reaction is carried out in the same manner regardless of the nature of the linker. In this variation, the linker may remain attached to the PEG support during the cleavage step. Preferred PEG-acid supports are those for which m"=1.

The linker above is termed an "acid" linker for m"=0.

The skilled person will be able to adapt the method for attaching the linker to the selected soluble support and to the required linker. As can be seen in FIG. 1, the PEG may be bifunctional (HO-PEG-OH), R representing H and carrying two linkers (a-2; a-4), or monofunctional (RO-PEG-OH) and then carry one linker (a-1; a-3), R representing alkyl, benzyl or aryl.

In a particular implementation of the invention, the PEG-OH is functionalized with t-butyl acrylate, and after a deprotection step, the functionalized PEG-acid, PEG-O(CH$_2$)$_2$—COOH, is obtained in accordance with the following scheme:

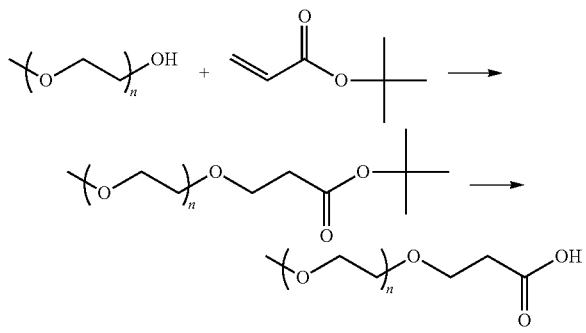

Thus, in accordance with the invention, in accordance with a particular implementation, PEG-O-bis(succinyl-nucleoside) is used.

In another particular implementation, PEG-bis (OCH$_2$CH$_2$—CO-nucleoside) is used.

A particular advantage of PEGs functionalized by a 3-hydroxypropanoic acid linker resides in simplification of the subsequent procedure Once the linker has been attached to the soluble support, the support is brought into the presence of nucleoside or nucleoside analogue.

Coupling with the soluble support may take place via an exocyclic amine group, using a coupling agent and resulting in the formation of an amide bond, this variation being illustrated in FIG. 1(b) or via a hydroxyl group of the nucleosidic analogue or nucleoside and resulting in the formation of an ester bond.

Preferably, according to the invention, coupling is carried out on the exocyclic amine function. Thus, coupling is preferably carried out on the exocyclic nitrogen of the nucleoside base. It is, for example, the exocyclic amine function of cytosine, from the pyrimidine bases, and adenine or guanine, of the purine bases, illustrated in FIG. 1 (b and c).

The coupling method may vary depending on the nucleoside to be coupled and the selected support. In general, the PEG with a linker is mixed with the nucleoside or nucleoside analogue which is to be phosphorylated, and the coupling agent is added to the mixture. The reaction mixture is stirred for a period sufficient to obtain coupling, the solvents are evaporated off and the final product is precipitated or possibly re-crystallized.

The term "nucleoside" as used here means various compounds comprising on the one hand a sugar and on the other hand a heterocycle. Natural nucleosides are substances the hydrolysis of which produces one molecule of ribose or deoxyribose and a purine heterocycle (adenine, guanine) or pyrimidine heterocycle (cytosine, uracil, thymine). The nucleosidic monomers, nucleosides and nucleoside analogues of the invention may be natural or synthetic.

The term "nucleoside analogue" or "analogue nucleoside" as used in the invention means any modified nucleoside, i.e. a compound having a structure analogous to a nucleoside.

Similarly, the term "analogue nucleotide" or "nucleotide analogue" as used in the invention means any modified nucleotide, i.e. having a structural analogy with a nucleotide.

The analogues may thus comprise one or more modifications on the osidic and/or aglycone cycle; the pyrimidine or purine bases may, for example, carry modifications to their heterocycle.

FIG. 1 illustrates certain of these compounds, and $R_1$ to $R_6$ on the oside cycle represents the usual substituents on natural or non natural oside residues. Thus, $R_1$ to $R_6$, independently of each other, may represent H, OH, halogen, an alkyl, O-alkyl, alkenyl, $C_1$ to $C_4$ alkynyl, alkylamino, amine, hydroxylamino, azido, nitro, cyano, or any other substituent capable of forming a modified nucleoside.

In FIG. 1, the nucleoside to be coupled is denoted R'NH$_2$. It is a sugar-base assembly with an exocyclic amine (NH$_2$), and R' represents the sugar-base assembly, without said exocyclic amine NH$_2$ of the base which will be coupled with the soluble support (b).

In the analogue compound modified on the sugar in FIG. 1 (c-3), the base is pyrimidic and in the oside cycle, W may represent CH$_2$, CHX or CX$_2$ (X representing halogen here) to form a carbocycle, when Y and Z are also carbon atoms, but W may also represent O or S, Y and Z representing carbon atoms, or encore W and Z may represent O or S, Y representing CH$_2$, or Y and W may represent O or S, Z representing CH$_2$. The base may carry a halogen, X' preferably representing H or F.

In the modified analogue compound of FIG. 1 (c-4), the base is modified purine, W' can represent CH or CF, and X' then represents H, or representing N; X' then represents F, for example.

The sugar may be a ribose or a deoxyribose or any other analogue of the arabinofuranose type, for example.

More particularly, the continuation of FIG. 1 illustrates the ether-acid case (m"0.1) i.e. a particular case of FIG. 1 (a-3), (a-4) and (b).

The definition of the nucleoside analogues of the invention is thus not limited to just the compounds illustrated in FIG. 1 or by the definitions of X, X', W, W', Y, Z and $R_1$ to $R_6$ given above by way of non-limiting illustration.

The nucleosides or nucleoside analogues used as the starting product in the method of the invention comprise an exocyclic amino or a hydroxyl group which allows them to be coupled to the linker of the soluble support.

Examples of nucleosides comprising bases are, for example, adenosine, guanosine, cytidine. They may also be the corresponding deoxynucleosides deoxyadenosine, deoxyguanosine or deoxycytidine.

The nucleoside analogues may be modified on the base, purine or pyrimidine, and/or on the carbohydrate group (sugar).

More precise examples of nucleosides and nucleoside analogues which are used as starting products are given hereinafter: 3'-O-acetyl-2'-deoxycytidine, allopurinol riboside, 2-amino-6-chloropurine riboside, 2'-deoxyuridine, cytidine, 2'-deoxycytidine, 5-aza-2'-deoxycytidine, 8-azaguanine, 8-bromoguanosine, 8-bromoguanosine, 2-chloroadenosine, 2-chloro-$N^6$-cyclopentyladenosine, 5-chlorocytosine arabinoside, 2-chloro-2'-deoxyadenosine, 5-chloro-2'-deoxyuridine, 6-chloropurine riboside, 2'-deoxyadenosine monohydrate, 2'-deoxycytidine, 2'-deoxyguanosine monohydrate, 3'-deoxyguanosine, 2'-deoxyuridine, 2,6-diaminopurine 2'-deoxyriboside, 2',3'-dideoxyadenosine, 2',3'-dideoxycytidine, 5,6-dihydrodeoxyuridine, 6-(γ,γ-dimethylallylamino) purine riboside, 1,$N^6$-etheno-2'-deoxyadenosine, 5-hydroxymethyl-2'-deoxyuridine, 5-(2-hydroxy-5-nitrobenzyl)-6-thioguanosine, S-(2-hydroxy-5-nitrobenzyl)-6-thioinosine, 5-iodo-2'-deoxycytidine, $N^4$-isobutyryl-2'-deoxycytidine, isocytosine, 2',3'-O-isopropylideneguanosine, 8-mercaptoguanosine, 5-methoxyuridine, 2'-O-methyladenosine, 5-methylcytidine, 2'-O-methylcytidine, 3-methylcytidine methosulphate, $N^6$-methyl-2'-deoxyadenosine, 7-methylguanosine, $N^2$-methylguanosine, 6-methylmercaptopurine riboside, 3'-O-methyluridine, orotic acid, 2-thio-6-azauridine, 4-thiouridine, thymine 1-β-D-arabinofuranoside, uracil 1-β-D-arabinofuranoside, zeatin riboside, 2',3'-dideoxy-3'-thia-β-L-cytidine, 2',3'-dideoxy-3'-thia-β-L-5-fluorocytidine, 9[2-(phosphonylmethoxy) propyl] adenine, 9[2-(phosphonylmethoxy)ethyl] adenine, 1-(β-D-ribofuranosyl)-1H-1,2,4-triazole-3-carboxamide, β-D-2'-C-methyl cytidine, β-D-2'-C-methyl 5-fluorocytidine, β-D-2'-deoxy-2'-fluoro-2'-C-methyl cytidine, β-D-2'-deoxy-2',2'-difluoro cytidine, 7-deaza-β-D-2'-C-methyl adenosine, 7-deaza-7-fluoro-β-D-2'-C-methyl adenosine, 2'-deoxy-β-L-thymidine, 2'-deoxy-β-L-cytidine, 1-(2'-fluoro-β-L-ribofuranosyl)-uracile, 9-(β-D-arabinofuranosyl)-2-fluoro-adenine, 9-(β-D-arabinofuranosyl)-adenine, 1-(β-D-arabinofuranosyl)-cytosine and analogues.

Coupling is carried out using at least one coupling agent which may be selected from a carbodiimide, an aromatic oxime or onium type coupling agents, i.e. for example ammonium, phosphonium or uronium of a nucleophile anion, or analogues thereof.

An example of a carbodiimide which may be cited is dicyclohexylcarbodiimide (DCC) or diisopropylcarbodiimide (DIC).

An example of an aromatic oxime which may be cited is 1-hydroxybenzotriazole (HOBt) or 1-hydroxy-7-aza-benzotriazole (HOAt) and analogues.

An example of an onium, in particular phosphonium, which may be cited is (2-(1H-benzotriazol-1-yl)-1,1,3,3-tetramethyluronium (HBTU) hexafluorophosphate, (2-(7-aza-1H-benzotriazole-1-yl)-1, 1,3,3-tetramethyluronium (HATU) hexafluorophosphate or benzotriazole-1-yl-oxytris-pyrrolidinophosphonium (PyBOP) hexafluorophosphate, and analogues. Another coupling agent is dimethylaminopyridine (DMAP).

The quantities used in the coupling reaction depend on the quantities of nucleosides or analogues employed. In general, for 1 to 5 eq of nucleoside, 1 to 10 equivalent of coupling agent is used. It is also possible to use 1 to 2 eq of nucleoside, and 1 to 4 eq of coupling agent.

In general, one equivalent of soluble support comprising one or two linkers is coupled to one or two equivalents of nucleoside or analogue.

The term "nucleotide" as used here means monomers constituted by a heterocycle and a sugar and at least one phosphorylated group. The nucleotides produced using the method of the present application include mono-, di- or triphosphate nucleosides. The nucleotides may thus be natural or synthetic.

At the end of the phosphorylation step or steps described below, and after cleavage, in accordance with the invention nucleotides and nucleotide analogues modified on the sugar or the base are obtained, as were the starting nucleosides or nucleoside analogues, and also nucleotides which could be modified on one or more phosphates.

As an example, the base-modified nucleotide analogues may be as follows: 2'-deoxyinosine 5'-triphosphate, 2-amino-2-deoxyadenosine 5'-triphosphate, 5-aminoallyl-2'-deoxycytidine 5'-triphosphate, 5-fluorocytidine 5'-monophosphate, 2-fluoroadenosine 5'-monophosphate, 5-iododeoxyuridine 5'-triphosphate, 5-trifluoromethylthymidine 5'-triphosphate, 5-(2-chloroethyl) deoxyuridine 5'-triphosphate, 5-ethyldeoxyuridine 5'-triphosphate, (E)-5-(2-bromovinyl) deoxyuridine 5'-triphosphate, 5-fluorodeoxyuridine 5'-triphosphate, 6-thiopurine riboside 5'-triphosphate, 2-chlorodeoxyadenosine 5'-triphosphate, 5-azacytidine 5'-triphosphate, 3-deazauridine 5'-triphosphate, thiazofurine 5'-triphosphate, ribavirine 5'-triphosphate, allopurinol riboside 5'-triphosphate, Formycin B 5'-triphosphate, 8-bromoguanosine 5'-triphosphate, 8-mercaptoguanosine 5'-triphosphate, 7-methyl-8-oxoguanosine 5'-triphosphate, 7-thia-8-oxoguanosine 5'-triphosphate, and analogues.

Examples of triphosphate nucleosides modified on the sugar portion are as follows: 2',3'-dideoxyadenosine 5'-triphosphate, 2',3'-deoxycytidine 5'-triphosphate, 2' amino-2'-deoxyadenosine 5'-triphosphate and analogues.

Examples of nucleotide analogues modified both on the base and on the oside residue are as follows: arabinosyl-5-azacytosine 5'-triphosphate, 2-fluoroarabinofuranosyladenosine 5'-triphosphate, 1-(beta-L-ribofuranosyl)-2-isopropylamino-5,6-dichlorobenzimidazole 5'-triphosphate, 7-deaza-2'-C-methyladenosine 5'-triphosphate, 2-amino-9-beta-D-arabinofuranosyl-6-methoxy-9H-purine 5'-triphosphate, 1-(beta-L-2-fluoro-2-deoxyarabinofuranosyl)-5-methyluracil 5'-triphosphate.

Examples of nucleosides modified on the phosphate are as follows: 2',3'-dideoxyadenosine 5'-O-(1-thiotriphosphate), 2',3'-dideoxycytidine-5'-O-(1-thiotriphosphate), 2',3'-dideoxyguanosine-5'-O-(1-thiotriphosphate), 2'-deoxyadenosine-5'-O-(1-thiotriphosphate), 2'-deoxycytidine-5'-O-(1-thiotriphosphate), 2'-deoxyguanosine-5'-O-(1-thiotriphosphate), 2'-deoxythymidine-5'-O-(1-thiotriphosphate), adenosine-5'-O-(1-thiotriphosphate), cytidine-5'-O-(1-thiotriphosphate), guanosine-5'-O-(1-thiotriphosphate), cyclic adenosine 3',5' monophosphate and analogues.

The synthesis of the corresponding monophosphates and diphosphates is also possible in accordance with the invention, as will be seen below, and in the examples.

Starting from a nucleoside or analogue fixed on the soluble support, the nucleoside is mono-, di- or tri-phosphorylated in one or two or three phosphorylation steps.

As will be seen in FIG. 2, in order to obtain a monophosphate, monophosphorylation (e) is carried out.

In order to obtain a diphosphated monomer, diphosphorylation is carried out. This may be carried out directly in a single step with a diphosphorylating agent (d) or in two successive monophosphorylation steps (e) then (g), the second monophosphorylation step (g) possibly being activated.

In order to obtain a triphosphated monomer, triphosphorylation is carried out. This can be achieved by diphosphorylation (d) with a diphosphorylating agent then monophosphorylation or by monophosphorylation (e) followed by a diphosphorylation (f) or followed by two successive monophosphorylations (g).

Preferably, the second phosphorylations are activated.

In order to carry out the phosphorylation, a phosphorylation agent is used. Depending on the nature and reactivity of this agent, prior activation may be necessary.

For monophosphorylation of the nucleoside on polymer support, a phosphorus oxychloride type phosphorylation agent is added to a solution of nucleoside on polymer support in a suitable solvent, and the supported monophosphate nucleoside is extracted and/or isolated by precipitation.

In order to phosphorylate the monophosphate nucleoside on a polymer support, supported monophosphate nucleoside is dissolved in an appropriate solvent, activated then brought into the presence of a phosphorylation agent of the tributylammonium phosphate type and the expected compound is precipitated.

In order to dephosphorylate a monophosphate nucleoside on polymer support, the monophosphate nucleoside on polymer, support is activated in an appropriate solvent then brought into the presence of a tributylammonium pyrophosphate type phosphorylation agent and the expected product precipitates out.

The phosphorylation agents may be selected from compounds of the type $Z'=PX^1_3$, where Z' is O, S or Se, for monophosphorylation, or for diphosphorylation, $W^1[(P=Z')X^1]_2$ where $W^1$ is O, NH, $CH_2$, CHOH, $CHNH_2$, $CHCH_3$, $CHX^2$ or $CX^2_2$ and Z' is O, S or Se, with $X^1$ and $X^2$ representing halogen, or suitable analogues.

Other phosphorylation agents $Z'=P(O^-)_3$ and $W^1[(P=O)(O^-)_2]_2$ where $W^1$ and Z' have the meanings given above which are capable of mono- and diphosphorylation are less effective and may necessitate activation of the nucleoside or nucleic analogue.

Phosphorylation agents which may in particular be cited are derivatives of phosphorus (III) or derivatives of phosphorus (V). Examples of appropriate phosphorylation agents of the phosphorus oxychloride type for monophosphorylation are selected from phosphorus oxychloride, thiophosphate trichloride, 4-nitrophenyl dichlorophosphate, O-(2-chlorophenyl) dichlorothiophosphate, aminomethyl phosphonic acid, aminomethyl (methyl) phosphonic acid, 2-chloro-1,3,2-dioxaphospholane, 2-chloro-2-oxo-1,3,2-dioxaphospholane, 2-chloro-4H-1,3,2-benzodioxaphosphorin-4-one, barium 2-cyoanoethylphosphate, diethylchlorothiophosphate, dimethylchlorothiophosphate, methylphosphorodichloridate, phenyldichlorophosphate, methyldichlorophosphite and diphenylphosphite and analogues and also 2-chlorophenylphosphorodichloridate, 4-chlorophenylphosphorodichloridate, diphenyl-chlorophosphate and dibenzyl-N,N-diisopropylphosphoramidite. Preferred substances in accordance with the invention are phosphorus oxychloride, thiophosphate trichloride, 4-nitrophenyl dichlorophosphate, tributylammonium phosphate and diphenylphosphite.

Diphosphorylation agents of the tributylammonium pyrophosphate type which may be cited are etidronic acid, imidodiphosphate salts, imino di(methyl phosphonic acid), pyrophosphoryl tetrachloride, methyl bis(dichlorophosphonate) and methylene bisphosphonic acid. Preferred substances in accordance with the invention are tributylammonium pyrophosphate and methylene bisphosphonic acid.

The quantities of phosphorylation agents used depend on their reactivity. In general, 10 to 30 equivalents of phosphorylation agents are used for 1 to 2 equivalents of nucleoside coupled to a support, preferably 15 to 30 equivalents of phosphorylation agents.

Examples of activation agents which may be cited are mesitylsulphonylnitrotriazole (MSNT), mesitylsulphonyltriazole (MST), mesitylsulphonyl chloride (MSCl), tri-isopropylsulphonyl chloride (TPSCI), the $Tf_2O$/dimethylaminopyridine (DMAP) system, 1,1-carbonyldiimidazole (CDI) and the like. The activation agents are used in quantities of the order of 1 to 10 equivalents, preferably 3 to 6 equivalents.

In a subsequent phosphorylation step, the soluble support may be dissociated from the nucleotide or the nucleotide analogue obtained, this being carried out using a cleavage agent.

Any base or any nucleophile may be used as a cleavage agent. Examples which may be used are ammonia, sodium hydroxide, sodium methylate, ammoniacal methanol or potassium cyanide or the like.

In accordance with the invention, in general, an excess of base is used.

The nucleotides cleaved from their support as produced by the method of the present application may then be isolated using any method known in the art. Liquid chromatography (LC) or HPLC may be used, for example on a reverse phase column.

They may also be purified by dialysis, in particular when the residue from cleavage has not already been eliminated. Dialysis may be carried out using any suitable method, for example on a cellulose ester methyl.

In general, for bifunctional linkers of the succinate type, the cleaved linker separates with the substrate and the support. This may render dialysis advantageous for purification. Thus, the compound from hydrolysis of the linker may contaminate the substrate and dialysis may then be envisaged as a purification step. In contrast, for ether-acid type linkers, the linkers remain on the PEG support, and so dialysis may not be necessary.

After the mono-, di- or tri-phosphorylation step (or steps), in particular in the case of PEG-O(CH$_2$)$_2$—COOH, cleavage of the linker can produce the expected nucleotide directly after elimination of the polymeric support, without having to carry out dialysis.

Thus, as will become apparent in the examples, using PEG functionalized with a linker corresponding to 3-hydroxypropanoic acid (PEG-O(CH$_2$)$_2$—COOH) can simplify the procedure, as the dialysis step can be dispensed with.

As indicated above, the nucleotides and analogues obtained may be used as effectors, biological tools for research, diagnostics or any therapeutic or pre-clinical application.

Although the invention has been described here in terms of preferred modes, the specialist will appreciate that equivalents, modifications, substitutions, omissions or variations are possible without departing from the scope of the invention.

EXAMPLE 1

Polyethylene glycol-bis-succinate, PEG$_{4000}$-bis-succinate

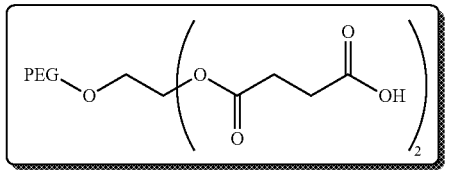

20 g (4.76 mmole) of PEG$_{4000}$ was co-evaporated with anhydrous pyridine and dissolved in 160 mL of pyridine. 5 g (49.90 mmole) of succinic anhydride and 0.30 g (2.49 mmole) of dimethylaminopyridine were added and the mixture was stirred for two days at ambient temperature. The solution was concentrated under reduced pressure, co-evaporated with toluene and dissolved in a minimum of dichloromethane. The brown precipitate formed was eliminated by filtration. The filtrate was concentrated under reduced pressure and dissolved in a dichloromethane/N,N-dimethylformamide (3/7, v/v) mixture. The PEG bis-succinate was precipitated by adding an excess of cold diethyl ether. The precipitate was filtered, washed with diethyl ether and vacuum dried over KOH pellets to produce PEG bis-succinate in the form of a white solid (18.14 g, 86%).

$^1$H NMR (CDCl$_3$, 400 MHz) δ 4.18 (m, 2H, (OCH$_2$α)$_{PEG}$), 3.40-3.75 (m, (OCH$_2$)$_{PEG}$), 2.57 (s, 4H, CH$_{2succ}$).

$^{13}$C NMR (CDCl$_3$, 100 MHz) δ 173.9, 172.2 (s, C=O$_{succ}$), 70.5 (s, (OCH$_2$)$_{PEG}$), 68.9 (s, (OCH$_2$β)$_{PEG}$), 64.2 (s, (OCH$_2$α)$_{PEG}$), 29.3, 28.9 (s, CH$_{2succ}$).

EXAMPLE 2

Poly(oxyethylene)$_{4000}$ bis(2-hydroxyacetic acid)

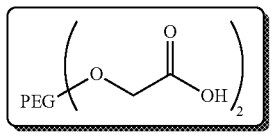

1 g of PEG$_{4000}$ (0.25 mmole) was dissolved in 10 mL of acetone and 0.85 mL of Jones reagent (1 mmole of CrO$_3$) was added. When addition was complete, the blue-green chromium salts precipitated out of the reaction medium. The mixture was stirred at ambient temperature for 16 h. The reaction was stopped by adding 0.15 mL of isopropanol and 0.10 g of activated charcoal, and stirring was continued for 3 h. The activated charcoal was then eliminated by filtration through a Buckner funnel and the filtrate was concentrated under reduced pressure. The residue was dissolved in a minimum of dichloromethane and precipitated by addition of an excess of cold diethyl ether. The precipitate was filtered, washed with diethyl ether, then vacuum dried over KOH pellets to produce the expected product in the form of a white solid (3.26 g, 81%).

IR 1643 cm$^{-1}$ (COOH), 3418 cm$^{-1}$ (OH).
$^{13}$C NMR (CDCl$_3$, 75 MHz) δ 171.6 (s, C=O), 70.8 (s, (OCH$_2$α)$_{PEG}$), 70.4 (s, (OCH$_2$)$_{PEG}$), 68.5 (s, (OCH$_2$COOH)$_{PEG}$).

EXAMPLE 2 bis: Poly(oxyethylene)$_{4000}$ bis(2-hydroxypropanoic acid)

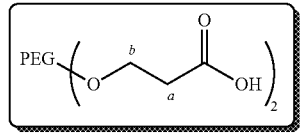

A solution of 1 g of PEG$_{4000}$ (2.5 mmole, 1 eq.) and potassium tert-butoxide (0.25 mmole, 0,1 eq.) in toluene (25 mL) was stirred at 40° C. for 20 minutes, and tert-butylacrylate (15 mmole, 6 eq.) was added The mixture was stirred at 40° C. for 6 h. The solvent was eliminated by evaporation under reduced pressure. The residue obtained was dissolved in dichloromethane (100 mL) and this solution was slowly added to an excess of cold diethyl ether (1 L). The precipitate was filtered, washed with diethyl ether several times, then vacuum dried over KOH pellets overnight.

The PEG-bis(O—CH$_2$)$_2$—COOtBu) was dissolved in dichloromethane (20 mL), an equal volume of TFA (trifluoroacetic acid) was added and the mixture was stirred at ambient temperature overnight.

The solvents were evaporated off under reduced pressure, the resulting oil was dissolved in dichloromethane (100 ml), and this solution was slowly added to an excess of cold diethyl ether (1 L). The precipitate was filtered, washed with diethyl ether several times, then vacuum dried over KOH pellets overnight. The final product, PEG-bis(OCH$_2$CH$_2$—COOH), was obtained in the form of a white solid (8.63 g, 83%).

$^1$H NMR (CDCl$_3$, 300 MHz) δ 3.87-3.42 (m, (OCH$_2$)$_{PEG}$), 2.60 (t, 2H, CH$_2$a).
$^{13}$C NMR (CDCl$_3$, 75 MHz) δ 173.0 (s, C=O), 70.5 (s, (OCH$_2$)$_{PEG}$), 66.9 (s, CH$_2$b), 34.7 (s, CH$_2$a).

EXAMPLE 3

Method A: Coupling of Bifunctionalized PEG and Nucleoside

A solution of nucleoside or nucleoside analogue (2 eq.) in N,N-dimethylformamide (30 mL) was added to a solution of PEG comprising two linkers (0.95 mmole, 1 eq), for example PEG bis-succinate, in dichloromethane (70 mL). N,N-dicyclohexylcarbodiimide (3.79 mmole, 4 eq) and N-hydroxybenzotriazole (1.89 mmole, 2 eq) were added and the resulting mixture was stirred at 60° C. for 7 h. The solvents were evaporated off under reduced pressure and the residue obtained was dissolved in a minimum of dichloromethane and allowed to rest overnight at 4° C. The precipitated dicyclohexylurea was separated by filtration. The filtrate was concentrated under reduced pressure and dissolved in N,N-dimethylformamide (40 mL). The resulting solution was slowly eliminated with an excess volume of cold diethyl ether. The precipitate was filtered and washed with diethyl ether. The final product was recrystallized from absolute ethyl alcohol (40 mL) and vacuum dried over KOH pellets.

EXAMPLE 4

Poly(ethyleneglycol)$_{4000}$ bis[4-N-(1-(β-D-arabinofuranosyl)-cytosyl) succinate]

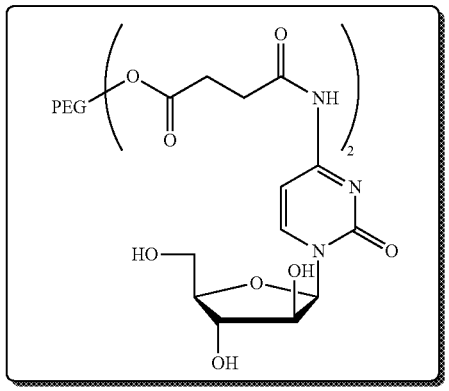

Coupling between PEG-bis-succinate (4 g, 0.95 mmole) and the nucleoside araC (0.46 g, 1.89 mmole) was carried out using method A of Example 3. The compound was obtained in the form of a white solid (3.65 g, 83%).

$R_f$(CH$_2$Cl$_2$/MeOH, 7/3, v/v): 0.7.

$^1$H NMR (D$_2$O, 200 MHz) δ 8.16 (d, J$_{6-5}$=7.5 Hz, 1H, H$_6$), 7.26 (d, J$_{5-6}$=7.5 Hz, 1H, H$_5$), 6.10 (d, J$_{1'-2'}$=4.6 Hz, 1H, H$_{1'}$), 4.34 (t, J$_{2'-1'}$=J$_{2'-3'}$=4.6 Hz, 1H, H$_{2'}$), 4.16 (m, 2H, (OCH$_2$α)$_{PEG}$), 4.02-3.92 (m, 2H, H$_{3'}$, H$_{4'}$), 3.73 (m, 2H, 2H$_{5'}$), 3.70-3.33 (m, (OCH$_2$)$_{PEG}$), 2.76-2.62 (m, 4H, CH$_{2succ}$).

$^{13}$C NMR (D$_2$O, 75 MHz) δ 174.6, 174.5 (2s, C=O$_{succ}$), 162.5 (s, C$_4$), 156.7 (s, C$_2$), 146.7 (s, C$_6$), 97.3 (s, C$_5$), 87.1 (s, C$_{1'}$), 84.0 (s, C$_{4'}$), 75.4 (s, C$_{2'}$), 75.2 (s, C$_{3'}$), 69.6 (s, (OCH$_2$)$_{PEG}$), 68.4 (s, (OCH$_2$β)$_{PEG}$), 64.1 (s, (OCH$_2$α)$_{PEG}$), 60.7 (s, C$_{5'}$), 31.5, 28.5 (2s, CH$_{2succ}$).

EXAMPLE 5

Poly(ethyleneglycol)$_{4000}$ bis[4-N-(1-(2'-deoxy-(β-D-ribofuranosyl)-cytosyl) succinate]

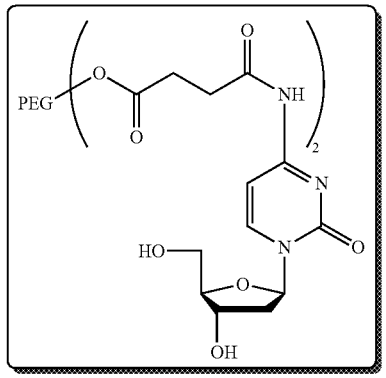

Coupling between PEG-bis-succinate (4.84 g, 1.15 mmole) and 2'-deoxycytidine (0.52 g, 2.30 mmole) was carried out using method A of Example 3. The compound was obtained in the form of a white solid (4.60 g, 87%).

$R_f$(CH$_2$Cl$_2$/MeOH, 6/4, v/v): 0.9.

$^1$H NMR (D$_2$O, 300 MHz) δ 8.25 (d, J$_{6-5}$=7.5 Hz, 1H, H$_6$), 7.27 (d, J$_{5-6}$=7.5 Hz, 1H, H$_5$), 6.13 (t, J$_{1'-2'a}$=J$_{1'-2'b}$=6.2 Hz, 1H, H$_{1'}$), 4.30 (m, 1H, H$_{3'}$), 4.19 (m, 2H, (OCH$_2$α)$_{PEG}$), 4.04 (m, 1H, H$_{4'}$), 3.85-3.50 (m, 2H$_{5'}$, (OCH$_2$)$_{PEG}$), 2.80-2.65 (m, 4H, CH$_{2succ}$), 2.43 (m, 1H, H$_{2'a}$), 2.23 (m, 1H, H$_{2'b}$).

$^{13}$C NMR (D$_2$O, 100 MHz) δ 174.5, 174.4 (2s, C=O$_{succ}$), 162.4 (s, C$_4$), 156.7 (s, C$_2$), 145.5 (s, C$_6$), 97.7 (s, C$_5$), 87.4 (s, C$_{1'}$), 87.3 (s, C$_{4'}$), 70.2 (s, C$_{3'}$), 69.6 (s, (OCH$_2$)$_{PEG}$), 68.4 (s, (OCH$_2$β)$_{PEG}$), 64.1 (s, (OCH$_2$α)$_{PEG}$), 61.0 (s, C$_{5'}$), 40.1 (s, C$_{2'}$), 31.5, 28.4 (2s, CH$_{2succ}$).

EXAMPLE 6

Poly(ethyleneglycol)$_{4000}$ bis[4-N-(1-(β-D-ribofuranosyl)-cytosyl) succinate]

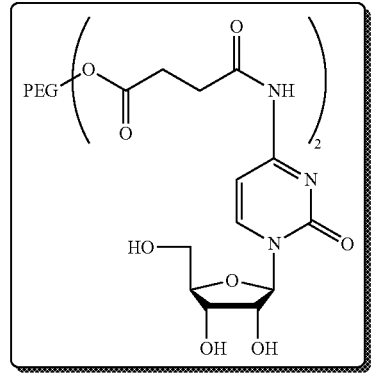

Coupling between PEG-bis-succinate (5 g, 1.20 mmole) and cytidine (0.58 g, 2.4 mmole) was carried out using method A of Example 3 and the compound was obtained in the form of a white solid (4.80 g, 87%).

$R_f$(CH$_2$Cl$_2$/MeOH, 6/4, v/v): 0.9.

$^1$H NMR (D$_2$O, 200 MHz) δ 8.26 (d, J$_{6-5}$=7.5 Hz, 1H, H$_6$), 7.26 (d, J$_{5-6}$=7.5 Hz, 1H, H$_5$), 5.79 (d, J$_{1'-2'}$=2.7 Hz, 1H, H$_{1'}$), 4.19-4.14 (m, 2H, (OCH$_2$α)$_{PEG}$), 4.06 (d, J$_{2'-1'}$=2.7 Hz, 1H, H$_{2'}$), 3.98-3.25 (m, H$_{3'}$, H$_{4'}$, 2H$_{5'}$, (OCH$_2$)$_{PEG}$), 2.64-2.76 (m, 4H, CH$_{2succ}$).

$^{13}$C NMR (D$_2$O, 100 MHz) δ 174.6, 174.5 (2s, C=O$_{succ}$), 162.6 (s, C$_4$), 156.9 (s, C$_2$), 145.6 (s, C$_6$), 97.8 (s, C$_5$), 91.3 (s, C$_{1'}$), 83.8 (s, C$_{4'}$), 74.5 (s, C$_{3'}$), 69.5 (s, (OCH$_2$)$_{PEG}$), 68.6 (s, C$_{2'}$), 68.4 (s, (OCH$_2$β)$_{PEG}$), 64.1 (s, (OCH$_2$α)$_{PEG}$), 60.1 (s, C$_{5'}$), 31.5, 28.4 (2s, CH$_{2succ}$).

EXAMPLE 7

Poly(ethyleneglycol)$_{4000}$ bis[4-N-(1-(2',3'-dideoxy-β-D-ribofuranosyl)cytosyl) succinate]

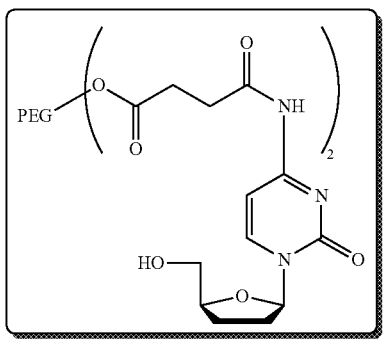

Coupling between 0.25 g of PEG-bis-succinate (0.06 mmole) and 0.025 g of 2',3'-dideoxycytidine (0.12 mmole) was carried out using method A of Example 3. The compound was obtained in the form of a white solid (0.23 g, 87%).

R$_f$ (CH$_2$Cl$_2$/MeOH, 8/2, v/v): 0.8.

$^1$H NMR (D$_2$O, 300 MHz) δ 8.33 (d, J$_{6-5}$=7.5 Hz, 1H, H$_6$), 7.26 (d, J$_{5-6}$=7.5 Hz, 1H, H$_5$), 5.97 (dd, J$_{1'-2'a}$=6.6 Hz, J$_{1'-2'b}$=2.0 Hz, 1H, H$_{1'}$), 4.20 (m, 3H, (OCH$_2$α)$_{PEG}$ H$_{4'}$), 3.86-3.81 (m, 2H, 2H$_{5'}$), 3.73-3.62 (m, OCH$_2$)$_{PEG}$), 2.79-2.65 (m, 4H, CH$_{2succ}$), 2.45 (m, 1H, H$_{2'a}$), 2.05 (m, 1H, H$_{2'b}$), 1.97 (m, 1H, H$_{3'a}$), 1.65 (m, 1H, H$_{3'b}$).

$^{13}$C NMR (D$_2$O, 100 MHz) δ 174.6, 174.5 (2s, C=O$_{succ}$), 162.4 (s, C$_4$), 156.9 (s, C$_2$), 145.7 (s, C$_6$), 97.4 (s, C$_5$), 88.3 (s, C$_{1'}$), 83.3 (s, C$_{4'}$), 69.6 (s, (OCH$_2$)$_{PEG}$), 68.4 (s, (OCH$_2$β)$_{PEG}$), 64.1 (s, (OCH$_2$α)$_{PEG}$), 62.3 (s, C$_{5'}$), 32.5 (s, C$_{2'}$), 31.5, 28.5 (2s, CH$_{2succ}$), 24.1 (s, C$_{3'}$).

EXAMPLE 8

Poly(ethyleneglycol)$_{4000}$ bis[4-N-(1-(2',3'-dideoxy-3'-thia-(β-D-ribofuranosyl)-cytosyl) succinate]

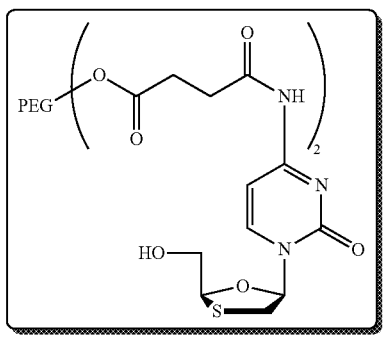

Coupling between 1 g of PEG-bis-succinate (0.23 mmole) and 0.10 g of 3TC (0.47 mmole) was carried out using method A of Example 3. The compound was obtained in the form of a white solid (0.88 g, 80%).

R$_f$ (CH$_2$Cl$_2$/MeOH, 8/2, v/v): 0.8.

$^1$H NMR (D$_2$O, 300 MHz) δ 8.42 (d, J$_{6-5}$=7.5 Hz, 1H, H$_6$), 7.25 (d, J$_{5-6}$=7.5 Hz, 1H, H$_5$), 6.24 (dd, J$_{1'-2'a}$=2.7 Hz, J$_{1'-2'b}$=5.4 Hz, 1H, H$_{1'}$), 5.31 (t, J$_{4'-5'}$=3.6 Hz, 1H, H$_{4'}$), 4.20- 4.17 (m, (OCH$_2$α)$_{PEG}$), 3.99 (dd, J$_{5'a-4'}$=3 Hz, J$_{5a'-5'b}$=12.9 Hz, 1H, H$_{5'a}$), 3.90-3.34 (m, OCH$_2$)$_{PEG}$ H$_{5'b}$ H$_{2'a}$), 3.22 (dd, J$_{2'b-1'}$=2.4 Hz, J$_{2'b-2'a}$=12.6 Hz, 1H, H$_{2'b}$), 2.79-2.65 (m, 4H, CH$_{2succ}$).

$^{13}$C NMR (D$_2$O, 100 MHz) δ 174.6, 174.5 (2s, C=O$_{succ}$), 162.6 (s, C$_4$), 156.6 (s, C$_2$), 146.1 (s, C$_6$), 97.3 (s, C$_5$), 88.0 (s, C$_{1'}$), 87.9 (s, C$_{4'}$), 69.6 (s, (OCH$_2$)$_{PEG}$), 68.4 (s, (OCH$_2$β)$_{PEG}$), 64.1 (s, (OCH$_2$α)$_{PEG}$), 61.5 (s, C$_{5'}$), 38.0 (s, C$_{2'}$), 31.5, 28.5 (2s, CH$_{2succ}$).

EXAMPLE 8 bis: Poly (oxyethylene)$_{4000}$ bis[6-N-(1-(2'-deoxy-3',5'-O-((tetraisopropyl)disiloxane-1,3-diyl)-8-D-ribofuranosyl)-adenosyl) succinate

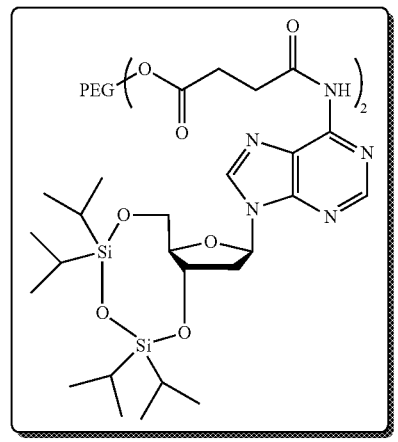

Coupling between PEG bis-succinate (1 g, 0.24 mmole) and 2'-deoxyadenosine (0.24 g, 0.48 mmole) was carried out using method A, and PEG-O-bis(succinyl-3',5'-TIPS, 2' dA) was obtained in the form of a white solid (0.95 g, 78%).

R$_f$ (dichloromethane/methanol 98/2): 0.57

$^1$H NMR (CDCl$_3$, 300 MHz) δ 8.74 (s, 1H, NH), 8.58 (s, 1H, H$_8$), 8.13 (s, 1H, H$_2$), 6.25 (m, 1H, H$_{1'}$), 4.90 (m, 1H, H$_{3'}$), 4.20 (m, 2H, (OCH$_2$α)$_{PEG}$), 4.12 (m, 3H, H$_{4'}$ 2H$_{5'}$), 3.85-3.32 (m, (OCH$_2$)$_{PEG}$), 3.19 (m, 2H, CH$_{2succ}$), 2.72 (m, 2H, CH$_{2succ}$), 2.61 (m, 2H, H$_{2'}$), 0.962 (m, 28H, ((CH$_3$)$_2$CH)$_4$).

EXAMPLE 8 ter: Poly (oxyethylene)$_{4000}$ bis[6-N-(1-(2-deoxy-β-D-ribofuranosyl)-adenosyl) succinate

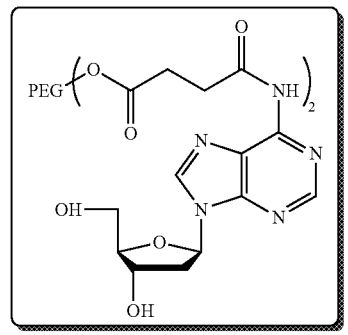

PEG-O-bis(succinyl-3',5'-TIPS, 2'dA) (0.21 mmole, 1 eq.) was dissolved in tetrahydrofuran (10 mL), and 1.06 mL of TBAF, tetrabutylammonium fluoride, (1 M TBAF solution in 5 eq tetrahydrofuran) was added to this solution. The resulting mixture was stirred for 1 h, at ambient temperature. The reaction mixture was diluted in dichloromethane (3 mL) and the organic phase was washed with water and brine. After evaporation under reduced pressure, the residue was dissolved in dichloromethane (2 ml) and slowly added to an excess volume of cold diethyl ether (20 mL). The precipitate was filtered and washed with diethyl ether. The final product was re-crystallized in absolute ethanol (2 mL) and vacuum dried over KOH pellets. The product, PEG-O-bis(succinyl-2' dA), was obtained in the form of a white solid (0.82 g, 90%).

$R_f$ (dichloromethane/methanol 98/2): 0.43

$^1$H NMR (CDCl$_3$, 300 MHz) δ 9.15 (s, 1H, NH), 8.63 (s, 1H, H$_8$), 8.19 (s, 1H, H$_2$), 6.41 (m, 1H, H$_{1'}$), 4.73 (m, 1H, H$_{3'}$), 4.22 (m, 4H, 2H$_{5'}$ (OCH$_2$α)$_{PEG}$), 3.98 (m, 1H, H$_{4'}$), 3.86-3.39 (m, (OCH$_2$)$_{PEG}$), 3.22 (m, 2H, CH$_{2succ}$), 2.96 (m, 1H, 1H$_{2'}$), 2.80 (m, 2H, CH$_{2succ}$), 2.61 (m, 2H, CH$_{2succ}$), 2.37 (m, 1H, 1H$_{2'}$).

EXAMPLE 9

Poly(oxyethylene)-4000 bis[4-N-(1-β-D-arabino-furanosyl)-cytosyl) 2-hydroxyacetamide]

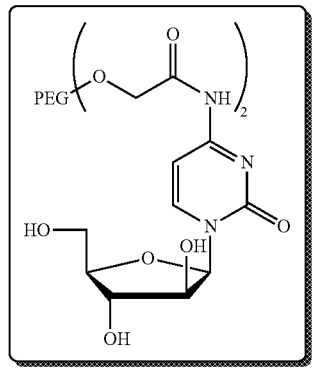

Coupling between 0.5 g of PEG-bis(OCH$_2$—COOH) (0.12 mmole) and 0.06 g of araC (0.24 mmole) was carried out using method A of Example 3. The compound was obtained in the form of a white solid (0.46 g, 82%).

$R_f$ (CH$_2$Cl$_2$/MeOH, 6.5/3.5, v/v): 0.9

$^1$H NMR (D$_2$O, 300 MHz) δ 8.22 (d, J$_{6-5}$=7.0 Hz, 1H, H$_6$), 7.32 (d, J$_{5-6}$=7.0 Hz, 1H, H$_5$), 6.14 (s, 1H, H$_{1'}$), 4.38 (m, 1H, H$_{2'}$), 4.22 (m, 2H, (OCH$_2$COOH)$_{PEG}$), 4.05 (m, 3H, H$_{3'}$ (OCH$_2$α)$_{PEG}$), 4.05-3.20 (m, H$_{4'}$ 2H$_{5'}$(OCH$_2$)$_{PEG}$).

$^{13}$C NMR (D$_2$O, 100 MHz) δ 172.3 (s, C=O), 162.1 (s, C$_4$), 156.5 (s, C$_2$), 147.0 (s, C$_6$), 97.3 (s, C$_5$), 87.2 (s, C$_{1'}$), 84.3 (s, C$_{4'}$), 75.5 (s, C$_{2'}$), 75.2 (s, C$_{3'}$), 70.6 (s, (OCH$_2$α)$_{PEG}$), 70.0 (s, (OCH$_2$)$_{PEG}$), 60.5 (s, OCH$_2$COOH)$_{PEG}$), 60.4 (s, C$_{5'}$).

EXAMPLE 9 bis: Poly (oxyethylene)$_{4000}$ bis[4-N-(1-(β-D-arabino-furanosyl)-cytosyl)-3-hydroxy propanamide]

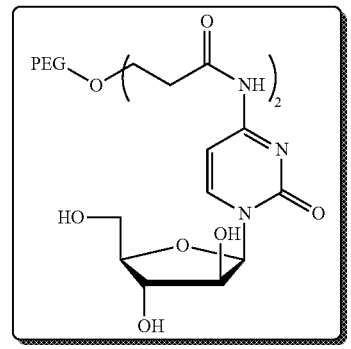

Coupling between PEG-bis(OCH$_2$CH$_2$—COOH) (3 g, 0.72 mmole) and araC (0.35 g, 1.44 mmole) was carried out using method A, and the compound was obtained in the form of a white solid (2.40 g, 72%).

$R_f$ (CH$_2$Cl$_2$/MeOH, 85/15, v/v): 0.7

$^1$H NMR (CDCl$_3$, 300 MHz) δ 8.30 (d, J$_{6-5}$=7.2 Hz, 1H, H$_6$), 7.16 (d, J$_{5-6}$=7.2 Hz, 1H, H$_5$), 6.09 (t, J$_{1'-2'a}$=J$_{1'-2'b}$=5.4 Hz, 1H, H$_{1'}$), 4.46 (m, 1H, H$_{2'}$), 4.32 (m, 1H, H$_{3'}$), 4.14 (m, 1H, H$_{4'}$), 3.97-3.40 (m, 2H$_5$(OCH$_2$)$_{PEG}$), 2.69 (m, 2H, CH$_2$b).

EXAMPLE 9 ter: Poly (oxyethylene)$_{4000}$ bis[4-N-(1-(2'-deoxy-β-D-ribofuranosyl)-cytosyl)-3-hydroxy propanamide]

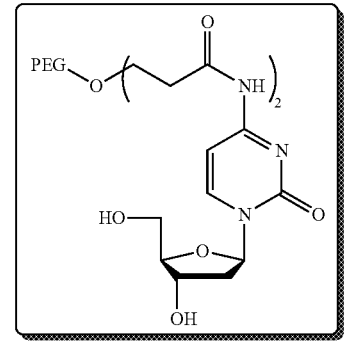

Coupling between PEG-bis(OCH$_2$CH$_2$—COOH) (3 g, 0.72 mmole) and 2'-deoxycytidine (0.33 g, 1.44 mmole) was carried out using method A, and the compound was obtained in the form of a white solid (2.75 g, 83%).

$R_f$ (CH$_2$Cl$_2$/MeOH, 85/15, v/v): 0.8

$^1$H NMR (CDCl$_3$, 300 MHz) δ 8.42 (d, J$_{6-5}$=7.5 Hz, 1H, H$_6$), 7.38 (d, J$_{5-6}$=7.5 Hz, 1H, H$_5$), 6.16 (t, J$_{1'-2'a}$=J$_{1'-2'b}$=6.2 Hz, 1H, H$_{1'}$), 4.50 (m, 1H, H$_{3'}$), 4.11 (m, 1H, H$_{4'}$), 3.85-3.50 (m, 2H$_{5'}$, (OCH$_2$)$_{PEG}$), 3.39 (t, JCH$_{2a}$-CH$_{2b}$=4.5 Hz, 2H, CH$_2$a), 2.54 (m, 1H, H$_{2'a}$), 2.32 (m, 1H, H$_{2'b}$).

EXAMPLE 10

Method B: Monophosphorylation of Nucleoside on Polymer Support

Excess phosphorus oxychloride was added to a solution of PEG-O-bis(succinyl-nucleoside) or PEG-bis(OCH$_2$CH$_2$—CO-nucleoside), i.e. the nucleoside on polymer support (1 eq), in triethylphosphate (6 mL), heated to 40° C. or in acetonitrile at 5° C., and the mixture was stirred for 1 h. The excess phosphorus oxychloride was hydrolyzed by addition of a buffer solution of aqueous triethylammonium bicarbonate (1M, pH=7) (25 mL) and the mixture was concentrated under reduced pressure. The residue was dissolved in dichloromethane (180 mL) and the organic phase was washed with water. The aqueous phase underwent several extractions with dichloromethane. The organic phases were combined and evaporated under reduced pressure. The supported monophosphate was precipitated from a solution of dichloromethane, by addition of an excess of cold diethyl ether. The precipitated was filtered, washed with diethyl ether and vacuum dried over KOH.

EXAMPLE 11

Poly(ethyleneglycol)$_{4000}$ Bis[4-N-(1-(β-D-arabino-furanosyl)-cytosyl-5'-monophosphate) succinate], tri-ethylammonium salts

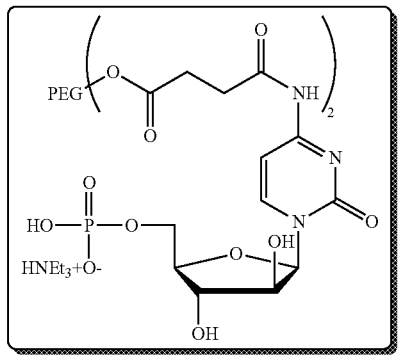

Monophosphorylation of 3 g (0.64 mmole) of PEG-O-bis(succinyl-araC) from Example 4 was carried out using method B of Example 10 to produce the compound in the form of a white solid (2.99 g, 92%).

HPLC tr$_{araCMP}$: 18.9 min tx$_{monophosphorylation}$: 97%.

$^1$H NMR (D$_2$O, 300 MHz) δ 8.34 (d, J$_{6-5}$=7.5 Hz, 1H, H$_6$), 7.10 (d, J$_{5-6}$=7.5 Hz, 1H, H$_5$), 6.18 (d, J$_{1'-2'a}$=5.0 Hz, 1H, H$_{1'}$), 4.42 (m, 1H, H$_{2'}$), 4.19 (m, 2H, (OCH$_2$α)$_{PEG}$), 4.10-4.15 (m, 4H, H$_{3'}$, H$_{4'}$ 2H$_{5'}$), 3.30-3.90 (m, (OCH$_2$)$_{PEG}$), 3.10 (q, J=7.3 Hz, 6H, (CH$_3$CH$_2$)$_3$NH), 2.62-2.85 (m, 4H, CH$_{2succ}$), 1.18 (t, J=7.3 Hz, 9H, (CH$_3$CH$_2$)$_3$NH).

$^{13}$C NMR (D$_2$O, 100 MHz) δ 174.7, 174.4 (s, C=O$_{succ}$), 159.0 (s, C$_4$), 148.1 (s, C$_2$), 145.2 (s, C$_6$), 96.9 (s, C$_5$), 87.0 (s, C$_{1'}$), 82.3 (d, J$_{C4'-P}$=8.0 Hz, C$_{4'}$), 75.8 (s, C$_{2'}$), 74.1 (s, C$_{3'}$), 69.6 (s, (OCH$_2$)$_{PEG}$), 68.4 (s, (OCH$_2$β)), 64.1 (s, OCH$_2$α)$_{PEG}$), 63.6 (s, C$_{5'}$), 46.6 (s, (CH$_3$CH$_2$)$_3$NH), 31.6, 28.3 (s, CH$_{2succ}$), 8.2 (s, (CH$_3$CH$_2$)$_3$NH).

$^{31}$P NMR (D$_2$O, 121 MHz) δ 0.26 (s).

EXAMPLE 11 bis: Poly (oxyethylene)$_{4000}$ bis[4-N-(1-(β-D-arabino-furanosyl)-cytosyl-5'-monophosphate)-3-hydroxy propanamide], triethylammonium salts

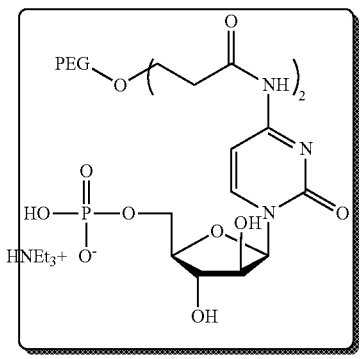

Monophosphorylation of PEG-bis(OCH$_2$CH$_2$—CO-AraC) (1.1 g, 0.24 mmole) was carried out using method B and PEG-bis(OCH$_2$CH$_2$—CO-AraCMP) was obtained in the form of a white solid (0.95 g, 84%).

$^1$H NMR (D$_2$O, 200 MHz) δ 8.29 (d, J$_{6-5}$=7.2 Hz, 1H, H$_6$), 7.27 (d, J$_{5-6}$=7.2 Hz, 1H, H$_5$), 6.17 (m, 1H, H$_{1'}$), 4.42 (m, 1H, H$_{2'}$), 4.09 (m, 4H, H$_{3'}$,H$_{4'}$2H$_{5'}$), 3.96-3.25 (m, (OCH$_2$)$_{PEG}$), 3.10 (q, J=7 Hz, 6H, (CH$_3$CH$_2$)$_3$NH), 2.62 (t, JGH$_{2a}$-CH$_{2b}$=6 Hz, 2H, CH$_2$a), 1.18 (t, J=7 Hz, 9H, (CH$_3$CH$_2$)$_3$NH).

$^{31}$P NMR (D$_2$O, 81 MHz) δ 0.22 (s).

EXAMPLE 12

Poly(ethyleneglycol)$_{4000}$ bis[4-N-(1-(2'-deoxy-β-D-ribofuranosyl)-cytosyl-5'-monophosphate) succinate], tri-ethylammonium salts

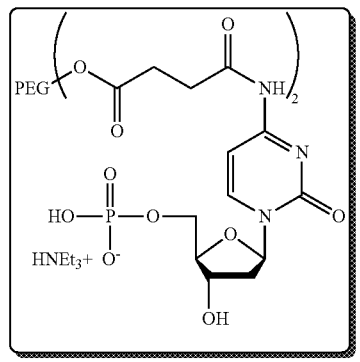

Monophosphorylation of 1 g (0.21 mmole) of PEG-O-bis(succinyl-dC) from Example 5 was carried out using method B of Example 10 with 30 eq of phosphorus oxychloride (0.59 mL, 6.49 mmole). The compound was obtained in the form of a white solid (0.93 g, 86%).

HPLC tr$_{dCMP}$: 13.07 min tx$_{monophosphorylation}$: 80%.

$^1$H NMR (D$_2$O, 300 MHz) δ 8.38 (d, J$_{6-5}$=7.5 Hz, 1H, H$_6$), 7.16 (d, J$_{5-6}$=7.5 Hz, 1H, H$_5$), 6.17 (t, J$_{1'-2'a}$=J$_{1'-2'b}$=6.1 Hz,

1H, H$_{1'}$), 4.45 (m, 1H, H$_{3'}$), 4.19 (m, 2H, (OCH$_2\alpha$)$_{PEG}$), 4.11-3.95 (m, 3H, H$_{4'}$.2H$_{5'}$), 3.95-3.35 (m, (OCH$_2$)$_{PEG}$), 3.10 (q, J=7.2 Hz, 6H, (CH$_3$CH$_2$)$_3$NH), 2.82-2.62 (m, 4H, CH$_{2succ}$), 2.48 (m, 1H, H$_{2'a}$), 2.25 (m, 1H, H$_{2'b}$), 1.18 (t, J=7.2 Hz, 9H, (CH$_3$CH$_2$)$_3$NH).

$^{13}$C NMR (D$_2$O, 100 MHz) δ 174.7, 174.5 (2s, C=O$_{succ}$), 161.5 (s, C$_4$), 155.2 (s, C$_2$), 146.5 (s, C$_6$), 97.5 (s, C$_5$), 87.5 (s, C$_{1'}$), 86.3 (d, J$_{C4'-P}$=8.0 Hz, C$_{4'}$), 70.4 (s, C$_{3'}$), 69.6 (s, (OCH$_2$)$_{PEG}$), 68.4 (s, (OCH$_2\beta$)$_{PEG}$), 64.2 (s, (OCH$_2\alpha$)$_{PEG}$), 64.1 (d, J$_{C5'-P}$=8.0 Hz, C$_{5'}$), 46.6 (s, (CH$_3$CH$_2$)$_3$NH), 40.1 (s, C$_{2'}$), 31.6, 28.4 (2s, CH$_{2succ}$), 8.2 (s, (CH$_3$CH$_2$)$_3$NH).

$^{31}$P NMR (D$_2$O, 121 MHz) δ 0.19 (s).

EXAMPLE 13

Poly(ethyleneglycol)$_{4000}$ bis[4-N-(1-(β-D-ribofuranosyl)-cytosyl-5'-monophosphate) succinate], tri-ethylammonium salts

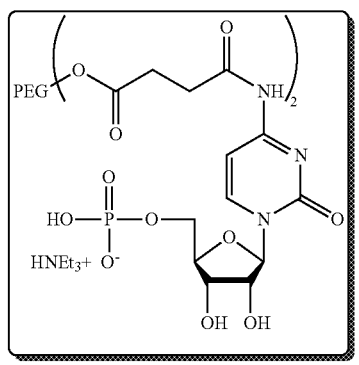

Monophosphorylation of 0.50 g of PEG-O-bis(succ-C) (0.11 mmole) from Example 6 was carried out using method B of Example 10, with 30 eq of phosphorus oxychloride (0.29 g, 3.30 mL). The compound was obtained in the form of a white solid (4.80 g, 89%).

HPLC tr$_{CMP}$: 14.17 min tx$_{monophosphorylation}$: 96%.

$^1$H NMR (D$_2$O, 300 MHz) δ 8.59 (d, J$_{6-5}$=7.8 Hz, 1H, H$_6$), 7.10 (d, J$_{5-6}$=7.5 Hz, 1H, H$_5$), 5.97 (s, 1H, H$_{1'}$), 4.91-4.12 (m, 7H, H$_{2'}$, H$_{3'}$, H$_{4'}$, 2H$_{5'}$(OCH$_2\alpha$)$_{PEG}$), 3.94-3.47 (m, (OCH$_2$)$_{PEG}$), 3.20 (q, J=7.2 Hz, 6H, (CH$_3$CH$_2$)$_3$NH), 2.95-2.75 (m, 4H, CH$_{2succ}$), 1.28 (t, J=7.2 Hz, 9H, (CH$_3$CH$_2$)$_3$NH).

$^{13}$C NMR (D$_2$O, 100 MHz) δ 174.7, 174.4 (2s, C=O$_{succ}$), 161.1 (s, C$_4$), 154.0 (s, C$_2$), 147.3 (s, C$_6$), 97.3 (s, C$_5$), 91.1 (s, C$_{1'}$), 86.4 (d, J$_{C4'-P}$=8.0 Hz, C$_{4'}$), 74.3 (s, C$_{2'}$), 69.6 (s, C$_{3'}$ (OCH$_2$)$_{PEG}$), 68.4 (s, (OCH$_2\beta$)$_{PEG}$), 64.1 (s, (OCH$_2\alpha$)$_{PEG}$), 64.0 (s, C$_{5'}$), 46.6 (s, (CH$_3$CH$_2$)$_3$NH), 31.6, 28.2 (2s, CH$_{2succ}$), 8.2 (s, (CH$_3$CH$_2$)$_3$NH).

$^{31}$P NMR (D$_2$O, 121 MHz) δ 0.12 (s).

EXAMPLE 14

Poly(ethyleneglycol)$_{4000}$ bis[4-N-(1-(2',3'-dideoxy-β-D-ribofuranosyl)-cytosyl-5'-monophosphate) succinate], tri-ethylammonium salts

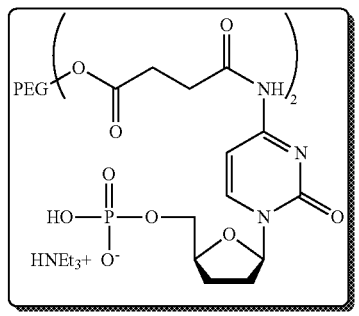

Monophosphorylation of 0.04 g of PEG-O-bis(succinyl-ddC) (0.09 mmole) from Example 7 was carried out using method B of Example 10, using 30 eq of phosphorus oxychloride (0.24 mL, 2.70 mmole), in the presence of activated molecular sieve (3 Å). The expected compound was obtained in the form of a white solid (0.41 g, 96%).

$^1$H NMR (D$_2$O, 300 MHz) δ 8.49 (d, 7.5 Hz, 1H, H$_6$), 7.13 (d, J$_{5-6}$=7.3 Hz, 1H, H$_5$), 5.98 (d, J$_{1'-2'}$=5.1 Hz, 1H, H$_{1'}$), 4.35 (m, 1H, H$_{4'}$), 4.18-3.92 (m, 4H, (OCH$_2\alpha$)$_{PEG}$ 2H$_{5'}$), 3.85-3.36 (m, OCH$_2$)$_{PEG}$), 3.10 (q, J=7.2 Hz, 6H, (CH$_3$CH$_2$)$_3$NH), 2.79-2.68 (m, 4H, CH$_{2succ}$), 2.46 (m, 1H, H$_{2'a}$), 2.08 (m, 1H, H$_{2'b}$), 1.97 (m, 1H, H$_{3'a}$), 1.83 (m, 1H, H$_{3'b}$), 1.18 (t, J=7.2 Hz, 9H, (CH$_3$CH$_2$)$_3$NH).

$^{31}$P NMR (D$_2$O, 121 MHz) δ 0.37 (s).

EXAMPLE 15

Method C: Diphosphorylation: Phosphorylation of Monophosphate Nucleoside on Polymer Support A suspension of PEG-O-bis(succinyl-nucleoside monophosphate) (1 eq) in tributylamine (2.50 mL) was stirred for 10 min at ambient temperature. Cold diethyl ether (50 mL) was added and the precipitate was filtered, washed with diethyl ether and vacuum dried overnight over KOH pellets. The monophosphate nucleoside on polymer support was dissolved in anhydrous N,N-dimethylformamide (3.75 mL) and 1,1'-carbonyldiimidazole (0.59 mmole, 6 eq) was added. The reaction mixture was stirred for 2 h at ambient temperature, and treated with anhydrous methanol (0.10 mL). After 15 minutes of stirring, a solution of tributylammonium phosphate in anhydrous N,N-dimethylformamide (1M, 1.49 mmole, 15 eq) was added and the suspension was stirred for 24 h at ambient temperature. The mixture was treated with an equal volume of methanol, then concentrated under reduced pressure. The residue was precipitated with cold diethyl ether (50 mL). The precipitated was filtered and washed with diethyl ether. The crude product was chromatographed on a RP18 reverse phase column (acetonitrile gradient: 0 to 70%, in water).

EXAMPLE 16

Poly(ethyleneglycol)-4000 bis[4-N-(1-(β-D-arabinofuranosyl)-cytosyl-5'-diphosphate) succinate], tributylammonium salts

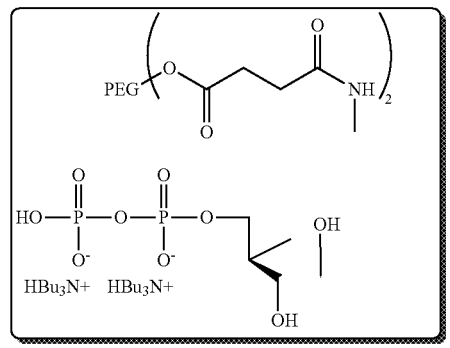

Diphosphorylation of 0.5 g (0.09 mmole) of PEG-O-bis (succ-CMP) was carried out using method C of Example 15 and produced the compound in the form of a white solid (0.36 g, 66%) after lyophilisation.

$^1$H NMR (D$_2$O, 300 MHz) δ 8.24 (d, J$_{6-5}$=7.5 Hz, 1H, H$_6$), 7.27 (d, J$_{5-6}$=7.5 Hz, 1H, H$_5$), 6.17 (d, J$_{1'-2'}$=5.1 Hz, 1H, H$_{1'}$), 4.42 (t, J$_{2'-1'}$=J$_{2'-3'}$=5.1 Hz, 1H, H$_{2'}$), 4.28-4.05 (m, 6H, H$_3$, H$_{4'}$, 2H$_{5'}$, (OCH$_2$α)$_{PEG}$), 3.89-3.35 (m, (OCH$_2$)$_{PEG}$), 2.92 (t, J=7.7 Hz, 12H, (CH$_3$CH$_2$CH$_2$CH$_2$)$_3$NH), 2.80-2.68 (m, 4H, CH$_{2succ}$), 1.54 (m, 12H, (CH$_3$CH$_2$CH$_2$CH$_2$)$_3$NH), 1.29 (m, 12H, (CH$_3$CH$_2$CH$_2$CH$_2$)$_3$NH), 0.81 (t, J=7.2 Hz, 18H, (CH$_3$CH$_2$CH$_2$CH$_2$)$_3$NH).

$^{13}$C NMR (D$_2$O, 100 MHz) δ 174.6, 174.4 (2s, C=O$_{succ}$), 162.5 (s, C$_4$), 156.8 (s, C$_2$), 146.8 (s, C$_6$), 97.6 (s, C$_5$), 86.6 (s, C$_{1'}$), 82.0 (d, J$_{C4'-P}$=9.0 Hz, C$_{4'}$), 75.1 (s, C$_{2'}$), 74.3 (s, C$_{3'}$), 69.6 (s, (OCH$_2$)$_{PEG}$), 68.4 (s, (OCH$_2$β)$_{PEG}$), 64.1 (s, (OCH$_2$α)$_{PEG}$), 64.1 (s, C$_{5'}$), 52.6 (s, (CH$_3$CH$_2$CH$_2$CH$_2$)$_3$NH), 31.6, 28.4 (2s, CH$_{2succ}$), 25.2 (s, (CH$_3$CH$_2$CH$_2$CH$_2$)$_3$NH), 19.2 (s, CH$_3$CH$_2$CH$_2$CH$_2$)$_3$NH), 12.8 (s, (CH$_3$CH$_2$CH$_2$CH$_2$)$_3$NH).

$^{31}$P NMR (D$_2$O, 121 MHz) δ −10.44 (m, P$_β$), −11.03 (m, P$_α$).

EXAMPLE 17

Poly(ethyleneglycol)$_{4000}$ Bis[4-N-(1-(2'-deoxy-β-D-ribofuranosyl)-cytosyl-5'-diphosphate) succinate], tributylammonium salts

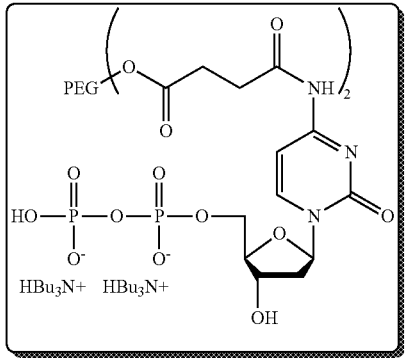

Diphosphorylation of 0.30 g of PEG-O-bis(succ-dCMP) (0.06 mmole) was carried out using method C of Example 15 and produced the compound in the form of a white solid (0.28 g, 81%) after lyophilisation.

$^1$H NMR (D$_2$O, 300 MHz) δ 8.36 (d, J$_{6-5}$=7.5 Hz, 1H, H$_6$), 7.29 (d, J$_{5-6}$=7.5 Hz, 1H, H$_5$), 6.22 (t, J$_{1'-2'a}$=J$_{1'-2'b}$=6.3 Hz, 1H, H$_{1'}$), 4.52 (m, 1H, H$_{3'}$), 4.24-4.09 (m, 5H, H$_{4'}$, 2H$_{5'}$, (OCH$_2$α)$_{PEG}$), 3.89-3.56 (m, (OCH$_2$)$_{PEG}$), 3.13 (m, 12H, (CH$_3$CH$_2$CH$_2$CH$_2$)$_3$NH), 2.80-2.68 (m, 4H, CH$_{2succ}$), 2.50 (ddd, J$_{2'a-4}$=6.0 Hz, J$_{2'a-3'}$=3.8 Hz, J$_{2'a-2'b}$=13.8 Hz, 1H, H$_{2'a}$), 2.28 (m, 1H, H$_{2'b}$), 1.59 (m, 12H, (CH$_3$CH$_2$CH$_2$CH$_2$)$_3$NH), 1.31 (m, 12H, (CH$_3$CH$_2$CH$_2$CH$_2$)$_3$NH), 0.86 (m, 18H, (CH$_3$CH$_2$CH$_2$CH$_2$)$_3$NH).

$^{13}$C NMR (D$_2$O, 100 MHz) δ 174.7, 174.5 (2s, C=O$_{succ}$), 162.4 (s, C$_4$), 156.8 (s, C$_2$), 145.8 (s, C$_6$), 98.3 (s, C$_5$), 87.3 (s, C$_{1'}$), 86.0 (d, J$_{C4'-P}$=8.0 Hz, C$_{4'}$), 70.4 (s, C$_{3'}$), 69.6 (s, (OCH$_2$)$_{PEG}$), 68.4 (s, (OCH$_2$β)$_{PEG}$), 64.9 (d, J$_{C5'-P}$=6.0 Hz, C$_{5'}$), 64.1 (s, (OCH$_2$α)$_{PEG}$), 52.7 (s, (CH$_3$CH$_2$CH$_2$)$_3$NH), 39.9 (s, C$_{2'}$), 31.6, 28.5 (2s, CH$_{2succ}$), 25.8 (s, (CH$_3$CH$_2$CH$_2$CH$_2$)$_3$NH), 19.2 (s, (CH$_3$CH$_2$CH$_2$CH$_2$)$_3$NH), 12.7 (s, (CH$_3$CH$_2$CH$_2$CH$_2$)$_3$NH).

$^{31}$P NMR (D$_2$O, 121 MHz) δ −10.69 (d, J$_{β-α}$=19.3 Hz, P$_β$), −11.26 (d, J$_{α-β}$=17.3 Hz, P$_α$).

EXAMPLE 18

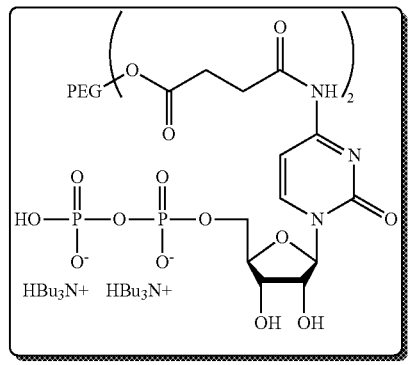

Diphosphorylation of 0.55 g of PEG-O-succ-CMP (0.11 mmole) was carried out using method C of Example 15. A mixture (comprising the corresponding 2',3' carbonate derivative) was obtained in the form of a white solid (0.34 g, 60%) after lyophilisation.

Poly(ethylene glycol)$_{4000}$ bis[4-N-(1-(β-D-ribofuranosyl)-cytosyl-5'-diphosphate) succinate], tributylammonium salts $^1$H NMR (D$_2$O, 300 MHz) δ 8.32 (d, J$_{6-5}$=6.9 Hz, 1H, H$_6$), 7.25 (d, J$_{5-6}$=6.9 Hz, 1H, H$_5$), 5.88 (d, J$_{1'-2'}$=1.8 Hz, 1H, H$_{1'}$), 4.30-4.07 (m, 7H, H$_{2'}$, H$_{3'}$, H$_{4'}$, 2H$_{5'}$, (OCH$_2$α)$_{PEG}$), 3.88-3.33 (m, (OCH$_2$)$_{PEG}$), 3.09 (m, 12H, ((CH$_3$CH$_2$CH$_2$C$_2$)$_3$NH), 2.84-2.62 (m, 4H, CH$_{2succ}$), 1.54 (m, 12H, (CH$_3$CH$_2$CH$_2$CH$_2$)$_3$NH), 1.30-1.15 (m, 12H, (CH$_3$CH$_2$CH$_2$CH$_2$)$_3$NH), 0.92-0.68 (m, 18H, (CH$_3$CH$_2$CH$_2$CH$_2$)$_3$NH).

$^{31}$P NMR (D$_2$O, 121 MHz) δ −10.79 (m, P$_β$), −11.85 (m, P$_α$).

Poly(ethylene glycol)$_{4000}$ bis[4-N-(1-(2',3'-carbonyl-β-D-ribofuranosyl)-cytosyl-5'-diphosphate) succinate], tributylammonium salts $^1$H NMR (D$_2$O, 300 MHz) δ 8.12 (d, J$_{6-5}$=7.5 Hz, 1H, H$_6$), 7.24 (d, J$_{5-6}$=7.5 Hz, 1H, H$_5$), 5.98 (s, 1H, H$_{1'}$), 5.53, 5.46 (dd, J$_{2'-3'}$=J$_{3'-2'}$=7.5 Hz, J$_{2'-1'}$=J$_{3'-4'}$=1.8 Hz, 2H, H$_{2'}$, H$_{3'}$), 4.84 (m, 1H, H$_{4'}$) 4.07-4.30 (m, 4H, 2H$_{5'a}$ (OCH$_2$α)$_{PEG}$), 3.88-3.33 (m, (OCH$_2$)$_{PEG}$), 3.09 (m, 12H, ((CH$_3$CH$_2$CH$_2$CH$_2$)$_3$NH), 2.84-2.62 (m, 4H, CH$_{2succ}$), 1.54 (m, 12H, (CH$_3$CH$_2$CH$_2$CH$_2$)$_3$NH), 1.30-1.15 (m, 12H, (CH$_3$CH$_2$CH$_2$CH$_2$)$_3$NH), 0.68-0.92 (m, 18H, (CH$_3$CH$_2$CH$_2$CH$_2$)$_3$NH).

$^{31}$P NMR (D$_2$O, 121 MHz) δ −10.79 (m, P$_β$), −11.85 (m, P$_α$).

EXAMPLE 19

Method D: Triphosphorylation; Diphosphorylation of Nucleoside Monophosphate on Polymer Support A suspension of PEG-O-bis(succinyl-nucleoside monophosphate) or PEG-bis(OCH$_2$CH$_2$—CO-nucleoside monophosphate) (1 eq) in tributylamine (2.50 mL) was stirred for 10 min at ambient temperature. Cold diethyl ether (50 mL) was added and the precipitate was filtered, washed and vacuum dried overnight on KOH pellets. The nucleoside monophosphate on polymer support was dissolved in anhydrous N,N-dimethylformamide (3.75 mL) and 1,1-carbonyldiimidazole (0.59 mmole, 6 eq) was added. The reaction mixture was stirred for 2 h at ambient temperature and treated with anhydrous methanol (0.10 mL). After 15 min, a solution of tributylammonium pyrophosphate in anhydrous N,N-dimethylformamide (1M, 1.49 mmole, 15 eq) was added. The suspension was stirred for 24 h at ambient temperature. The mixture was treated with an equal volume of methanol, then concentrated under reduced pressure. The residue precipitated out in cold diethyl ether (50 mL). The precipitate was filtered and washed with diethyl ether. The crude product was chromatographed on a RP18 reverse phase column with an acetonitrile gradient: 0 to 70% in water.

EXAMPLE 20

Poly(ethyleneglycol)$_{4000}$ bis[4-N-(1-(β-D-arabinofuranosyl)-cytosyl-5'-triphosphate) succinate], tributylammonium salts

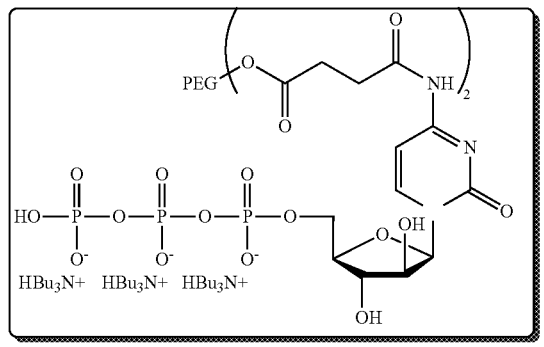

Triphosphorylation of 0.50 g of PEG-O-bis(succ-araCMP) (0.09 mmole) was carried out using method D of Example 19 and provided the compound in the form of a white solid (0.43 g, 69%) after lyophilisation.

$^1$H NMR (D$_2$O, 300 MHz) δ 8.29 (d, J$_{6-5}$=7.5 Hz, 1H, H$_6$), 7.17 (d, J$_{5-6}$=7.5 Hz, 1H, H$_5$), 6.17 (d, J$_{1'-2'}$=5.1 Hz, 1H, H$_{1'}$), 4.41 (t, J$_{2'-1'}$=J$_{2'-3'}$=5.1 Hz, 1H, H$_{2'}$), 4.27-4.05 (m, 6H, H$_3$, H$_{4'}$, 2H$_{5'}$, (OCH$_2$α)$_{PEG}$), 3.88-3.30 (m, (OCH$_2$)$_{PEG}$), 3.03 (t, J=7.4 Hz, 18H, (CH$_3$CH$_2$CH$_2$CH$_2$)$_3$NH), 2.87-2.65 (m, 4H, CH$_{2succ}$), 1.57 (m, 18H, (CH$_3$CH$_2$CH$_2$CH$_2$)$_3$NH), 1.27 (m, 18H, (CH$_3$C$_2$CH$_2$CH$_2$)$_3$NH), 0.83 (t, J=7.1 Hz, 27H, (CH$_3$CH$_2$CH$_2$CH$_2$)$_3$NH).

$^{13}$C NMR (D$_2$O, 100 MHz) δ 174.7, 174.5 (2s, C=O$_{succ}$), 161.5 (s, C$_4$), 155.1 (s, C$_2$), 147.6 (s, C$_6$), 97.2 (s, C$_5$), 86.6 (s, C$_{1'}$), 82.0 (d, J$_{C4'-P}$=9.0 Hz, C$_{4'}$), 75.2 (s, C$_{2'}$), 74.0 (s, C$_{3'}$), 69.6 (s, (OCH$_2$)$_{PEG}$), 68.4 (s, (OCH$_2$β)$_{PEG}$), 64.2 (s, (OCH$_2$α)$_{PEG}$), 64.1 (d, J$_{C5'-P}$=8.0 Hz, C$_{5'}$), 52.6 (s, (CH$_3$CH$_2$CH$_2$CH$_2$)$_3$NH), 31.6, 28.4 (2s, CH$_{2succ}$), 25.2 (s, (CH$_3$CH$_2$CH$_2$CH$_2$)$_3$NH), 18.3 (s, CH$_3$CH$_2$CH$_2$CH$_2$)$_3$NH), 12.8 (s, (CH$_3$CH$_2$CH$_2$CH$_2$)$_3$NH).

$^{31}$P NMR (D$_2$O, 121 MHz) δ −10.94 (d, J$_{γ-β}$=19.43 Hz, P$_γ$), −11.32 (d, J$_{α-β}$=19.43 Hz, P$_α$), −23.28 (t, J$_{β-γ}$=J$_{β-α}$=19.43 Hz, P$_β$).

EXAMPLE 20 bis: Poly (oxyethylene)$_{4000}$ bis[4-N-(1-(β-D-arabinofuranosyl)-cytosyl-5'-triphosphate)-3-hydroxy propanamide], tributylammonium salts

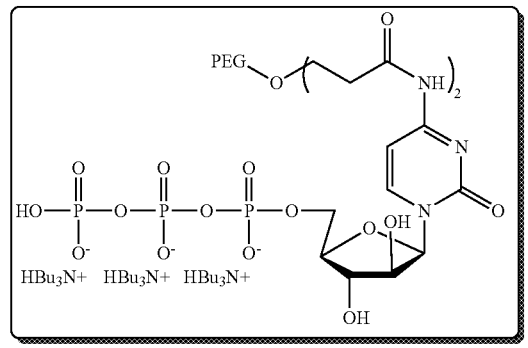

Triphosphorylation of PEG-bis(OCH$_2$CH$_2$—CO-AraCMP) (0.70 g, 0.15 mmole) was carried out using method D and the PEG-bis(OCH$_2$CH$_2$—CO-AraCTP) was obtained in the form of a white solid (0.41 g, 55%) after lyophilisation.

$^1$H NMR (D$_2$O, 300 MHz) δ 8.29 (d, J$_{6-5}$=7.2 Hz, 1H, H$_6$), 7.27 (d, J$_{5-6}$=7.2 Hz, 1H, H$_5$), 6.17 (m, 1H, H$_{1'}$), 4.42 (m, 1H, H$_{2'}$), 4.09 (m, 4H, H$_3$, H$_{4'}$, 2H$_{5'}$), 3.94-3.30 (m, (OCH$_2$)$_{PEG}$), 3.06 (t, J=7.9 Hz, 18H, (CH$_3$CH$_2$CH$_2$CH$_2$)$_3$NH), 2.62 (t, JCH$_{2a}$-CH$_{2b}$=6 Hz, 2H, CH$_2$a), 1.51 (m, 18H, (CH$_3$CH$_2$CH$_2$CH$_2$)$_3$NH), 1.26 (m, 18H, (CH$_3$CH$_2$CH$_2$CH$_2$)$_3$ NH), 0.94 (t, 27H, (CH$_3$CH$_2$CH$_2$CH$_2$)$_3$NH).

$^{31}$P NMR (D$_2$O, 121 MHz) δ −10.80 (d, J$_{γ-β}$=21.17 Hz, P$_γ$), −11.84 (d, J$_{α-β}$=21.17 Hz, P$_α$), −23.31 (t, J$_{β-γ}$=J$_{β-α}$=21.17 Hz, P$_β$).

EXAMPLE 21

Poly(ethyleneglycol)$_{4000}$ bis[4-N-(1-(2'-deoxy-β-D-ribofuranosyl)-cytosyl-5'-triphosphate) succinate], tributylammonium salts

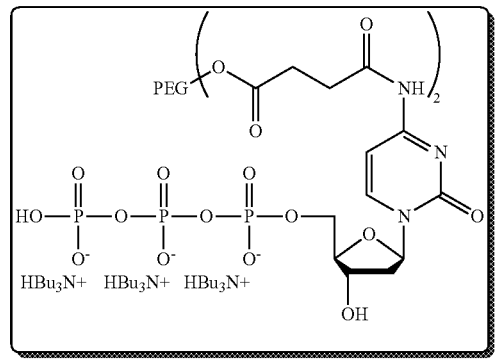

Triphosphorylation of 0.30 g of PEG-O-bis(succ-dCMP) (0.06 mmole) was carried out using method D of Example 19 and provided the compound in the form of a white solid (0.27 g, 73%) after lyophilisation.

$^1$H NMR (D$_2$O, 300 MHz) δ 8.35 (d, J$_{6-5}$=7.5 Hz, 1H, H$_6$), 7.17 (d, J$_{5-6}$=7.5 Hz, 1H, H$_5$), 6.17 (t, J$_{1'-2'a}$=J$_{1'-2'b}$=6.3 Hz, 1H, H$_{1'}$), 4.51 (m, 1H, H$_{3'}$), 4.21-4.13 (m, 5H, H$_{4'}$ 2H$_{5'}$ (OCH$_2$α)$_{PEG}$), 3.89-3.31 (m, (OCH$_2$)$_{PEG}$), 3.17-2.95 (m, 18H, (CH$_3$CH$_2$CH$_2$CH$_2$)$_3$NH), 2.79-2.62 (m, 4H, CH$_{2succ}$), 2.47 (m, 1H, H$_{2'a}$), 2.26 (m, 1H, H$_{2'b}$), 1.59-1.45 (m, 18H, (CH$_3$CH$_2$CH$_2$CH$_2$)$_3$NH), 1.40-1.25 (m, 18H, (CH$_3$CH$_2$CH$_2$CH$_2$)$_3$NH), 0.90-0.75 (m, 27H, (CH$_3$CH$_2$CH$_2$CH$_2$)$_3$NH).

$^{13}$C NMR (D$_2$O, 100 MHz) δ 174.8, 174.6 (2s, C=O$_{succ}$), 161.8 (s, C$_4$), 155.4 (s, C$_2$), 146.3 (s, C$_6$), 98.0 (s, C$_5$), 87.4 (s, C$_{1'}$), 86.2 (s, C$_{4'}$), 70.3 (s, C$_{3'}$), 69.6 (s, (OCH$_2$)$_{PEG}$), 68.4 (s, (OCH$_2$β)$_{PEG}$), 65.2 (s, C$_{5'}$), 64.1 (s, (OCH$_2$α)$_{PEG}$), 52.6 (s, (CH$_3$CH$_2$CH$_2$CH$_2$)$_3$NH), 40.0 (s, C$_{2'}$), 31.6, 28.4 (2s, CH$_{2succ}$), 25.2 (s, (CH$_3$CH$_2$CH$_2$CH$_2$)$_3$NH), 19.1 (s, (CH$_3$CH$_2$CH$_2$CH$_2$)$_3$NH), 12.8 (s, (CH$_3$CH$_2$CH$_2$CH$_2$)$_3$NH).

$^{31}$P NMR (D$_2$O, 121 MHz) δ −10.73 (d, J$_{γ-β}$=20.6 Hz, P$_γ$), −11.34 (d, J$_{α-β}$=19.4 Hz, P$_α$), −22.81 (m, P$_β$).

EXAMPLE 22

Poly(ethyleneglycol)$_{4000}$ bis[4-N-(1-(β-D-ribofuranosyl)-cytosyl-5'-triphosphate) succinate], tributylammonium salts

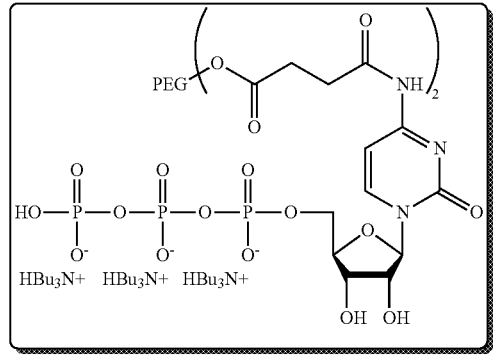

Triphosphorylation of 0.30 g of PEG-O-bis(succ-CMP) (0.11 mmole) was carried out using method D of Example 19. A mixture (1/1) of the expected compound and the corresponding 2',3' carbonate derivative, was obtained in the form of a white solid (0.26 g, 70%) after lyophilisation.

Poly(ethyleneglycol)$_{4000}$ bis[4-N-(1-(β-D-ribofuranosyl)-cytosyl-5'-triphosphate) succinate], tributylammonium salts $^1$H NMR (D$_2$O, 300 MHz) δ 8.30 (d, J$_{6-5}$=7.5 Hz, 1H, H$_6$), 7.22 (d, J$_{5-6}$=7.5 Hz, 1H, H$_5$), 5.87 (d, J$_{1'-2'}$=2.8 Hz, 1H, H$_{1'}$), 4.25-4.14 (m, 7H, H$_2$, H$_3$, H$_4$, H$_5$, (OCH$_2$C)$_{PEG}$), 3.97-3.25 (m, (OCH$_2$)$_{PEG}$), 3.14-2.98 (m, 18H, (CH$_3$CH$_2$CH$_2$CH$_2$)$_3$NH), 2.74-2.60 (m, 4H, CH$_{2succ}$), 1.63-1.48 (m, 18H, (CH$_3$CH$_2$CH$_2$CH$_2$)$_3$NH), 1.13-1.35 (m, 18H, (CH$_3$CH$_2$CH$_2$CH$_2$)$_3$NH), 0.86-0.78 (m, 27H, (CH$_3$CH$_2$CH$_2$CH$_2$)$_3$NH).

$^{31}$P NMR (D$_2$O, 81 MHz) δ −10.65 (m, P$_γ$), −12.10 (m, P$_α$), −22.94 (M, P$_β$).

Poly(ethyleneglycol)$_{4000}$ bis[4-N-(1-(2',3'-carbonyl-β-D-ribofuranosyl)-cytosyl-5'-triphosphate) succinate], tributylammonium salts $^1$H NMR (D$_2$O, 300 MHz) δ 8.12 (d, J$_{6-5}$=7.6 Hz, 1H, H$_6$), 7.21 (d, J$_{5-6}$=7.6 Hz, 1H, H$_5$), 5.97 (s, 1H, H$_{1'}$), 5.50 (m, 2H, H$_{2'}$, H$_{3'}$), 4.86 (m, 1H, H$_{4'}$), 4.25-4.14 (m, 4H, 2H$_{5'}$ (OCH$_2$α)$_{PEG}$), 3.97-3.25 (m, (OCH$_2$)$_{PEG}$), 3.14-2.98 (m, 18H, (CH$_3$CH$_2$CH$_2$CH$_2$)$_3$NH), 2.74-2.60 (m, 4H, CH$_{2succ}$), 1.63-1.48 (m, 18H, (CH$_3$CH$_2$CH$_2$CH$_2$)$_3$NH), 1.35-1.13 (m, 18H, (CH$_3$CH$_2$CH$_2$CH$_2$)$_3$NH), 0.86-0.78 (m, 27H, (CH$_3$CH$_2$CH$_2$CH$_2$)$_3$NH).

$^{31}$P NMR (D$_2$O, 81 MHz) δ −10.65 (m, P$_γ$), −12.10 (m, P$_α$), −22.94 (m, P$_β$).

EXAMPLE 23

Poly(ethyleneglycol)$_{4000}$ bis[4-N-(1-(β-D-ribofuranosyl)-cytosyl-5'-triphosphate) succinate], tri-ethylammonium and carbonyldiimidazolium salts

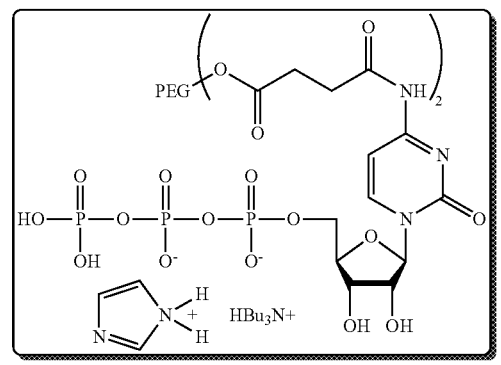

Triphosphorylation of 0.32 g of PEG-O-bis(succ-CMP) (0.06 mmole) was carried out using method D of Example 19. The activation was carried out with carbonyldiimidazole (3 eq) for 30 min only. The compound of the heading was obtained in the form of a white solid (0.17 g, 42%) after lyophilisation.

$^1$H NMR (D$_2$O, 300 MHz) δ 8.60 (s, 2H, N=CH—N), 8.31 (d, J$_{6-5}$=7.5 Hz, 1H, H$_6$), 7.38 (s, 4H, N=CH=CH), 7.23 (d, J$_{5-6}$=7.5 Hz, 1H, H$_5$), 5.89 (d, J$_{1'-2'}$=2.8 Hz, 1H, H$_{1'}$), 4.28-4.19 (m, 7H, H$_2$, H$_3$, H$_4$, 2H$_5$, (OCH$_2$α)$_{PEG}$), 3.86-3.34 (m, (OCH$_2$)$_{PEG}$), 3.10 (q, J=7.3 Hz, 611, (CH$_3$CH$_2$)$_3$NH), 2.79-2.62 (m, 4H, CH$_{2succ}$), 1.18 (t, J=7.3 Hz, 9H, (CH$_3$CH$_2$)$_3$NH).

$^{31}$P NMR (D$_2$O, 121 MHz) δ −10.75 (d, J$_{γ-β}$=19.4 Hz, P$_γ$), −11.37 (d, J$_{α-β}$=19.4 Hz, P$_α$), −23.08 (t, J$_{β-γ}$=J$_{β-α}$=19.4 Hz, P$_β$).

EXAMPLE 24

Poly(ethyleneglycol)$_{4000}$ bis[4-N-(1-(2',3'-dideoxy-β-D-ribofuranosyl)-cytosyl-5'-triphosphate) succinate], tributylammonium salts

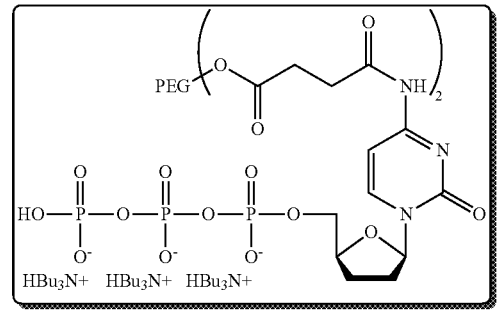

Triphosphorylation of 0.36 g of PEG-O-bis(succ-ddCMP) (0.07 mmole) was carried out using method of Example 19. The compound of the heading was obtained in the form of a white solid (0.27 g, 60%) after lyophilisation.

$^1$H NMR (D$_2$O, 300 MHz) δ 8.47 (d, J$_{6-5}$=7.2 Hz, 1H, H$_6$), 7.09 (d, J$_{5-6}$=7.5 Hz, 1H, H$_5$), 5.97 (m, 1H, H$_{1'}$), 4.36 (m, 1H, H$_{4'}$), 4.26 (m, 1H, H$_{5'a}$), 4.18 (m, 2H, (OCH$_2$α)$_{PEG}$), 4.08 (m, 1H, H$_{5'b}$), 3.83-3.35 (m, (OCH$_2$)$_{PEG}$), 3.02 (t, J=7.4 Hz, 18H, (CH$_3$CH$_2$CH$_2$CH$_2$)$_3$NH), 2.81-2.65 (m, 4H, CH$_{2succ}$), 2.44 (m, 1H, H$_{2'a}$), 2.15-1.80 (m, 2H, H$_{2'b}$ H$_{3'a}$), 1.82 (m, 1H, H$_{3'b}$), 1.56 (m, 18H, (CH$_3$CH$_2$CH$_2$CH$_2$)$_3$NH), 1.28 (m, 18H, (CH$_3$CH$_2$CH$_2$CH$_2$)$_3$NH), 0.82 (t, J=7.1 Hz, 27H, (CH$_3$CH$_2$CH$_2$CH$_2$)$_3$NH).

$^{13}$C NMR (D$_2$O, 100 MHz): 174.8, 174.5 (2s, C=O$_{succ}$), 161.0 (s, C$_4$), 155.0 (s, C$_2$), 144.8 (s, C$_6$), 97.3 (s, C$_5$), 88.6 (s, C$_{1'}$), 81.8 (s, C$_{4'}$), 69.6 (s, (OCH$_2$)$_{PEG}$), 68.4 (s, (OCH$_2$β)$_{PEG}$), 66.0 (s, C$_{5'}$), 64.1 (s, (OCH$_2$α)$_{PEG}$), 52.6 (s, (CH$_3$CH$_2$CH$_2$CH$_2$)$_3$NH), 32.5 (s, C$_{2'}$), 31.6, 28.4 (2s, CH$_{2succ}$), 25.2 (s, (CH$_3$CH$_2$CH$_2$CH$_2$)$_3$NH), 23.8 (s, C$_{3'}$), 19.2 (s, (CH$_3$CH$_2$CH$_2$CH$_2$)$_3$NH), 12.8 (s, (CH$_3$CH$_2$CH$_2$CH$_2$)$_3$NH).

$^{31}$P NMR (D$_2$O, 121 MHz) δ −11.00 (M, P$_γ$P$_α$), −22.85 (m, P$_β$).

EXAMPLE 25

Poly(ethyleneglycol)$_{4000}$ bis[4-N-(1-(2',3'-dideoxy-β-D-ribofuranosyl)-cytosyl-5'-disphosphate)succinate], tributylammonium salts

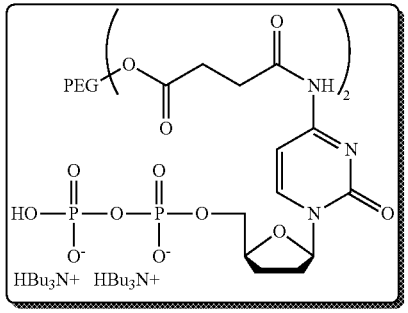

Diphosphorylation of PEG-O-bis(succ-ddCMP) (0.20 g, 0.04 mmole) was carried out using method C of Example 15. The compound of the heading was obtained in the form of a white solid (0.18 g, 80%) after lyophilisation.

$^1$H NMR (D$_2$O, 300 MHz) δ 8.35 (d, J$_{6-5}$=7.5 Hz, 1H, H$_6$), 7.21 (d, J$_{5-6}$=7.3 Hz, 1H, H$_5$), 5.94 (d, J$_{1'-2'}$=5.6 Hz, 1H, H$_{1'}$), 4.31 (m, 1H, H$_{4'}$), 4.16 (m, 3H, (OCH$_2$α)$_{PEG}$ H$_{5'a}$), 4.03-3.93 (m, 1H, H$_{5'b}$), 3.80-3.33 (m, OCH$_2$)$_{PEG}$), 3.00 (m, 12H, (CH$_3$CH$_2$CH$_2$CH$_2$)$_3$NH), 2.74-2.62 (m, 4H, CH$_{2succ}$), 2.37 (m, 1H, H$_{2'a}$), 2.00 (m, 2H, H$_{2'b}$ H$_{3'a}$), 1.77 (m, 1H, H$_{3'b}$), 1.55 (m, 12H, (CH$_3$CH$_2$CH$_2$CH$_2$)$_3$NH), 1.23 (m, 12H, (CH$_3$CH$_2$CH$_2$CH$_2$)$_3$NH), 0.80 (m, 18H, (CH$_3$CH$_2$CH$_2$CH$_2$)$_3$NH).

$^{13}$C NMR (D$_2$O, 100 MHz) δ 174.6, 174.4 (2s, C=O$_{succ}$), 162.2 (s, C$_4$), 155.8 (s, C$_2$), 146.0 (s, C$_6$), 97.7 (s, C$_5$), 88.2 (s, C$_{1'}$), 81.7 (s, C$_{4'}$), 69.6 (s, (OCH$_2$)$_{PEG}$), 68.4 (s, (OCH$_2$β)$_{PEG}$), 66.2 (s, C$_{5'}$), 64.1 (s, (OCH$_2$α)$_{PEG}$), 52.6 (s, (CH$_3$CH$_2$CH$_2$CH$_2$)$_3$NH), 32.6 (s, C$_{2'}$), 31.5, 28.4 (2s, CH$_{2succ}$), 25.2 (s, (CH$_3$CH$_2$CH$_2$CH$_2$)$_3$NH), 24.1 (s, C$_{3'}$), 19.3 (s, (CH$_3$CH$_2$CH$_2$CH$_2$)$_3$NH), 12.8 (s, (CH$_3$CH$_2$CH$_2$CH$_2$)$_3$NH).

$^{31}$P NMR (D$_2$O, 121 MHz) δ −10.29 (m, P$_β$), −10.97 (m, P$_α$).

EXAMPLE 26

Method E: Cleavage of Nucleotide from its Support

The supported nucleotide (0.05 mmole, 1 eq) was dissolved in concentrated ammonia (2 mL). The solution was stirred at ambient temperature for 1 h, then evaporated under reduced pressure. Purification was carried out by chromatography on a RP18 reverse phase column (isocratic; water) followed by dialysis over cellulose ester membranes.

EXAMPLE 26 bis

Method E bis: Cleavage of Nucleotides on Support

A nucleotide on support (0.05 mmole, 1 eq.) was dissolved in concentrated ammonia (2 mL). The solution was stirred at ambient temperature for 1 h, then evaporated off under reduced pressure. Purification was carried out by chromatography on a RP18 reverse phase column (isocratic; water), followed by lyophilisation.

As a departure from Example 26, the dialysis step was not carried out.

EXAMPLE 27

1-(β-D-arabinofuranosyl)-cytosine-5'-monophosphate, ammonium salt

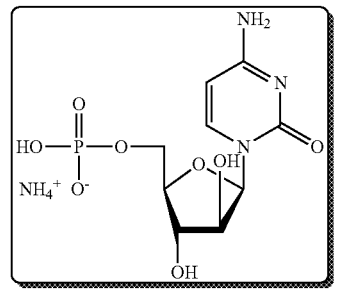

Method E of Example 26 was applied to 0.15 g of PEG-O-bis(succinyl-araCMP) (0.02 mmole). Purification by column chromatography of the crude product produced a mixture of araCMP and succinamide in a ratio of 93/7 (15 mg). The succinamide was eliminated by dialysis in water (2 mL) overnight and the araCMP (13 mg, 68%) was obtained in the form of a white solid after lyophilisation.

R$_f$ (iPrOH/H$_2$O/NH$_4$OH, 6/2/2, v/v/v): 0.2.

$^1$H NMR (D$_2$O, 300 MHz) δ 7.88 (d, J$_{6-5}$=7.6 Hz, 1H, H$_6$), 6.11 (d, J$_{1'-2'}$=5.3 Hz, 1H, H$_{1'}$), 6.02 (d, J$_{5-6}$=7.6 Hz, 1H, H$_5$), 4.34 (t, J$_{2'-1}$=J$_{2'-3}$=5.3 Hz 1H, H$_{2'}$), 4.11-3.96 (m, 4H, H$_3$, H$_{4'}$ 2H$_{5'}$).

$^{31}$P NMR (D$_2$O, 121 MHz) δ 0.45 (s).

UV (H$_2$O) λ$_{max}$ 272 nm (ε 7100), λ$_{min}$ 247 nm (ε 4100).

LC/MS (M−NH$_4^+$) m/z: 322 tr: 11.7 min purity: 97%.

EXAMPLE 27 bis

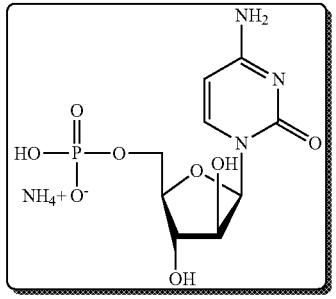

Method E bis was applied to PEG-bis(OCH$_2$CH$_2$—CO-AraCMP) (0.15 g, 0.02 mmole). Purification by column chromatography of the crude product produced araCMP in the form of a white solid (0.51 g, 70%) after lyophilisation.

EXAMPLE 28

1-(β-D-arabinofuranosyl)-cytosine-5'-diphosphate, ammonium salts

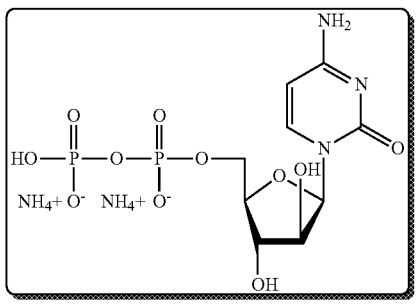

Method E of Example 26 was applied to 0.34 g of PEG-O-bis(succinyl-araCDP) (0.05 mmole). Purification by column chromatography of the crude product produced a mixture of araCDP and succinamide in the ratio 88/12 (55 mg). A 10 mg sample of the mixture was dissolved in water (2 mL) and purified overnight by dialysis. The araCDP (8.5 mg, 96%) was obtained in the form of a white solid after lyophilisation.

$R_f$(iPrOH/H$_2$O/NH$_4$OH, 5.5/3.5/1, v/v/v): 0.3.

$^1$H NMR (D$_2$O, 300 MHz) δ 7.85 (d, J$_{6-5}$=7.6 Hz, 1H, H$_6$), 6.14 (d, J$_{1'-2'}$=5.4 Hz, 1H, H$_{1'}$), 6.03 (d, J$_{5-6}$=7.6 Hz, 1H, H$_5$), 4.35 (t, J$_{2'-1'}$=J$_{2'-3'}$=5.4 Hz, 1H, H$_{2'}$), 4.20-4.10 (m, 3H, H$_{3'}$ 2H$_{5'}$), 4.00 (m, 1H, H$_{4'}$).

$^{31}$P NMR (D$_2$O, 121 MHz) δ −10.42 (d, J$_{\beta-\alpha}$=20.6 Hz, P$_\beta$), −11.10 (d, J$_{\alpha-\beta}$=20.6 Hz, P$_\alpha$).

UV (H$_2$O) λ$_{max}$ 274 nm (ε 7900), λ$_{min}$ 246 nm (E 3800).

LC/MS (M+H−2NH$_4^+$): m/z: 402 tr: 13.36 min purity: 86.7%.

EXAMPLE 29

1-(β-D-arabinofuranosyl)-cytosine-5'-triphosphate ammonium salts

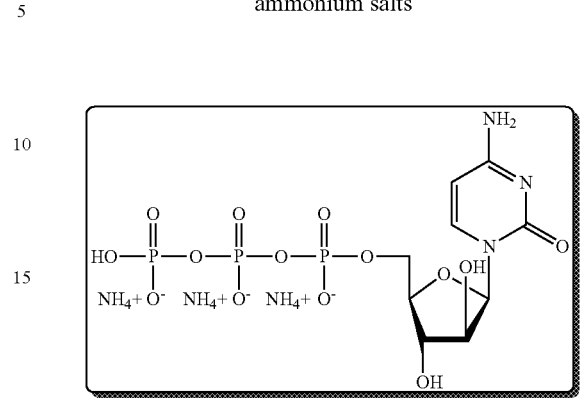

Method E of Example 26 was applied to 0.43 g of PEG-O-bis(succinyl-araCTP) (0.07 mmole). Column chromatography purification produced a mixture of araCTP and succinamide in the ratio 95/5 (68 mg). A sample of the mixture (8.5 mg) was dissolved in water (2 mL) and purified overnight by dialysis. AraCTP (8 mg, 92%) was obtained in the form of a white solid after lyophilisation.

$R_f$(iPrOH/H$_2$O/NH$_4$OH, 5.5/3.5/1, v/v/v): 0.2.

$^1$H NMR (D$_2$O, 300 MHz) δ 7.85 (d, J$_{6-5}$=7.6 Hz, 1H, H$_6$), 6.14 (d, J$_{1'-2'}$=5.4 Hz, 1H, H$_{1'}$), 6.04 (d, J$_{5-6}$=7.6 Hz, 1H, H$_5$), 4.35 (t, J$_{2'-1'}$=J$_{2'-3'}$=5.4 Hz, 1H, H$_{2'}$), 4.20-4.12 (m, 3H, H$_{3'}$ 2H$_{5'}$), 4.01 (m, 1H, H$_{4'}$).

$^{31}$P NMR (D$_2$O, 121 MHz) δ −10.45 (d, J$_{\gamma-\beta}$=18.2 Hz, P$_\gamma$), −11.20 (d, J$_{\alpha-\beta}$=19.4 Hz, P$_\alpha$), −22.96 (t, J$_{\beta-\gamma}$=J$_{\beta-\alpha}$=18.2 Hz, P$_\beta$).

UV (H$_2$O) λ$_{max}$ 273 nm (ε 8700), λ$_{min}$ 246 nm (ε 4500).

LC/MS (M+2H−3NH$_4^+$): m/z: 482 tr: 19.25 min purity: 83.3%.

EXAMPLE 29 bis

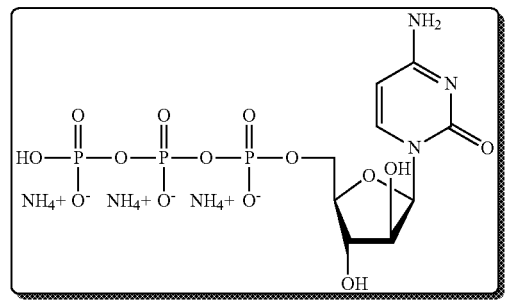

Method E bis was applied to PEG-bis(OCH$_2$CH$_2$—CO-AraCTP) (0.20 g, 0.04 mmole). After purification by RP18 reverse phase chromatography and lyophilisation, the AraCTP was obtained in the form of a white solid (14 mg, 79%).

EXAMPLE 30

1-(2'-deoxy-(β-D-ribofuranosyl)-cytosine-5'-monophosphate, ammonium salt

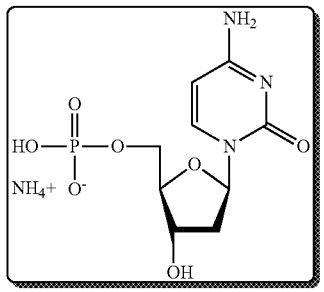

Method E of Example 26 was applied to 0.14 g of PEG-O-bis(succinyl-dCMP) (0.03 mmole). Column chromatographic purification produced a mixture of dCMP and succinamide in the ratio 86/14 (17 mg). A sample of the mixture (10 mg) was dissolved in water (2 mL) and purified overnight by dialysis. The dCMP (8.6 mg, 73%) was obtained in the form of a white solid after lyophilisation.

$R_f$ (iPrOH/H$_2$O/NH$_4$OH, 6/2/2, v/v/v): 0.5.

$^1$H NMR (D$_2$O, 300 MHz) δ 8.07 (d, J$_{6-5}$=7.8 Hz, 1H, H$_6$), 6.19 (t, J$_{1'-2'a}$=J$_{1'-2'b}$=6.5 Hz, 1H, H$_{1'}$), 6.09 (d, J$_{5-6}$=7.8 Hz, 1H, H$_5$), 4.45 (m, 1H, H$_{3'}$), 4.12 (m, 1H, H$_{4'}$), 4.04-3.90 (m, 2H, 2H$_{5'}$), 2.44-2.32 (ddd, J$_{2'a-1'}$=6.2 Hz, J$_{2'a-3'}$=3.7 Hz, J$_{2'a-2'}$=14.1 Hz, 1H, H$_{2'a}$), 2.27-2.18 (m, 1H, H$_{2'b}$).

$^{13}$C NMR (D$_2$O, 100 MHz) δ 161.8 (s, C$_4$), 151.7 (s, C$_2$), 143.3 (s, C$_6$), 95.5 (s, C$_5$), 86.4 (s, C$_{1'}$), 86.0 (d, J$_{C4'-P}$=8.0 Hz, C$_{4'}$), 70.7 (s, C$_{3'}$), 64.4 (d, J$_{C5'-P}$=5.0 Hz, C$_{5'}$), 39.5 (s, C$_{2'}$).

$^{31}$P NMR (D$_2$O, 121 MHz) δ 0.23 (s).

UV (H$_2$O) λ$_{max}$ 273 nm (ϵ 9100), λ$_{min}$ 246 nm (ϵ 4800).

LC/MS (M−NH$_4^+$): m/z: 306 tr: 11.23 min purity: 92.5%.

EXAMPLE 31

1-(2'-deoxy-(β-D-ribofuranosyl)-cytosine-5'-diphosphate, ammonium salts

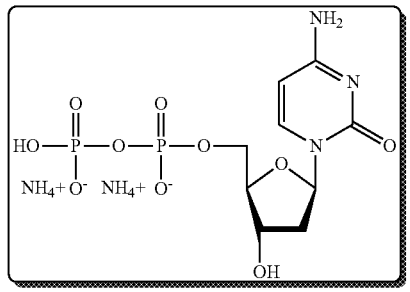

Method E of Example 26 was applied to 0.21 g of PEG-O-bis(succinyl-dCDP) (0.03 mmole). Column chromatography purification produced a mixture of dCDP and succinamide in the ratio 90/10 (27 mg). A sample of the mixture (10 mg) was dissolved in water (2 mL) and purified overnight by dialysis. 9 mg de dCDP (86%) was obtained in the form of a white solid after lyophilisation.

$R_f$ (iPrOH/H$_2$O/NH$_4$OH, 5.5/3.5/1, v/v/v): 0.6.

$^1$H NMR (D$_2$O, 300 MHz) δ 8.08 (d, J$_{6-5}$=7.8 Hz, 1H, H$_6$), 6.19 (t, J$_{1'-2'a}$=J$_{1'-2'b}$=6.6 Hz, 1H, H$_{1'}$), 6.16 (d, J$_{5-6}$=7.8 Hz, 1H, H$_5$), 4.52 (m, 1H, H$_{3'}$), 4.16-4.06 (m, 3H, H$_{4'}$, 2H$_{5'}$), 2.43-2.34 (ddd, J$_{2'a-1'}$=6.3 Hz, J$_{2'a-3'}$=3.6 Hz, J$_{2'a-2'}$=Hz, 1H, H$_{2'a}$), 2.27-2.18 (m, 1H, H$_{2'b}$).

$^{13}$C NMR (D$_2$O, 100 MHz) δ 160.5 (s, C$_4$), 147.9 (s, C$_2$), 143.9 (s, C$_6$), 95.4 (s, C$_5$), 86.5 (s, C$_{1'}$), 86.0 (s, C$_{4'}$), 70.6 (s, C$_{3'}$), 64.9 (s, C$_{5'}$), 39.5 (s, C$_{2'}$).

$^{31}$P NMR (D$_2$O, 121 MHz) δ −10.68 (d, J$_{β-α}$=19.3 Hz, P$_β$), −11.25 (d, J$_{α-β}$=16.5 Hz, P$_α$).

UV (H$_2$O) λ$_{max}$ 273 nm (ϵ 9100), λ$_{min}$ 246 nm (ϵ 4600).

LC/MS (M+H−2NH$_4^+$): m/z: 386 tr: 13.89 min purity: 77.4%.

EXAMPLE 32

1-(2'-deoxy-β-D-ribofuranosyl)-cytosine-5'-triphosphate, ammonium salts

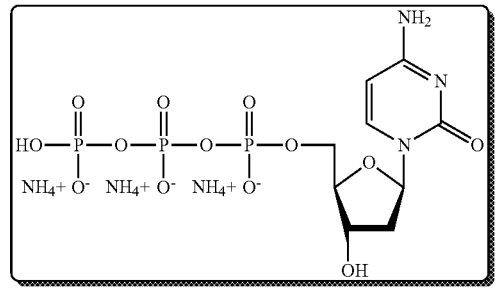

Method E of Example 26 was applied to 0.25 g of PEG-O-bis(succinyl-dCTP) (0.04 mmole). Column chromatography purification produced a mixture of dCTP and succinamide in the ratio 94/6 (30 mg). A 10 mg sample of the mixture was dissolved in water (2 mL) and purified overnight by dialysis. 9 mg of dCTP (70%) was obtained in the form of a white solid after lyophilisation.

$R_f$ (iPrOH/H$_2$O/NH$_4$OH, 5.5/3.5/1, v/v/v): 0.6.

$^1$H NMR (D$_2$O, 300 MHz) δ 8.04 (d, J$_{6-5}$=7.8 Hz, 1H, H$_6$), 6.23 (t, J$_{1'-2'a}$=J$_{1'-2'b}$=6.3 Hz, 1H, H$_{1'}$), 6.18 (d, J$_{5-6}$=7.8 Hz, 1H, H$_5$), 4.56 (m, 1H, H$_{3'}$), 4.17 (m, 3H, H$_{4'}$, 2H$_{5'}$), 2.45-2.37 (ddd, J$_{2'a-1'}$=6.0 Hz, J$_{2'a-3'}$=3.3 Hz, J$_{2'a-2'}$=14.4 Hz, 1H, H$_{2'a}$), 2.34-2.23 (m, 1H, H$_{2'b}$).

$^{13}$C NMR (D$_2$O, 100 MHz) δ 143.2 (s, C$_6$), 95.8 (s, C$_5$), 86.4 (s, C$_{1'}$), 86.7 (s, C$_{4'}$), 70.6 (s, C$_{3'}$), 65.2 (s, C$_{5'}$), 39.5 (s, C$_{2'}$).

$^{31}$P NMR (D$_2$O, 121 MHz) δ −9.62 (m, P$_γ$), −11.07 (d, J$_{α-γ}$=16.4 Hz, P$_α$), −21.93 (m, P$_β$).

UV (H$_2$O) λ$_{max}$ 273 nm (ϵ 10100), λ$_{min}$ 245 nm (ϵ 4300).

LC/MS (M+2H−3NH$_4^+$): m/z: 466 tr: 18.81 purity: 84.5%.

EXAMPLE 33

1-(β-D-ribofuranosyl)-cytosine-5'-monophosphate, ammonium salt

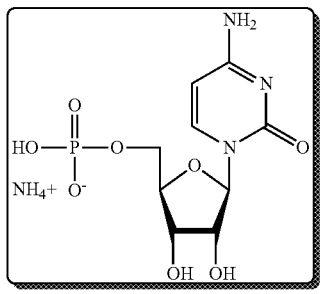

Method E of Example 26 was applied to 0.13 g of PEG-O-bis(succinyl-CMP) (0.02 mmole). Column chromatographic purification produced 17 mg of a mixture of CMP and succinamide in the ratio 80/20. A 10 mg sample of the mixture was dissolved in water (2 mL) and purified overnight by dialysis. The CMP (7 mg, 82%) was obtained in the form of a white solid after lyophilisation.

$R_f$ (iPrOH/H$_2$O/NH$_4$OH, 6/2/2, v/v/v): 0.3.

$^1$H NMR (D$_2$O, 400 MHz) δ 7.98 (d, $J_{6-5}$=7.7 Hz, 1H, H$_6$), 6.08 (d, $J_{5-6}$=7.5 Hz, 1H, H$_5$), 5.89 (d, $J_{1'-2'}$=2.6 Hz, 1H, H$_{1'}$), 4.28-4.18 (m, 3H, H$_{2'}$, H$_{3'}$, H$_{4'}$), 4.17-3.94 (m, 2H, 2H$_{5'}$).

$^{13}$C NMR (D$_2$O, 100 MHz) δ 163.6 (s, C$_4$), 154.4 (s, C$_2$), 142.3 (s, C$_6$), 96.0 (s, C$_5$), 89.4 (s, C$_{1'}$), 83.0 (d, $J_{C4'-P}$=9.0 Hz, C$_{4'}$), 74.3 (s, C$_{2'}$), 69.2 (s, C$_{3'}$), 63.7 (d, $J_{C5'-P}$=5.0 Hz, C$_{5'}$).

$^{31}$P NMR (D$_2$O, 121 MHz) δ 0.29 (s).

LC/MS (M−NH$_4^+$): m/z: 322 tr: 10.20 min purity: 86%.

EXAMPLE 34

1-(β-D-ribofuranosyl)-cytosine-5'-diphosphate, ammonium salts

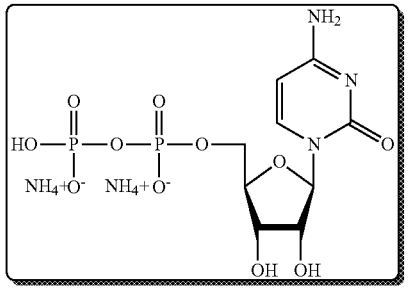

0.5 mL of triethylamine was added to a solution of 0.20 g of PEG-O-bis(succinyl-CDP) (0.03 mmole) in an ethanol/water mixture (6 mL, 1/1, v/v). The mixture was stirred at ambient temperature for 3 h and concentrated under reduced pressure. The residue was treated in accordance with method E of Example 25. Column chromatography of the product produced a mixture of CDP and succinamide in the ratio 95/5 (30 mg). A sample (10.5 mg) of the mixture was dissolved in water (2 mL) and purified overnight by dialysis on cellulose ester membranes. 9 mg of CDP (93%) was obtained in the form of a white solid after lyophilisation, contaminated with 7% of a by-product identified as the cyclic cytidine 5'-diphosphate-2',3'-monophosphate analogue.

$R_f$ (iPrOH/H$_2$O/NH$_4$OH, 5.5/3.5/1, v/v/v): 0.4.

$^1$H NMR (D$_2$O, 300 MHz) δ 7.85 (d, $J_{6-5}$=7.5 Hz, 1H, H$_6$), 5.98 (d, $J_{5-6}$=7.8 Hz, 1H, H$_5$), 5.83 (d, $J_{1'-2'}$=3.9 Hz, 1H, H$_{1'}$), 4.24-4.00 (m, 5H, H$_{2'}$, H$_{3'}$, H$_{4'}$, 2H$_{5'}$).

$^{13}$C NMR (D$_2$O, 75 MHz) δ 163.1 (s, C$_4$), 154.2 (s, C$_2$), 140.5 (s, C$_6$), 94.8 (s, C$_5$), 87.8 (s, C$_{1'}$), 81.3 (d, $J_{C4'-P}$=9.1 Hz, C$_{4'}$), 72.7 (s, C$_{2'}$), 67.7 (s, C$_{3'}$), 62.9 (d, $J_{C5'-P}$=5.4 Hz, C$_{5'}$).

$^{31}$P NMR (D$_2$O, 121 MHz) δ −10.21 (d, $J_{β-α}$=20.3 Hz, P$_β$), −11.13 (d, $J_{α-β}$=20.3 Hz, P$_α$).

UV (H$_2$O) $λ_{max}$ 270 nm (ε 10500), $λ_{min}$ 241 nm (ε 6700).

LC/MS (M+H−2NH$_4^+$): m/z: 402 tr: 14.15 min purity: 71.8%.

EXAMPLE 35

1-(β-D-ribofuranosyl)-cytosine-5'-triphosphate, ammonium salts

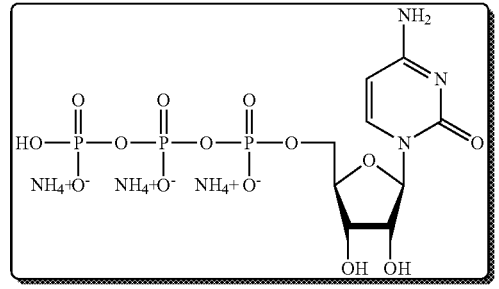

0.5 mL of triethylamine was added to a solution of 0.19 g of PEG-O-bis(succinyl-CTP) (0.03 mmole) in an ethanol/water (mixture 6 mL, 1/1, v/v). The mixture was stirred at ambient temperature for 3 h and concentrated under reduced pressure. The residue was treated in accordance with method E of Example 25. Column chromatography of the product produced 24 mg of a mixture of CTP and succinamide in the ratio 80/20. A sample (16 mg) of the mixture was dissolved in water (2 mL) and purified overnight by dialysis on cellulose ester membranes. 13 mg of CTP (81%) was obtained in the form of a white solid after lyophilisation, contaminated by 10% of a by-product identified as the cyclic cytidine-2',3' monophosphate-5'-triphosphate analogue.

$R_f$ (iPrOH/H$_2$O/NH$_4$OH, 5.5/3.5/1, v/v/v): 0.3.

$^1$H NMR (D$_2$O, 300 MHz) δ 7.94 (d, $J_{6-5}$=7.7 Hz, 1H, H$_6$), 6.10 (d, $J_{5-6}$=7.7 Hz, 1H, H$_5$), 5.88 (d, $J_{1'-2'}$=4.2 Hz, 1H, H$_{1'}$), 4.31-4.11 (m, 5H, H$_{2'}$, H$_{3'}$, H$_{4'}$, 2H$_{5'}$).

$^{13}$C NMR (D$_2$O, 75 MHz) δ 162.2 (s, C$_4$), 152.8 (s, C$_2$), 142.9 (s, C$_6$), 95.9 (s, C$_5$), 89.2 (s, C$_{1'}$), 83.1 (d, $J_{C4'-P}$=9.3 Hz, C$_{4'}$), 74.3 (s, C$_{2'}$), 69.1 (s, C$_{3'}$), 64.5 (d, $J_{C5'-P}$=5.0 Hz, C$_{5'}$).

$^{31}$P NMR (D$_2$O, 121 MHz) δ −9.72 (d, $J_{γ-β}$=19.1 Hz, P$_γ$), −11.22 (d, $J_{α-β}$=19.4 Hz, P$_α$), −22.69 (t, $J_{β-γ}$=$J_{β-α}$=19.4 Hz, P$_β$).

UV (H$_2$O) $λ_{max}$ 270 nm (ε 12500), $λ_{min}$ 228 nm (ε 5300).

LC/MS (M+2H−3NH$_4^+$): m/z: 482 tr: 17.74 purity: 75.9%.

EXAMPLE 36

1-(2',3'-dideoxy-β-D-ribofuranosyl)-cytosyl-5'-triphosphate), ammonium salts

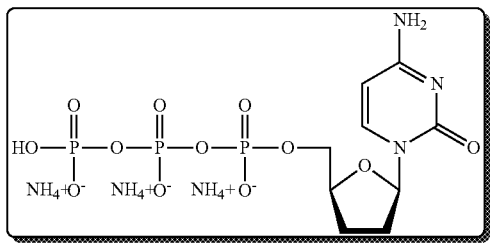

Method E of Example 26 was applied to PEG-O-bis(succinyl-ddCTP) (0.20 g, 0.03 mmole). Column chromatographic purification produced a mixture of the expected compound ddCTP and succinamide in a ratio 92/8 (30 mg). A 10.5 mg sample of the mixture was dissolved in water (2 mL) and purified overnight by dialysis. The ddCTP (9.50 mg, 67%) was obtained in the form of a white solid after lyophilisation.

$R_f$(iPrOH/H$_2$O/NH$_4$OH, 5.5/3.5/1, v/v/v): 0.7

$^1$H NMR (D$_2$O, 300 MHz) δ 8.02 (d, $J_{6-5}$=7.5 Hz, 1H, H$_6$), 6.08 (d, $J_{5-6}$=7.5 Hz, 1H, H$_5$), 6.02 (dd, $J_{1'-2'a}$=6.6 Hz, $J_{1'-2'b}$=2.0 Hz, 1H, H$_{1'}$), 4.34 (m, 1H, H$_{4'}$), 4.25 (m, 1H, H$_{5'a}$), 4.08 (m, 1H, H$_{5'b}$), 2.43-2.33 (m, 1H, H$_{2'a}$), 2.10-1.97 (m, 2H, H$_{2'b}$ H$_{3'a}$), 1.95-1.96 (m, 1H, H$_{3'b}$).

$^{13}$C NMR (D$_2$O, 75 MHz) δ 164.9 (s, C$_4$), 155.4 (s, C$_2$), 145.0 (s, C$_6$), 97.1 (s, C$_5$), 89.2 (s, C$_{1'}$), 82.8 (d, $J_{C4'-P}$=8.5 Hz, C$_{4'}$), 68.3 (d, $J_{C4'-P}$=5.4 Hz, C$_{5'}$), 33.9 (s, C$_{2'}$), 26.1 (s, C$_{3'}$).

$^{31}$P NMR (D$_2$O, 121 MHz) δ -9.76 (d, $J_{γ-β}$=19.3 Hz, P$_γ$), -10.90 (d, $J_{α-β}$=18.9 Hz, P$_α$), -22.38 (t, $J_{β-γ}$=$J_{β-α}$=18.9 Hz, P$_β$).

UV (H$_2$O) λ$_{max}$ 279 nm (ϵ 11277), λ$_{min}$ 242 nm (ϵ 2283).
LC/MS (M+2H-3NH$_4^+$): m/z: 450 tr: 16.7 purity: 76%

EXAMPLE 37

1-(2',3'-dideoxy-β-D-ribofuranosyl)-cytosyl-5'-monophosphate), ammonium salt

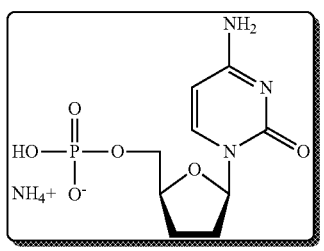

Method E of Example 26 was applied to PEG-O-succinyl-ddCMP (0.16 g, 0.03 mmole). Chromatographic column purification produced a mixture of the expected compound ddCMP and succinamide in a ratio 86/14 (17 mg). The succinamide was eliminated by overnight dialysis carried out in water (2 mL). ddCMP (14 mg, 79%) was obtained in the form of a white solid after lyophilisation.

$R_f$(iPrOH/H$_2$O/NH$_4$OH, 5.5/3.5/1, v/v/v): 0.3

$^1$H NMR (D$_2$O, 300 MHz) δ 8.06 (d, $J_{6-5}$=7.6 Hz, 1H, H$_6$), 6.02 (d, $J_{5-6}$=7.6 Hz, 1H, H$_5$), 5.93 (dd, $J_{1'-2'a}$=6.6 Hz, $J_{1'-2'b}$=2.7 Hz, 1H, H$_{1'}$), 4.27 (m, 1H, H$_{4'}$), 4.07 (m, 1H, H$_{5'a}$), 3.88 (m, 1H, H$_{5'b}$), 2.37-2.32 (m, 1H, H$_{2'a}$), 2.07-1.83 (m, 3H, H$_{2'b}$ H$_{3'a}$ H$_{3'b}$).

$^{13}$C NMR (D$_2$O, 75 MHz) δ 162.3 (s, C$_4$), 151.6 (s, C$_2$), 143.3 (s, C$_6$), 94.8 (s, C$_5$), 87.3 (s, C$_{1'}$), 81.2 (d, $J_{C4'-P}$=8.4 Hz, C$_{4'}$), 65.2 (d, $J_{C5'-P}$=5.0 Hz, C$_{5'}$), 32.0 (s, C$_{2'}$), 24.0 (s, C$_{3'}$).

$^{31}$13 NMR (D$_2$O, 121 MHz) δ 0.42 (s).

UV (H$_2$O) λ$_{max}$ 279 nm (ϵ 12276), λ$_{min}$ 245 nm (ϵ 2408).
LC/MS (M-NH$_4^+$): m/z: 290 tr: 10.75 purity: 93%

EXAMPLE 38

1-(2',3'-dideoxy-β-D-ribofuranosyl)-cytosyl-5'-diphosphate), ammonium salts

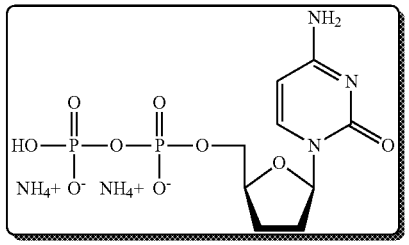

Method E of Example 26 was applied to PEG-O-succinyl-ddCDP (0.18 g, 0.03 mmole). Chromatographic column chromatography produced a mixture of the expected compound ddCDP and succinamide in a ratio 92/8 (17 mg). A 16 mg sample of the mixture was dissolved in water (2 mL) and purified overnight by dialysis. ddCDP (14.8 mg, 66%) was obtained in the form of a white solid after lyophilisation.

$R_f$(iPrOH/H$_2$O/NH$_4$OH, 5.5/3.5/1, v/v/v): 0.5

$^1$H NMR (D$_2$O, 300 MHz) δ 8.10 (d, $J_{6-5}$=7.6 Hz, 1H, H$_6$), 6.09 (d, $J_{5-6}$=7.6 Hz, 1H, H$_5$), 5.95 (dd, $J_{1'-2'a}$=6.6 Hz, $J_{1'-2'b}$=2.7 Hz, 1H, H$_{1'}$), 4.30 (m, 1H, H$_{4'}$), 4.18 (m, 1H, H$_{5'a}$), 3.99 (m, 1H, H$_{5'b}$), 2.45-2.30 (m, 1H, H$_{2'a}$), 2.10-1.80 (m, 3H, H$_{2'b}$ H$_{3'a}$ H$_{3'b}$).

$^{13}$C NMR (D$_2$O, 75 MHz) δ 161.7 (s, C$_4$), 151.8 (s, C$_2$), 143.6 (s, C$_6$), 94.8 (s, C$_5$), 87.4 (s, C$_{1'}$), 81.2 (d, $J_{C4'-P}$=8.3 Hz, C$_{4'}$), 66.1 (s, C$_{5'}$), 32.0 (s, C$_{2'}$), 24.1 (s, C$_{3'}$).

$^{31}$P NMR (D$_2$O, 81 MHz) δ -10.72 (m, P$_β$), -11.03 (m, P$_α$).

UV (H$_2$O) λ$_{max}$ 275 nm (ϵ 9803), λ$_{min}$ 245 nm (ϵ 3514).
LC/MS (M+H-2NH$_4^+$): m/z: 370 tr: 14.6 purity: 72%

EXAMPLE 39

Comparative: Method F: Monophosphorylation of a Nucleoside or Nucleoside Analogue in Solution Phosphorus oxychloride (2 eq) was added to a suspension of nucleoside (1 eq) in triethylphosphate (2 mL) at 0° C. The mixture was stirred at 0° C. for 4 h, then for 3 h at ambient temperature. The excess phosphorus oxychloride was hydrolysed by slowly adding an aqueous solution of a triethylammonium bicarbonate buffer (1M, pH=7) (5 mL). Purification was carried out by chromatography on a DEAE-cellulose, Sephadex column with a linear gradient of aqueous triethylammonium bicarbonate buffer (0-1 M). The residual phosphate salts were removed by RP18 reverse phase chromatography (isocratic; water).

EXAMPLE 40

1-(β-D-arabinofuranosyl)-cytosine-5'-monophosphate, sodium salt

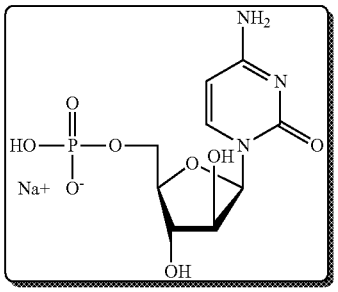

Monophosphorylation of AraC (0.2 g, 0.82 mmole) was carried out using method F (Example 36). The araCMP was obtained in the form of a white solid (0.2 g, 70%) after ion exchange on Dowex Na+ and lyophilisation.

$R_f$(iPrOH/H$_2$O/NH$_4$OH, 6/2/2, v/v/v): 0.2.

$^1$H NMR (D$_2$O, 400 MHz) δ 8.01 (d, J$_{6-5}$=7.8 Hz, 1H, H$_6$), 6.13 (d, 5.4 Hz, 1H, H$_{1'}$), 6.12 (d, J$_{5-6}$=7.8 Hz, 1H, H$_5$), 4.39 (1, J$_{2'-1'}$=J$_{2'-3'}$=5.4 Hz, 1H, H$_{2'}$), 4.15-4.08-(m, 2H, H$_{3'}$, H$_{5'a}$), 4.06-4.00 (m, 2H, H$_{4'}$, H$_{5'b}$).

$^{13}$C NMR (D$_2$O, 100 MHz) δ 161.2 (s, C$_4$), 151.0 (s, C$_2$), 144.4 (s, C$_6$), 94.7 (s, C$_5$), 85.5 (s, C$_{1'}$), 81.5 (d, J$_{C4'-P}$=9.0 Hz, C$_{4'}$), 75.3 (s, C$_{2'}$), 73.5 (s, C$_{3'}$), 63.1 (d, J$_{C5'-P}$=4.0 Hz, C$_{5'}$).

$^{31}$P NMR (D$_2$O 121 MHz) δ 0.80 (s).

UV (H$_2$O) λ$_{max}$ 272 nm (ε 8100), λ$_{min}$ 247 nm (ε 4900).

LC/MS (M–Na+): m/z: 322 tr: 12.82 min purity: 97.7%.

EXAMPLE 41

1-(β-D-ribofuranosyl)-cytosine-5'-monophosphate, triethylammonium salt

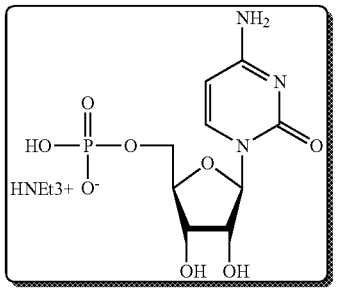

Monophosphorylation of cytidine (0.20 g, 0.82 mmole) was carried out using method F. RP18 reverse phase column purification (isocratic; water) produced CMP (0.13 g, 36%), in the form of a white solid after lyophilisation.

$R_f$(iPrOH/H$_2$O/NH$_4$OH, 6/2/2, v/v/v): 0.3.

$^1$H NMR (D$_2$O, 400 MHz) δ 7.91 (d, J$_{6-5}$=7.6 Hz, 1H, H$_6$), 6.02 (d, J$_{5-6}$=7.6 Hz, 1H, H$_5$), 5.88 (d, J$_{1'-2'}$=3.5 Hz, 1H, H$_{1'}$), 4.22-4.15 (m, 3H, H$_{2'}$, H$_{3'}$, H$_{4'}$), 4.04-4.11 (m, 1H, H$_{5'a}$), 3.94- 4.01 (m, 1H, H$_{5'b}$), 3.10 (q, J=7.3 Hz, 6H, (CH$_3$CH$_2$)$_3$NH), 1.17 (t, J=7.3 Hz, 9H, (CH$_3$CH$_2$)$_3$NH).

$^{31}$P NMR (D$_2$O, 121 MHz) δ 0.46 (s).

UV (H$_2$O) λ$_{max}$ 272 nm (ε 10238), λ$_{min}$ 247 nm (ε 6530).

LC/MS (M–HNEt$_3$+): m/z: 322 tr: 10.7 min purity: 99%.

EXAMPLE 42

1-(2'-deoxy-β-D-ribofuranosyl)-cytosine-5'-monophosphate, triethylammonium salt

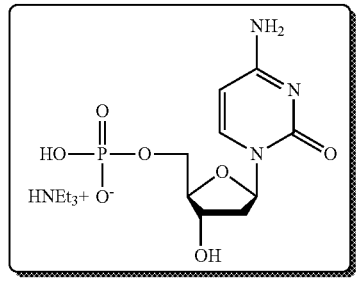

Monophosphorylation of 2'-deoxycytidine (in the hydrochloride form) (0.20 g, 0.76 mmole) was carried out using method F with the following modifications: the mixture was stirred at 15° C. instead of 0° C. for 4 h, then for 3 h at ambient temperature. RP18 reverse phase column purification (isocratic; water) produced dCMP (0.15 g, 48%) in the form of a white solid after lyophilisation and a small quantity of 5'3' dCMP (0.05 g, 11%) was also isolated in the form of a white solid.

$R_f$(iPrOH/H$_2$O/NH$_4$OH, 6/2/2, v/v/v): 0.5

$^1$H NMR (D$_2$O, 300 MHz) δ 7.96 (d, J$_{6-5}$=7.7 Hz, 1H, H$_6$), 6.20 (t, J$_{1'-2'a}$=J$_{1'-2'b}$=6.6 Hz, 1H, H$_{1'}$), 6.06 (d, J$_{5-6}$=7.7 Hz, 1H, H$_5$), 4.45 (m, 1H, H$_{3'}$), 4.11 (m, 1H, H$_{4'}$), 4.03-3.90 (m, 2H, 2H$_{5'}$), 3.10 (q, J=7.3 Hz, 6H, (CH$_3$CH$_2$)$_3$NH), 2.40-2.31 (ddd, J$_{2'a-1'}$=6.1 Hz, J$_{2'a-3'}$=3.7 Hz, J$_{2'a-2'}$=14.1 Hz, 1H, H$_{2'a}$), 2.26-2.16 (m, 1H, H$_{2'b}$), 1.19 (t, J=7.3 Hz, 9H, (CH$_3$CH$_2$)$_3$NH).

$^{31}$P NMR (D$_2$O, 121 MHz) δ 0.27 (s)

UV (H$_2$O) λ$_{max}$ 271 nm (ε 9700), λ$_{min}$ 247 nm (ε 6100).

LC/MS (M–HNEt$_3$+): m/z: 306 tr: 11.9 min purity: 100%.

EXAMPLE 43

1(β-D arabinofuranosyl)-cytosine-5'-diphosphate, sodium salts

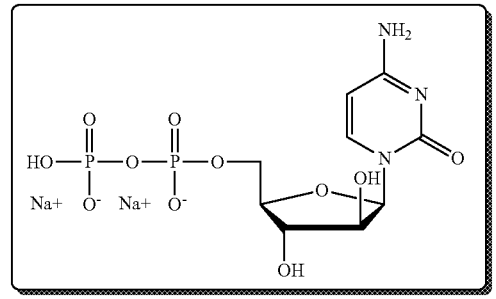

Tributylamine (0.46 mmole, 2 eq) was added to a solution of araCMP in the form of its mono(triethylammonium) salt (0.10 g, 0.23 mmole) in water (1.80 mL). The mixture was stirred for 30 min at ambient temperature. The solvents were evaporated off under reduced pressure. After co-evaporation with ethanol then anhydrous pyridine, the monophosphate was vacuum dried overnight over $P_2O_5$. 0.23 g (1.41 mmole) of 1,1'-carbonyldiimidazole was added to a suspension of this monophosphate in 5 mL of N,N-dimethylformamide. The reaction mixture was stirred for 2 h at ambient temperature and treated with anhydrous methanol (0.10 ml, 2.50 mmol) to decompose the excess 1,1'-carbonyldiimidazole. After 15 minutes, a solution (1M, 1.41 ml, 1.41 mmole) of tributylammonium phosphate in N,N-dimethylformamide was added. The suspension was stirred for 24 h at ambient temperature then filtered. The filtrate was treated with an equal volume of methanol and concentrated under reduced pressure.

After purification on DEAE-Sephadex column (linear gradient of TEAB, 0-1M), the residual phosphate salts were eliminated by RP18 reverse phase chromatography (isocratic; water). The araCDP (45 mg, 42%) was obtained in the form of a white solid after ion exchange on DOWEX Na+ and lyophilisation.

$R_f$ (iPrOH/$H_2O$/$NH_4OH$, 5.5/3.5/1, v/v/v): 0.3.

$^1$H NMR ($D_2O$, 400 MHz) δ 7.85 (d, $J_{6-5}$=7.6 Hz, 1H, $H_6$), 6.17 (d, $J_{1'-2'}$=5.6 Hz, 1H, $H_{1'}$), 6.03 (d, $J_{5-6}$=7.6 Hz, 1H, $H_5$), 4.37 (t, $J_{2'-1'}$=$J_{2'-3'}$=5.6 Hz, 1H, $H_{2'}$), 4.22 (t, $J_{3'-2'}$=6.0 Hz, 1H, $H_{3'}$), 4.17 (m, 2H, 2$H_{5'}$), 4.01 (m, 1H, $H_{4'}$).

$^{13}$C NMR ($D_2O$, 100 MHz) δ 166.1 (s, $C_4$), 157.4 (s, $C_2$), 142.7 (s, $C_6$), 95.7 (s, $C_5$), 85.1 (s, $C_{1'}$), 81.1 (d, $J_{C4'-P}$=9.0 Hz, $C_{4'}$), 75.3 (s, $C_{2'}$), 73.6 (s, $C_{3'}$), 63.6 (d, $J_{C5'-P}$=5.0 Hz, $C_{5'}$).

$^{31}$P NMR ($D_2O$, 121 MHz) δ −8.46 (m, $P_β$), −10.84 (m, $P_α$).

UV ($H_2O$) $λ_{max}$ 271 nm (ε 9100), $λ_{min}$ 247 nm (ε 5700).

LC/MS (M+H−2Na+): m/z: 402 tr: 15.8 min purity: 84.5%

EXAMPLE 44

Comparative: Method G: Triphosphorylation of Nucleosides in Solution

G1: "One Pot" Method

Phosphorus oxychloride (1.64 mmole, 2 eq) was added to a suspension of the desired nucleoside (1 eq) in triethylphosphate (2 mL) at 0° C. The mixture was stirred at 0° C. for 4 h. A solution of tributylammonium pyrophosphate in anhydrous N,N-dimethylformamide (1M, 4.11 mmole, 5 eq) was added, as well as tributylamine (0.90 mmole, 1.1 eq). The mixture was vigorously stirred for 5 min and a solution of a triethylammonium bicarbonate buffer (1M, 30 mL) was slowly added. The solvents were evaporated off under reduced pressure. Purification was carried out by DEAE-Sephadex column chromatography, eluting with a linear gradient of triethylammonium bicarbonate buffer (0-1M). The residual pyrophosphate salts were eliminated by RP18 reverse phase chromatography (isocratic; water).

G2: Carbonyldiimidazole Activation Method:

Tributylamine (0.46 mmole, 2 eq) was added to a solution of the required monophosphate in the form of its mono(triethylammonium) salt (1 eq) in water (1.80 mL). The mixture was stirred for 30 min at ambient temperature. The solvents were evaporated off under reduced pressure. After co-evaporation to from ethanol then anhydrous pyridine, the monophosphate was dried overnight under vacuum over $P_2O_5$. 1,1'-carbonyldiimidazole (1.41 mmole, 6 eq) was added to a suspension of this monophosphate in DMF (5 mL). The reaction mixture was stirred for 2 h at ambient temperature and treated with anhydrous methanol (2.30 mmole, 10 eq) to decompose the excess carbonyldiimidazole. After 15 min, a solution of tributylammonium pyrophosphate in anhydrous N,N-dimethylformamide (1M, 1.41 mmole, 6 eq) was added. The suspension was stirred for 24 h at ambient temperature, then filtered. The filtrate was treated with an equal volume of methanol, then concentrated under reduced pressure. Purification was carried out by DEAE-Sephadex column chromatography, eluting with a linear gradient of triethylammonium bicarbonate buffer (0-1 M). The residual pyrophosphate salts were removed by RP18 reverse phase chromatography (isocratic; water).

EXAMPLE 45

AraCTP

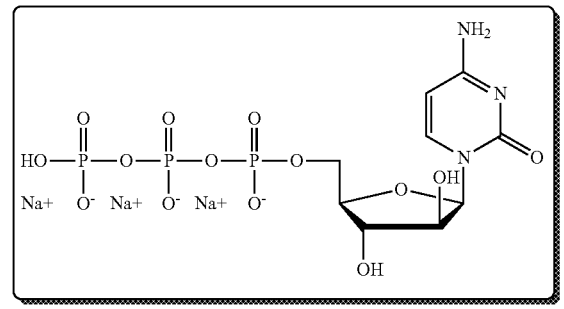

Triphosphorylation of araCMP (0.20 g, 0.82 mmole) was carried out using method G1 described above. The araCTP was obtained in the form of a white solid (0.045 mg, 10%) after ion exchange on DOWEX Na$^+$ and lyophilisation.

Triphosphorylation of the araC (0.10 g, 0.23 mmole) was also carried out using method G2 described above. After two purifications on a DEAE-Sephadex column and on a RP18 reverse phase column, the araCTP (0.015 mg, 11%) was obtained in the form of a white solid after ion exchange on Dowex then lyophilisation.

$R_f$ (iPrOH/$H_2O$/$NH_4OH$, 5.5/3.5/1, v/v/v): 0.2.

$^1$H NMR ($D_2O$, 400 MHz) δ 7.84 (d, $J_{6-5}$=7.6 Hz, 1H, $H_6$), 6.17 (d, $J_{1'-2'}$=5.4 Hz, 1H, $H_{1'}$), 6.03 (d, $J_{5-6}$=7.6 Hz, 1H, $H_5$), 4.37 (t, $J_{2'-1'}$=$J_{2'-3'}$=5.4 Hz, 1H, $H_{2'}$), 4.25-4.16 (m, 3H, $H_{3'}$ 2$H_{5'}$), 4.03 (m, 1H, $H_{4'}$).

$^{13}$C NMR ($D_2O$, 100 MHz) δ 166.0 (s, $C_4$), 157.3 (s, $C_2$), 142.8 (s, $C_6$), 95.7 (s, $C_5$), 85.3 (s, $C_{1'}$), 81.1 (d, $J_{C4'-P}$=9.0 Hz, $C_{4'}$), 75.4 (s, $C_{2'}$), 73.6 (s, $C_{3'}$), 64.0 (d, $J_{C5'-P}$=5.0 Hz, $C_{5'}$).

$^{31}$P NMR ($D_2O$, 121 MHz) δ −9.55 (d, $J_{γ-β}$=19.4 Hz, $P_γ$), −11.12 (d, $J_{α-β}$=19.4 Hz, $P_α$), −22.69 (t, $J_{β-γ}$=$J_{β-α}$=19.4 Hz, $P_β$).

UV ($H_2O$) $λ_{max}$ 271 nm (ε 10800), $λ_{min}$ 245 nm (ε 6600).

LC/MS (M+2H−3Na+): m/z: 482 tr: 18.5 min purity: 84.7%

EXAMPLE 46

CTP

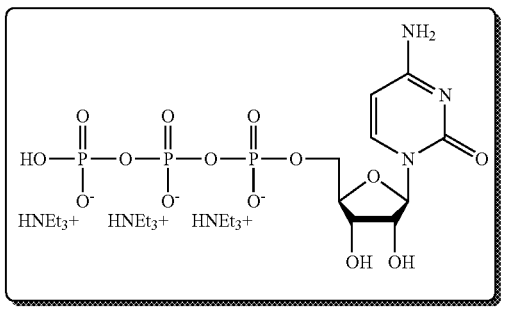

Triphosphorylation of CMP in the form of its mono(triethylammonium) salt (0.10 g, 0.23 mmole) was carried out using method G2. Purification on a DEAE-Sephadex column then an RP18 reverse phase column (isocratic; water) produced CTP (0.70 g, 37%) obtained in the form of a white solid after lyophilisation.

$R_f$ (iPrOH/H$_2$O/NH$_4$OH, 5.5/3.5/1, v/v/v): 0.3.

$^1$H NMR (D$_2$O, 300 MHz) δ 7.97 (d, $J_{6-5}$=7.7 Hz, 1H, H$_6$), 6.10 (d, $J_{5-6}$=7.7 Hz, 1H, H$_5$), 5.88 (d, $J_{1'-2'}$=4.3 Hz, 1H, H$_{1'}$) 4.30-4.12 (m, 5H, H$_{2'}$, H$_{3'}$, H$_{4'}$, 2H$_{5'}$), 3.09 (q, J=7.3 Hz, 18H, (CH$_3$CH$_2$)$_3$NH), 1.17 (t, J=7.3 Hz, 27H, (CH$_3$CH$_2$)$_3$NH).

$^{13}$C NMR (D$_2$O, 75 MHz) δ 163.4 (s, $\overline{C_4}$), 154.1 (s, C$_2$), 142.5 (s, C$_6$), 96.1 (s, C$_5$), 89.1 (s, C$_{1'}$), 83.0 (d, $J_{C4'-P}$=12.0 Hz, C$_{4'}$), 74.3 (s, C$_{2'}$), 69.2 (s, C$_{3'}$), 64.5 (d, $J_{C5'-P}$=7.0 Hz, C$_{5'}$), 46.62 (s, (CH$_3$CH$_2$)$_3$NH), 8.18 (s, (CH$_3$CH$_2$)$_3$NH).

$^{31}$P NMR (D$_2$O, $\overline{121}$ MHz) δ −10.78 (d, $\overline{J_{\beta-\gamma}}$=19.4 Hz, P$_\gamma$), −11.36 (d, $J_{\alpha-\beta}$=20.6 Hz, P$_\alpha$), −23.20 (t, $J_{\beta-\gamma}$=$J_{\beta-\alpha}$=19.4 Hz, P$_\beta$).

UV (H$_2$O) $\lambda_{max}$ 272 nm (ε 12500), $\lambda_{min}$ 242 nm (ε 7200).

LC/MS (M+2H−3HNEt3+): m/z: 482 tr: 17.1 min purity: 97.1%

EXAMPLE 47

Coupling of Nucleoside 3TC with the Support

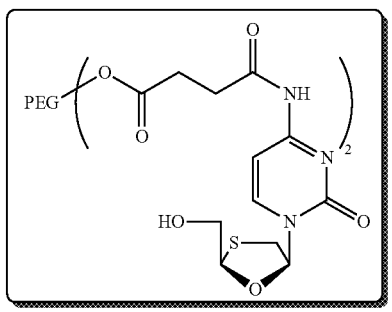

Poly(ethyleneglycol)$_{4000}$ bis[4-N-(1-(2',3'-dideoxy-3'-thia-γ-L-ribofuranosyl)-cytosyl) succinate] 6

Coupling between PEG succinate (1 g, 0.23 mmole) and 3TC (0.10 g, 0.47 mmole) was carried out using method A and PEG-3TC was obtained in the form of a white solid (0.88 g, 80%).

$R_f$ (CH$_2$Cl$_2$/MeOH, 8/2, v/v): 0.8.

$^1$H NMR (D$_2$O, 300 MHz) δ 8.42 (d, $J_{6-5}$=7.5 Hz, 1H, H$_6$), 7.25 (d, $J_{5-6}$=7.5 Hz, 1H, H$_5$), 6.24 (dd, $J_{1'-2'a}$=2.7 Hz, $J_{1'-2'b}$=5.4 Hz, 1H, H$_{1'}$), 5.31 (t, $J_{4'-5'b}$ 3.6 Hz, 1H, H$_{4'}$), 4.20-4.17 (m, (OCH$_2\alpha_{PEG}$), 3.99 (dd, $J_{5'a-4'}$=3.0 Hz, $J_{5a'-5'b}$=12.9 Hz, 1H, H$_{5'a}$), 3.90-3.34 (m, (OCH$_2$)$_{PEG}$ H$_{5'b}$ H$_{2'a}$), 3.22 (dd, H$_{2'b-1'}$=2.4 Hz, J$_{2'b-2'a}$=12.6 Hz, 1H, H$_{2'b}$), 2.79-2.65 (m, 4H, CH$_{2succ}$).

$^{13}$C NMR (D$_2$O, 100 MHz) δ 174.6, 174.5 (2s, C=O$_{succ}$), 162.6 (s, C$_4$), 156.6 (s, C$_2$), 146.1 (s, C$_6$), 97.3 (s, C$_5$), 88.0 (s, C$_{1'}$), 87.9 (s, C$_{4'}$), 69.6 (s, (OCH$_2$)$_{PEG}$), 68.4 (s, (OCH$_2\beta$)$_{PEG}$), 64.1 (s, (OCH$_2\alpha$)$_{PEG}$), 61.5 (s, C$_{5'}$), 38.0 (s, C$_{2'}$), 31.5, 28.5 (2s, CH$_{2succ}$).

EXAMPLE 48

Monophosphorylation of Nucleoside on Polymer Support by Oxidation of H-Phosphonate Method B'$_1$: Synthesis of H-Phosphonate 5'-Monoester Nucleoside Diphenylphosphite (1.60 mmole, 30 eq.) was added to a solution of PEG-nucleoside (nucleoside on polymer support) (1 eq.) in anhydrous pyridine (3.75 mL). The solution was stirred at ambient temperature for 20 min, and an aqueous triethylamine solution (1.25 mL, 1/1, v/v) was added 15 min later, then the mixture was concentrated under reduced pressure. The residue was dissolved in dichloromethane (30 mL) and the organic phase was washed with an aqueous 5% solution of NaHCO$_3$ (20 mL). The aqueous phase was extracted several times with dichloromethane (30 mL). The organic phases were combined and evaporated under reduced pressure.

The supported H-phosphonate nucleoside was precipitated from the dichloromethane solution, by addition of an excess volume of cold diethyl ether (25 mL).

The precipitated was filtered, washed with diethyl ether. The final product was re-crystallized from absolute ethanol (5 mL) and vacuum dried over KOH pellets.

EXAMPLE 49

Application to the Synthesis of the Supported Monophosphate of Nucleoside ddC Poly(ethyleneglycol)$_{4000}$ bis[4-N-(1-(2',3'-dideoxy-5'-hydrogenophosphonyl-β-D-ribo-furanosyl)-cytosyl) succinate], tri-ethylammonium salts

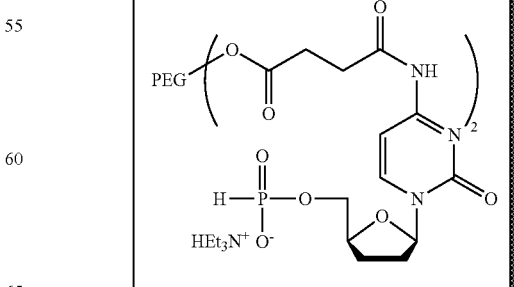

PEG-ddC (0.25 g, 0.05 mmole) was treated using method B'$_1$ of Example 48, and the H-phosphonate 5'-monoester of the supported ddC was obtained in the form of a white solid (0.23 g, 86%).

$^1$H NMR (D$_2$O, 300 MHz) δ 8.34 (d, J$_{6-5}$=7.4 Hz, 1H, H$_6$), 7.26 (d, J$_{5-6}$=7.4 Hz, 1H, H$_5$), 6.67 (d, J$_{H-P}$=637.2 Hz, 1H, H$_{HP}$), 5.99 (m, 1H, H$_{1'}$), 4.32 (m, 1H, H$_{4'}$), 4.18-4.09 (m, 3H, (OCH$_2$α)$_{PEG}$ H$_{5'a}$), 3.94 (m, 1H, H$_{5'b}$), 3.83-3.36 (m, (OCH$_2$)$_{PEG}$), 3.09 (q, J=7.2 Hz, 6H, (CH$_3$CH$_2$)$_3$NH), 2.82-2.66 (m, 4H, CH$_{2succ}$), 2.45 (m, 1H, H$_{2'a}$), 2.08-1.97 (m, 2H, H$_{2'b}$ H$_{3'a}$), 1.78 (m, 1H, H$_{3'b}$), 1.17 (t, J=7.2 Hz, 9H, (CH$_3$CH$_2$)$_3$NH).

$^{13}$C NMR (D$_2$O, 75 MHz) δ 174.5, 174.4 (2s, C=O$_{succ}$), 162.3 (s, C$_4$), 156.9 (s, C$_2$), 146.8 (s, C$_6$), 97.6 (s, C$_5$), 88.2 (s, C$_{1'}$), 86.6 (d, J$_{C4'-P}$=7.6 Hz, C$_{4'}$), 69.6 (s, (OCH$_2$)$_{PEG}$), 68.4 (s, (OCH$_2$β)$_{PEG}$), 64.1 (s, (OCH$_2$α)$_{PEG}$), 63.9 (d, J$_{C5'-P}$=3.9 Hz, C$_{5'}$), 46.6 (s, (CH$_3$CH$_2$)$_3$NH), 32.5 (s, C$_{2'}$), 31.5, 28.5 (2s, CH$_{2succ}$), 24.1 (s, C$_{3'}$), 8.2 (s, (CH$_3$CH$_2$)$_3$NH).

$^{31}$P NMR (D$_2$O, 121 MHz) δ 6.53 (s).

EXAMPLE 50

Application to the Synthesis of the Supported Monophosphate of Nucleoside 3TC

Poly(ethyleneglycol)$_{4000}$ bis[4-N-(1-(2',3'-dideoxy-5'-hydrogenophosphonyl-3'-thia-β-L-ribofuranosyl)-cytosyl) succinate], triethylammonium salts

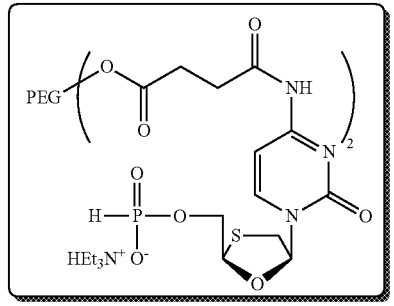

PEG-3TC (0.30 g, 0.06 mmole) was treated using method B'$_1$ of Example 48, and the H-phosphonate 5'-monoester of the supported 3TC was obtained in the form of a white solid (0.28 g, 87%).

$^1$H NMR (D$_2$O, 300 MHz) δ 8.39 (d, J$_{6-5}$=7.4 Hz, 1H, H$_6$), 7.26 (d, J$_{5-6}$=7.4 Hz, 1H, H$_5$), 6.71 (d, J$_{H-P}$=641.9 Hz, 1H, H$_{HP}$), 6.25 (s, 1H, H$_{1'}$), 5.40 (s, 1H, H$_{4'}$), 4.29-4.13 (m, 4H, (OCH$_2$α)$_{PEG}$ H$_{5'a}$H$_{5'b}$), 3.85-3.36 (m, OCH$_2$)$_{PEG}$ H$_{2'a}$), 3.22 (m, 1H, H$_{2'b}$), 3.10 (q, J=7.2 Hz, 6H, (CH$_3$CH$_2$)$_3$NH), 2.79-2.65 (m, 4H, CH$_{2succ}$), 1.18 (t, J=7.2 Hz, 9H, (CH$_3$CH$_2$)$_3$NH).

$^{13}$C NMR (D$_2$O, 100 MHz) δ 174.6, 174.5 (2s, C=O$_{succ}$), 162.6 (s, C$_4$), 156.6 (s, C$_2$), 146.1 (s, C$_6$), 97.6 (s, C$_5$), 88.0 (s, C$_{1'}$), 86.1 (s, C$_{4'}$), 69.6 (s, (OCH$_2$)$_{PEG}$), 68.4 (s, (OCH$_2$β)$_{PEG}$), 64.2 (s, (OCH$_2$α)$_{PEG}$), 63.5 (s, C$_{5'}$), 46.5 (s, (CH$_3$CH$_2$)$_3$NH), 37.8 (s, C$_{2'}$), 31.6, 28.5 (2s, CH$_{2succ}$), 8.1 (s, (CH$_3$CH$_2$)$_3$NH).

$^{31}$P NMR (D$_2$O, 121 MHz) δ 6.35 (s).

EXAMPLE 51

Method B'$_2$: Synthesis of Monophosphate by Oxidation of Nucleoside H-Phosphonate Poly(ethyleneglycol)$_{4000}$ bis[4-N-(1-(2',3'-dideoxy-5'-O-monophosphoryl-β-D-ribofuranosyl)-cytosyl) succinate], triethylammonium salts

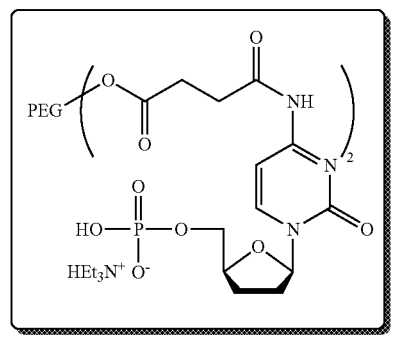

0.20 mL (0.81 mmole) of N,O-bis(trimethylsilyl)acetamide was added to a solution of PEG-ddC-H-phosphonate monoester (0.10 g, 0.02 mmole) in anhydrous acetonitrile (1.50 mL) followed by anhydrous triethylamine (0.06 mL, 0.40 mmole). The solution was stirred at 50° C. for 4 h to produce the corresponding silylated phosphite intermediate. The mixture was cooled to 0° C., and oxidation was carried out by adding a solution of tert-butyl peroxide in decane (0.36 mL, 5-6 M, 2.00 mmole) at ambient temperature. The mixture was stirred for 3 h, treated with an excess of MeOH-NEt$_3$ (0.50 mL, 5/5, v/v) and stirring was continued for 1 h. The solvents were evaporated off under reduced pressure and the residue dissolved in dichloromethane (10 mL). The organic phase was washed with an aqueous 5% sodium bicarbonate solution (7 mL) and the aqueous phase underwent several extractions with dichloromethane (10 mL). The organic phases were combined and evaporated under reduced pressure. The nucleoside 5'-monophosphate on support was precipitated from solution in dichloromethane by adding an excess volume of cold diethyl ether (100 mL). The precipitate was filtered and washed with diethyl ether. The monophosphate, slightly contaminated with a small quantity of starting product (84%/16%) was obtained in the form of a white solid (0.09 g, 89%).

$^1$H NMR (D$_2$O, 300 MHz) δ 8.49 (d, J$_{6-5}$=7.5 Hz, 1H, H$_6$), 7.13 (d, J$_{5-6}$=7.3 Hz, 1H, H$_5$), 5.98 (d, J$_{1'-2'}$=5.1 Hz, 1H, H$_{1'}$), 4.35 (m, 1H, H$_{4'}$), 4.19 (m, 3H, (OCH$_2$α)$_{PEG}$ H$_{5'a}$), 3.98-3.92 (m, 1H, H$_{5'b}$), 3.85-3.36 (m, (OCH$_2$)$_{PEG}$), 3.10 (q, J=7.2 Hz, 6H, (CH$_3$CH$_2$)$_3$NH), 2.79-2.68 (m, 4H, CH$_{2succ}$), 2.46 (m, 1H, H$_{2'a}$), 2.08 (m, 1H, H$_{2'b}$), 1.97 (m, 1H, H$_{3'a}$), 1.83 (m, 1H, H$_{3'b}$), 1.18 (t, J=7.2 Hz, 9H, (CH$_3$CH$_2$)$_3$NH).

$^{13}$C NMR (D$_2$O, 100 MHz) δ 174.5, 174.5 (2s, C=O$_{succ}$), 161.9 (s, C$_4$), 156.0 (s, C$_2$), 146.3 (s, C$_6$), 97.4 (s, C$_5$), 88.3 (s, C$_{1'}$), 81.8 (d, J$_{C4'-P}$=9.0 Hz, C$_{4'}$), 69.5 (s, (OCH$_2$)$_{PEG}$), 68.4 (s, (OCH$_2$β)$_{PEG}$), 65.2 (s, C$_{5'}$), 64.1 (s, (OCH$_2$α)$_{PEG}$), 46.6 (s, (CH$_3$CH$_2$)$_3$NH), 32.6 (s, C$_{2'}$), 31.5, 28.4 (s, CH$_{2succ}$), 23.8 (s, C$_{3'}$), 8.2 (s, (CH$_3$CH$_2$)$_3$NH).

$^{31}$P NMR (D$_2$O, 121 MHz) δ 0.37 (s).

EXAMPLE 52

Oxidation of Nucleoside 5'H-Phosphonate Monoester—an Alternative to Method B'$_2$ Poly(ethyleneglycol)$_{4000}$ bis[4-N-(1-(2',3'-dideoxy-5'-O-monophosphoryl-3'-thia-β-L-ribofuranosyl)-cytosyl) succinate], triethylammonium salts

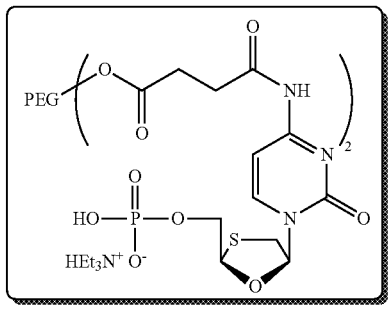

0.30 mL (1.21 mmole) of N,O-bis(trimethylsilyl)acetamide was added to a solution of PEG-3TC-H-phosphonate monoester (0.15 g, 0.03 mmole) in anhydrous pyridine (2.50 mL). The solution was stirred at 50° C. for 4 h to produce the corresponding silylated phosphite intermediate. Oxidation was carried out by adding a 200 mM solution of iodine (75 mg, 0.30 mmole) in a pyridine-water mixture (1.50 mL, 56/44, v/v) at ambient temperature. The mixture was stirred for 1 h, treated with an excess of MeOH-NEt$_3$ (1.50 mL, 50/50, v/v) and stirring was continued for 1 h. The solvents were evaporated off under reduced pressure and the residue was dissolved in dichloromethane (15 mL). The organic phase was washed with an aqueous 5% sodium thiosulphate solution (10 mL) and the aqueous phase underwent several extractions with dichloromethane (15 mL). The organic phases were combined and evaporated under reduced pressure. The 5'-monophosphate nucleoside on support was precipitated from solution in dichloromethane, by adding an excess volume of cold diethyl ether (150 mL). The precipitate was filtered and washed with diethyl ether. The final product was re-crystallized from absolute ethanol (5 mL) and vacuum dried over KOH pellets. The monophosphate PEG-3TCMP was obtained in the form of a yellow solid (0.15 g, 103%), contaminated with a residue of iodine.

$^1$H NMR (D$_2$O, 300 MHz) δ 8.44 (d, J$_{6-5}$=7.5 Hz, 1H, H$_6$), 7.26 (d, J$_{5-6}$=7.5 Hz, 1H, H$_5$), 6.25 (s, 1H, H$_{1'}$), 5.40 (s, 1H, H$_{4'}$), 4.42-4.07 (m, 4H, (OCH$_2$α)$_{PEG}$H$_{5'a}$H$_{5'b}$), 3.84-3.36 (m, (OCH$_2$)$_{PEG}$ H$_{2'a}$), 3.20 (m, 1H, H$_{2'b}$), 3.10 (q, J=7.2 Hz, 6H, (CH$_3$CH$_2$)$_3$NH), 2.82-2.67 (m, 4H, CH$_{2succ}$), 1.15 (t, J=7.2 Hz, 9H, (CH$_3$CH$_2$)$_3$NH).

$^{13}$C NMR (D$_2$O, 75 MHz) δ 174.6, 174.5 (2s, C=O$_{succ}$), 162.6 (s, C$_4$), 156.6 (s, C$_2$), 146.3 (s, C$_6$), 97.6 (s, C$_5$), 88.1 (s, C$_{1'}$), 86.2 (d, J$_{C4-P}$=8.4 Hz, C$_{4'}$), 69.6 (s, (OCH$_2$)$_{PEG}$), 68.4 (s, (OCH$_2$β)$_{PEG}$), 64.8 (s, C$_{5'}$), 64.1 (s, (OCH$_2$α)$_{PEG}$), (s, (CH$_3$CH$_2$)$_3$NH), 37.9 (s, C$_{2'}$), 31.6, 28.5 (s, CH$_{2succ}$), (s, (CH$_3$CH$_2$)$_3$NH).

$^{31}$P NMR (D$_2$O, 121 MHz) δ 0.72 (s).

EXAMPLE 53

Synthesis of Diphosphate Derivative of 3TC by Method C

Poly(ethyleneglycol)$_{4000}$ bis[4-N-(1-(2',3'-dideoxy-5'-O-diphosphoryl-3'-thia-β-L-ribofuranosyl)-cytosyl) succinate], triethylammonium salts

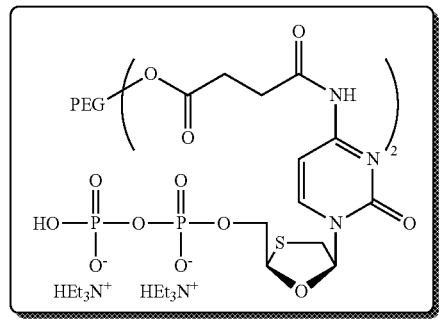

Diphosphorylation of PEG-3TCMP (0.25 g, 0.05 mmole) was carried out using method C. After ion exchange on DOWEX HNEt$_3$$^+$ and purification on a RP18 (reverse phase) column, the PEG-3TCDP diphosphate was obtained in the form of a yellow solid (0.17 g, 62%) after lyophilisation.

$^1$H NMR (D$_2$O, 300 MHz) δ 8.40 (d, J$_{6-5}$=7.5 Hz, 1H, H$_6$), 7.20 (d, J$_{5-6}$=7.8 Hz, 1H, H$_5$), 6.24 (m, 1H, H$_{1'}$), 5.42 (m, 1H, H$_{4'}$), 4.48-4.31 (m, 2H, H$_{5'a}$ H$_{5'b}$), 4.18 (m, 2H, (OCH$_2$α)$_{PEG}$), 3.84-3.34 (m, (OCH$_2$)$_{PEG}$ H$_{2'a}$), 3.21 (dd, J$_{2'b-1'}$=2.7 Hz, J$_{2'b-2'a}$=12.6 Hz, 1H, H$_{2'b}$), 3.10 (q, J=7.2 Hz, 18H, (CH$_3$CH$_2$)$_3$NH), 2.77-2.66 (m, 4H, CH$_{2succ}$), 1.17 (t, J=7.2 Hz, 27H, (CH$_3$CH$_2$)$_3$NH).

$^{13}$C NMR (D$_2$O, 75 MHz) δ 174.5, 174.4 (2s, C=O$_{succ}$), 162.6 (s, C$_4$), 156.6 (s, C$_2$), 146.2 (s, C$_6$), 97.7 (s, C$_5$), 88.1 (s, C$_{1'}$), 85.9 (d, J$_{C4'-P}$=8.6 Hz, C$_{4'}$), 69.6 (s, (OCH$_2$)$_{PEG}$), 68.4 (s, (OCH$_2$β)$_{PEG}$), 64.1 (s, (OCH$_2$α$_{PEG}$), 65.7 (s, C$_{5'}$), 46.6 (s, (CH$_3$CH$_2$)$_3$NH), 37.8 (s, C$_{2'}$), 31.6, 28.4 (2s, CH$_{2succ}$), 8.2 (s, (CH$_3$CH$_2$)$_3$NH).

$^{31}$P NMR (D$_2$O, 121 MHz) δ −10.37 (d, J$_{β-α}$=21 Hz, P$_β$), −11.36 (d, J$_{α-β}$=20.2 Hz, P$_α$).

EXAMPLE 54

Synthesis of Triphosphate Derivative of 3TC by Method D

Poly(ethyleneglycol)$_{4000}$ bis[4-N-(1-(2',3'-dideoxy-3'-thia-5'-O-triphosphoryl-β-L-ribofuranosyl)-cytosyl) succinate], triethylammonium salts

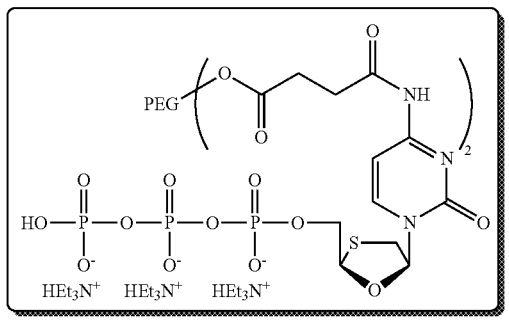

Triphosphorylation of PEG-3TCMP (0.25 g, 0.05 mmole) was carried out using method D. After ion exchange on DOWEX HNEt$_3^+$ and purification on a RP18 (reverse phase) column, PEG-3TCTP triphosphate was obtained in the form of a yellow solid (0.16 g, 54%) after lyophilisation.

$^1$H NMR (D$_2$O, 300 MHz) δ 8.41 (d, J$_{6-5}$=7.5 Hz, 1H, H$_6$), 7.20 (d, J$_{5-6}$=7.5 Hz, 1H, H$_5$), 6.24 (m, 1H, H$_{1'}$), 5.42 (m, 1H, H$_{4'}$), 4.45-4.22 (m, 2H, H$_{5'a}$ H$_{5'b}$), 4.17 (m, 2H, (OCH$_2$α)$_{PEG}$), 3.84-3.35 (m, (OCH$_2$)$_{PEG}$ H$_{2'a}$), 3.23-3.18 (m, 1H, H$_{2'b}$), 3.09 (q, J=7.2 Hz, 18H, (CH$_3$CH$_2$)$_3$NH), 2.77-2.66 (m, 4H, CH$_{2succ}$), 1.17 (t, J=7.2 Hz, 27H, (CH$_3$CH$_2$)$_3$NH).

$^{13}$C NMR (D$_2$O, 100 MHz) δ 174.6, 174.4 (2s, C=O$_{succ}$), 162.7 (s, C$_4$), 156.4 (s, C$_2$), 146.3 (s, C$_6$), 97.6 (s, C$_5$), 88.1 (s, C$_{1'}$), 86.2 (s, C$_{4'}$), 69.6 (s, (OCH$_2$)$_{PEG}$), 68.4 (s, (OCH$_2$β)$_{PEG}$), 64.1 (s, (OCH$_2$α)$_{PEG}$), 65.9 (s, C$_{5'}$), 46.6 (s, (CH$_3$CH$_2$)$_3$NH), 37.8 (s, C$_{2'}$), 31.6, 28.5 (2s, CH$_{2succ}$), 8.3 (s, (CH$_3$CH$_2$)$_3$NH).

$^{31}$P NMR (D$_2$O, 121 MHz) δ −10.83 (d, H$_{γ-β}$=18.9 Hz, P$_γ$), −11.59 (d, J$_{α-β}$=20.5 Hz, P$_α$), −23.17 (t, J$_{β-γ}$=J$_{β-α}$=20.1 Hz, P$_β$).

EXAMPLE 55

Obtaining Mono-, Di- and Triphosphate Derivatives of Nucleoside 3TC after the Cleavage Step Using Method E 1-(2',3'-dideoxy-3'-thia-(3-L-ribofuranosyl)-cytosine-5'-monophosphate, ammonium salt

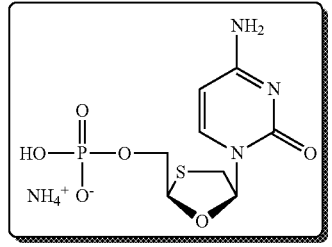

Method E was applied to PEG-3TCMP (0.14 g, 0.03 mmole). RP18 column chromatographic purification followed by a dialysis step produced 3TCMP (10.40 mg, 64%) in the form of a white solid after lyophilisation.

R$_f$ (iPrOH/H$_2$O/NH$_4$OH, 5.5/3.5/1, v/v/v): 0.4.

$^1$H NMR (D$_2$O, 300 MHz) δ 7.97 (d, J$_{6-5}$=7.5 Hz, 1H, H$_6$), 6.22 (t, J$_{1'-2'}$=4.8 Hz, 1H, H$_{1'}$), 5.96 (d, J$_{5-6}$=7.5 Hz, 1H, H$_5$), 5.35 (m, 1H, H$_{4'}$), 4.16 (ddd, J$_{5'a-4'}$=3.3 Hz, J$_{5'a-5'b}$=11.7 Hz, J$_{5'a-P}$=5.6 Hz, 1H, H$_{5'a}$), 4.07-3.99 (m, 1H, H$_{5'b}$), 3.45 (dd, J$_{2'a-2'b}$=12.3 Hz, 1H, H$_{2'a}$=5.4 Hz, 1H, H$_{2'a}$), 3.13 (dd, J$_{2'b-2'a}$=12.3 Hz, J$_{2'b-1'}$=4.2 Hz, 1H, H$_{2'b}$).

$^{13}$C NMR (D$_2$O, 75 MHz) δ 165.8 (s, C$_4$), 156.7 (s, C$_2$), 142.0 (s, C$_6$), 95.8 (s, C$_5$), 87.4 (s, C$_{1'}$), 84.6 (d, J$_{C4'-P}$=8.6 Hz, C$_{4'}$), 65.3 (d, J$_{C5'-P}$=4.7 Hz, C$_{5'}$), 36.8 (s, C$_{2'}$).

$^{31}$P NMR (D$_2$O, 121 MHz) δ 0.83 (s).

UV (H$_2$O) λ$_{max}$ 271 nm (ε 7771), λ$_{min}$ 248 nm (ε 5277).

LC/MS (M−NH$_4^+$): m/z: 308 rt: 10.80 min purity: 99%

EXAMPLE 56

1-(2',3'-dideoxy-3'-thia-β-L-ribofuranosyl)-cytosine-5'-diphosphate, ammonium salt

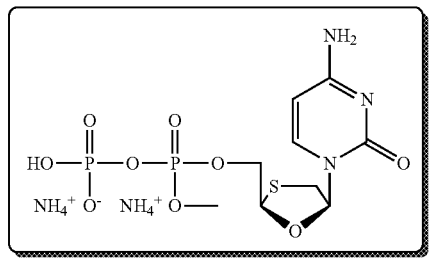

Method E was applied to PEG-3TCDP (0.25 g, 0.05 mmole). RP18 column chromatographic purification followed by a dialysis step produced 3TCDP (12 mg, 51%) in the form of a white solid after lyophilisation.

R$_f$ (iPrOH/H$_2$O/NH$_4$OH, 5.5/3.5/1, v/v/v): 0.4.

$^1$H NMR (D$_2$O, 200 MHz) δ 8.05 (d, J$_{6-5}$=7.7 Hz, 1H, H$_6$), 6.22 (t, J$_{1'-2'}$=4.8 Hz, 1H, H$_{1'}$), 6.02 (d, J$_{5-6}$=7.7 Hz, 1H, H$_5$), 5.37 (m, 1H, H$_{4'}$) 4.35-4.24 (m, 1H, H$_{5'a}$), 4.20-4.07 (m, 1H, H$_{5'b}$), 3.45 (dd, J$_{2'a-2'b}$=12.2 Hz, J$_{2'a-1}$=5.2 Hz, 1H, H$_{2'a}$), 3.15 (dd, J$_{2'b-2'a}$=12.2 Hz, J$_{2'a-1}$=4.2 Hz, 1H, H$_{2'b}$).

$^{13}$C NMR (D$_2$O, 75 MHz) δ 163.6 (s, C$_4$), 153.9 (s, C$_2$), 143.0 (s, C$_6$), 95.4 (s, C$_5$), 87.4 (s, C$_{1'}$), 84.8 (d, J$_{C4'-P}$=8.5 Hz, C$_{4'}$), 65.9 (d, J$_{C5'-P}$=5.0 Hz, C$_{5'}$), 37.0 (s, C$_{2'}$).

$^{31}$P NMR (D$_2$O, 81 MHz) δ −10.69 (d, J$_{β-α}$=20.5 Hz, P$_β$), −11.53 (d, J$_{α-β}$=20.5 Hz, P$_α$).

UV (H$_2$O) λ$_{max}$ 272 nm (ε 7769), λ$_{min}$ 248 nm (ε 5008).

LC/MS (M+H−2NH$_4^+$): m/z: 388 rt: 13.40 min purity: 79%.

EXAMPLE 57

1-(2',3'-dideoxy-3'-thia-β-L-ribofuranosyl)-cytosine-5'-triphosphate, ammonium salt

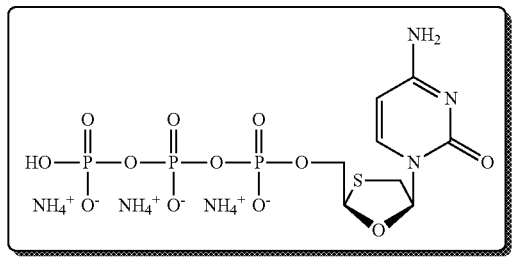

Method E was applied to PEG-3TCTP (0.25 g, 0.05 mmole). RP18 column chromatographic purification followed by a dialysis step produced 3TCTP (9 mg, 35%) in the form of a white solid after lyophilisation.

R$_f$ (iPrOH/H$_2$O/NH$_4$OH, 5.5/3.5/1, v/v/v): 0.6.

$^1$H NMR (D$_2$O, 300 MHz) δ 8.10 (d, J$_{6-5}$=7.8 Hz, 1H, H$_6$), 6.22 (t, J$_{1'-2'}$=4.8 Hz, 1H, H$_{1'}$), 6.07 (d, J$_{5-6}$=7.5 Hz, 1H, H$_5$), 5.38 (m, 1H, H$_{4'}$), 4.37-4.31 (m, 1H, H$_{5'a}$), 4.22-4.14 (m, 1H, H$_{5'b}$), 3.47 (dd, J$_{2'a-2'b}$=12.3 Hz, J$_{2'a-1}$=5.4 Hz, 1H, H$_{2'a}$), 3.18 (dd, J$_{2'b-2'a}$=12.3 Hz, J$_{2'a-1}$=3.9 Hz, 1H, H$_{2'b}$).

$^{13}$C NMR (D$_2$O, 75 MHz) δ 163.1 (s, C$_4$), 150.8 (s, C$_2$), 143.2 (s, C$_6$), 95.3 (s, C$_5$), 87.4 (s, C$_{1'}$), 84.8 (d, J$_{C4'-P}$=8.5 Hz, C$_{4'}$), 66.1 (d, J$_{C5'-P}$=5.5 Hz, C$_{5'}$), 37.0 (s, C$_{2'}$).

$^{31}$P NMR (D$_2$O, 121 MHz) δ −10.46 (d, J$_{γ-β}$=19.1 Hz, P$_γ$), −11.39 (d, J$_{α-β}$=18.9 Hz, P$_α$), −22.77 (t, J$_{β-γ}$=J$_{β-α}$=18.9 Hz, P$_β$).

UV (H$_2$O) λ$_{max}$ 272 nm (ε 7444), λ$_{min}$ 248 nm (ε 4451).

LC/MS (M+2H−3NH$_4^+$): m/z: 468 rt: 16.10 min purity: 87%.

EXAMPLE 58

Binding of Purine Nucleosides Via the Use of a Protective Group

The nucleoside was protected with a TIPS (tetra-isopropylsilyl ether) as a protective group, in accordance with Eur. J. Org. Chem. 2005, pp 5171-83.

The nucleoside was co-evaporated with pyridine (×3) and vacuum dried over KOH pellets.

Tetra-isopropylsilyl chloride (3.79 mmole, 1.02 eq.) was added to a solution of nucleoside (3.71 mmole, 1 eq.) in pyridine (10 mL) and the resulting mixture was stirred at ambient temperature for 1 h 30.

The solvent was evaporated off under reduced pressure. The oily residue was dissolved in chloromethane (20 ml) and the organic phase was washed twice with a saturated aqueous NaHCO$_3$ solution, then with brine. After evaporation under reduced pressure, the crude product was purified by silica gel column chromatography (eluent: dichloromethane/methanol 96/4).

EXAMPLE 59

Synthesis of PEG-O-bis(succinyl-2' dA)

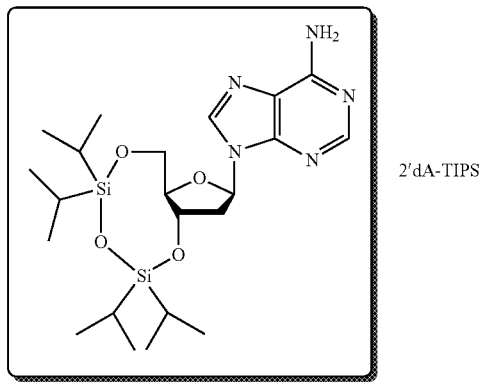

2'dA-TIPS

The synthesis was carried out as described in Example 58, from 2'-deoxyadenosine (1 g, 3.71 mmole) and after purification, 2' dA-TIPS was obtained in the form of a white solid (1.20 g, 65%).

R$_f$(dichloromethane/methanol 96/4): 0.45

$^1$H NMR (CDCl$_3$, 300 MHz) δ 8.25 (s, 1H, H$_8$), 7.96 (s, 1H, H$_2$), 6.22 (t, J$_{1'-2'a}$=J$_{1'-2'b}$=2.4 Hz, 1H, H$_{1'}$), 5.89 (s, 2H, NH$_2$), 4.87 (m, 1H, H$_{3'}$), 3.98 (m, 2H, 2H$_{5'}$), 3.82 (m, 1H, H$_{4'}$), 2.60 (m, J$_{2'a-1'}$=J$_{2'b-1'}$=2.4 Hz, 2H, H$_{2'}$), 0.962 (m, 28H, ((CH$_3$)$_2$CH)$_4$).

The invention claimed is:

1. A method for preparing a modified nucleotide or nucleotide analogue monomer comprising the following steps: (1) coupling (i) a soluble polyethylene glycol support with a molecular weight in the range 3000 to 6000 provided with at least one acid, diacid or ether-acid linker and (ii) a nucleoside or nucleoside analogue monomer at an exocyclic amine or hydroxyl group of the nucleoside or nucleoside analogue, using a coupling agent; (2) phosphorylating said nucleoside or nucleoside analogue coupled to said support with a phosphorylation agent; and (3) treating said phosphorylated nucleoside or nucleotide analogue coupled to said support so as to prepare the modified nucleotide or nucleotide analogue monomer.

2. A method according to claim 1, characterized in that said polyethylene glycol support is provided with at least one diacid or ether-acid linker and has the following formula:
   (I) RO—C$_2$H$_4$—O-PEG-O—C$_2$H$_4$—O—C(O)—(CH$_2$)$_p$—COOH, in which R is an alkyl, benzyl or aryl group or a —C(O)—(CH$_2$)$_{n'}$—COOH group, and p and n', independently of each other, represent 0 or a whole number from 1 to 10; or
   (II) RO—C$_2$H$_4$—O-PEG-O—C$_2$H$_4$—O—(CH$_2$)$_m$—COOH, in which R is an alkyl, benzyl or aryl group, or a —(CH$_2$)$_{m'}$—COOH group, and m and m', independently of each other, represent 0 or a whole number from 1 to 3.

3. A method according to claim 2, characterized in that said polyethylene glycol support is provided with at least one diacid linker of formula (I) and p in formula (I) is less than 6.

4. A method according to claim 3, characterized in that p or n' in formula (I) is a whole number from 0 to 4.

5. A method according to claim 2, characterized in that R is a linear or branched C$_1$ to C$_{12}$ alkyl or benzyl radical or an aryl radical selected from the group consisting of phenyl, tolyl and o-tolyl.

6. A method according to claim 5, characterized in that R is a methyl or benzyl radical.

7. A method according to claim 1, characterized in that the polyethylene glycol is functionalized by at least one 3-hydroxypropanoic PEG-O(CH$_2$)$_2$—COOH linker.

8. A method according to claim 1, characterized in that the nucleoside or nucleoside analogue has an exocyclic amine.

9. A method according to claim 8, characterized in that coupling is carried out between the exocyclic amine of the nucleoside or nucleoside analogue and a PEG comprising one or two succinate or 3-hydroxypropanoic linkers.

10. A method according to claim 1, characterized in that said polyethylene glycol support is provided with at least one diacid linker which has the formula PEG-[O—C(O)—(CH$_2$)$_2$—COOH]$_2$ or PEG-O(CH$_2$)$_2$—COOH.

11. A method according to claim 1, characterized in that coupling is carried out with the aid of at least one coupling agent selected from the group consisting of dimethylaminopyridine, a carbodiimide, an aromatic oxime and a coupling agent of the onium, ammonium, phosphonium or uronium type.

12. A method according to claim 1, characterized in that coupling is carried out with the aid of at least one coupling agent selected from the group consisting of dicyclohexylcarbodiimide (DCC), diisopropylcarbodiimide (DIC), dimethylaminopyridine (DMAP), 1-hydroxybenzotriazole (HOBt), 1-hydroxy-7-aza-benzotriazole (HOAt), (2-(1H-benzotriazol-1-yl)-1,1,3,3-tetramethyluronium (HBTU) hexafluorophosphate, (2-(7-aza-1H-benzotriazole-1-yl)-1,1,3,3-tetramethyluronium (HATU) hexafluorophosphate and benzotriazole-l-yl-oxy-tris-pyrrolidinophosphonium (PyBOP) hexafluorophosphate.

13. A method according to claim 12, characterized in that coupling is carried out with the aid of dimethylaminopyridine.

14. A method according to claim 1, characterized in that the soluble polyethylene glycol support has a molecular weight of approximately 4000.

15. A method according to claim 1, characterized in that the nucleoside or nucleoside analogue coupled to the support is mono -, di- or triphosphorylated in one, two or three phosphorylation steps.

16. A method according to claim 1, characterized in that phosphorylation is carried out with the aid of a derivative of phosphorus (III) or a derivative of phosphorus (V), in the presence of an activation agent or in the absence of an activation agent.

17. A method according to claim 1, characterized in that phosphorylation is carried out with the aid of a phosphorylation agent selected from phosphorus oxychlorides, trialkylammonium pyrophosphates and tetraalkylammonium phosphates.

18. A method according to claim 1, characterized in that phosphorylation is carried out with the aid of a phosphorylation agent selected from the group consisting of phosphorus oxychloride, thiophosphate trichloride, 4-nitrophenyl dichlorophosphate, tributylammonium phosphate, O-(2-chlorophenyl) dichlorothiophosphate, aminomethyl phosphonic acid, aminomethyl (methyl) phosphonic acid, 2-chloro-1,3,2-dioxaphospholane, 2-chloro-2-oxo-1,3,2-dioxaphospholane, 2-chloro-4H-1,3,2-benzodioxaphosphorin-4-one, 2-chlorophenylphosphorodichloridate, 4-chlorophenyl -phosphorodichloridate, barium 2-cyoanoethylphosphate, diethylchlorothiophosphate, dimethylchlorothiophosphate, diphenylchlorophosphate, methyl-phosphorodichloridate, phenyl -dichlorophosphate, dibenzyl-N,N-diisopropylphosphoramidite, methyldichlorophosphite and diphenylphosphite; or selected from the group consisting of tributylammonium pyrophosphate, etidronic acid, imidodiphosphate salts, imino di (methyl phosphonic acid), pyrophosphoryl tetrachloride, methyl bis(dichlorophosphonate) and methylene bisphosphonic acid.

19. A method according to claim 1, characterized in that phosphorylation is carried out with the aid of a phosphorylation agent selected from the group consisting of phosphorus oxychloride, thiophosphate trichloride, 4-nitrophenyl dichlorophosphate, diphenylphosphite and tributylammonium phosphate.

20. A method according to claim 1, characterized in that phosphorylation is carried out with the aid of pyrotributylammonium phosphate or methylene bisphosphonic acid.

21. A method according to claim 1, characterized in that phosphorylation is carried out with the aid of phosphorus oxychloride.

22. A method according to claim 1, characterized in that the phosphorylation is a monophosphorylation or a diphosphorylation of a nucleoside or nucleoside analogue with the aid of a phosphorus (V) derivative in the absence of activator.

23. A method according to claim 1, characterized in that the supported nucleoside or nucleoside analogue monophosphate obtained after monophosphorylation undergoes a diphosphorylation one or two monophosphorylation steps, with the aid of an activation agent.

24. A method according to claim 1, characterized in that phosphorylation is activated, using an activation agent selected from the group consisting of mesitylsulphonylnitrotriazole (MSNT), mesitylsulphonyltriazole (MST), mesitylsulphonyl chloride (MSCl), tri-isopropylsulphonyl chloride (TPSCl), the $Tf_2O$/4-dimethylaminopyridine (DMAP) system and 1,1-carbonyldiimidazole (CDI).

25. A method according to claim 1, further characterized in that cleavage of the linker is carried out after phosphorylation, using a base.

26. A method according to claim 1, characterized in that cleavage of the linker is carried out using a base selected from the group consisting of $NH_4OH$, MeONa and $NH_3MeOH$.

27. A method according claim 1, further characterized in that the modified nucleotide or analogue is recovered.

28. A nucleotide or nucleotide analogue coupled to a polyethylene glycol support with a molecular weight in the range 3000 to 6000 obtained by the method according to claim 1.

29. A method according to claim 25, further comprising recovering the modified nucleotide or nucleotide analogue monomer.

* * * * *

UNITED STATES PATENT AND TRADEMARK OFFICE
CERTIFICATE OF CORRECTION

PATENT NO. : 8,614,312 B2  Page 1 of 1
APPLICATION NO. : 12/735871
DATED : December 24, 2013
INVENTOR(S) : Peyrottes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 410 days.

Signed and Sealed this
Twenty-second Day of September, 2015

Michelle K. Lee
*Director of the United States Patent and Trademark Office*